US007166618B2

(12) United States Patent
Bandarage et al.

(10) Patent No.: US 7,166,618 B2
(45) Date of Patent: Jan. 23, 2007

(54) NITROSATED AND NITROSYLATED CYCLOOXYGENASE-2 INHIBITORS, COMPOSITIONS AND METHODS OF USE

(75) Inventors: Ramani R. Bandarage, Newton, MA (US); David S. Garvey, Dover, MA (US); L. Gordon Letts, Dover, MA (US); Joseph D. Schroeder, Dedham, MA (US); Sang William Tam, Dover, MA (US)

(73) Assignee: NitroMed, Inc., Lexington, MA (US)

( * ) Notice: Subject to any disclaimer, the term of this patent is extended or adjusted under 35 U.S.C. 154(b) by 178 days.

(21) Appl. No.: 10/463,671

(22) Filed: Jun. 18, 2003

(65) Prior Publication Data
US 2003/0220228 A1 Nov. 27, 2003

Related U.S. Application Data

(62) Division of application No. 09/741,816, filed on Dec. 22, 2000, now Pat. No. 6,649,629.

(60) Provisional application No. 60/226,085, filed on Aug. 18, 2000, provisional application No. 60/171,623, filed on Dec. 23, 1999.

(51) Int. Cl.
C07D 263/04 (2006.01)
A61K 31/42 (2006.01)
C07D 207/325 (2006.01)

(52) U.S. Cl. ............... 514/327; 514/376; 514/509; 546/221; 548/231; 558/482; 558/488

(58) Field of Classification Search ........... 546/221; 548/231; 558/482, 488; 514/327, 376, 509
See application file for complete search history.

(56) References Cited

U.S. PATENT DOCUMENTS

| 5,409,944 A | 4/1995 | Black et al. |
| 5,436,265 A | 7/1995 | Black et al. |
| 5,474,995 A | 12/1995 | Ducharme et al. |
| 5,510,368 A | 4/1996 | Lau et al. |
| 5,536,752 A | 7/1996 | Ducharme et al. |
| 5,550,142 A | 8/1996 | Ducharme et al. |
| 5,604,253 A | 2/1997 | Lau et al. |
| 5,604,260 A | 2/1997 | Guay et al. |
| 5,616,601 A | 4/1997 | Khanna et al. |
| 5,620,999 A | 4/1997 | Weier et al. |
| 5,621,000 A | 4/1997 | Arena et al. |
| 5,639,780 A | 6/1997 | Lau et al. |
| 5,677,318 A | 10/1997 | Lau et al. |
| 5,681,842 A | 10/1997 | Dellaria et al. |
| 5,698,584 A | 12/1997 | Black et al. |
| 5,700,947 A | 12/1997 | Del Soldato |
| 5,703,073 A | 12/1997 | Garvey et al. |
| 5,710,140 A | 1/1998 | Ducharme et al. |
| 5,733,909 A | 3/1998 | Black et al. |
| 5,750,558 A | 5/1998 | Brooks et al. |
| 5,756,531 A | 5/1998 | Brooks et al. |
| 5,776,967 A | 7/1998 | Kreft et al. |
| 5,776,984 A | 7/1998 | Dellaria et al. |
| 5,780,495 A | 7/1998 | Del Soldato |
| 5,789,413 A | 8/1998 | Black et al. |
| 5,807,873 A | 9/1998 | Nicolai et al. |
| 5,824,699 A | 10/1998 | Kreft et al. |
| 5,830,911 A | 11/1998 | Failli et al. |
| 5,849,943 A | 12/1998 | Atkinson et al. |
| 5,859,257 A | 1/1999 | Talley |

(Continued)

FOREIGN PATENT DOCUMENTS

EP   0 745 596   12/1996

(Continued)

OTHER PUBLICATIONS

Subbaramaiah et al., PubMed Abstract (Proc Soc Exp Biol Med. 216(2):201-10) Nov. 1997.*
Hida et al., PubMed Abstract (Anticancer Res. 18(2A):775-82, Mar.-Apr. 1998.*
Wilson et al., PubMed Abstract (Cancer Res. 58(14):2929-34, Jul. 1998.*
Bataar et al., Selective COX-2 Blocker Delays Healing of Esophageal Ulcers in Rats, American Journal of Pathology, vol. 160, No.3, pp. 963-972, Mar. 2002.*

(Continued)

Primary Examiner—Deepak Rao
(74) Attorney, Agent, or Firm—Wilmer Cutler Pickering Hale and Dorr LLP

(57) ABSTRACT

The present invention describes novel nitrosated and/or nitrosylated cyclooxygenase 2 (COX-2) inhibitors and novel compositions comprising at least one nitrosated and/or nitrosylated cyclooxygenase 2 (COX-2) inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or optionally, at least one therapeutic agent, such as, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures thereof. The present invention also provides novel compositions comprising at least one parent COX-2 inhibitor and at least one nitric oxide donor, and, optionally, at least one therapeutic agent. The present invention also provides kits and methods for treating inflammation, pain and fever; for treating and/or improving the gastrointestinal properties of COX-2 inhibitors; for facilitating wound healing; for treating and/or preventing renal toxicity; and for treating and/or preventing other disorders resulting from elevated levels of cyclooxygenase-2.

28 Claims, 5 Drawing Sheets

U.S. PATENT DOCUMENTS

| | | | |
|---|---|---|---|
| 5,861,419 A | 1/1999 | Dube et al. |
| 5,861,426 A | 1/1999 | Del Soldato et al. |
| 5,908,858 A | 6/1999 | Kimura et al. |
| 5,925,631 A | 7/1999 | Black et al. |
| 5,932,598 A | 8/1999 | Talley et al. |
| 5,935,990 A | 8/1999 | Khanna et al. |
| 5,945,539 A | 8/1999 | Haruta et al. |
| 5,968,958 A | 10/1999 | Guay et al. |
| 5,994,381 A | 11/1999 | Haruta et al. |
| 6,004,960 A | 12/1999 | Li et al. |
| 6,040,341 A | 3/2000 | Del Soldato et al. |
| 6,043,232 A | 3/2000 | Garvey et al. |
| 6,043,233 A | 3/2000 | Garvey et al. |
| 6,046,191 A | 4/2000 | Hamley et al. |
| 6,048,858 A | 4/2000 | Garvey et al. |
| 6,051,588 A | 4/2000 | Garvey et al. |
| 6,057,347 A | 5/2000 | Garvey et al. |
| 6,083,515 A | 7/2000 | Garvey et al. |
| 6,143,734 A | 11/2000 | Garvey et al. |
| 6,242,432 B1 | 6/2001 | Del Soldato |
| 6,248,745 B1 | 6/2001 | Hamley et al. |
| 6,297,260 B1 | 10/2001 | Bandarage et al. |
| 6,323,234 B1 | 11/2001 | Garvey et al. |
| 6,356,184 B1 | 3/2002 | Depui et al. |
| 6,369,260 B1 | 4/2002 | Sannicolo et al. |
| 6,482,846 B1 | 11/2002 | Garvey et al. |
| 6,512,137 B1 | 1/2003 | Del Soldato et al. |
| 6,593,347 B1 | 7/2003 | Bandarage et al. |
| 2004/0176331 A1* | 9/2004 | Berthelette et al. ......... 514/114 |

FOREIGN PATENT DOCUMENTS

| | | |
|---|---|---|
| EP | 0 863 134 | 9/1998 |
| EP | 0 904 110 | 7/2002 |
| WO | WO 94/04484 | 3/1994 |
| WO | WO 94/12463 | 6/1994 |
| WO | WO 94/15932 | 7/1994 |
| WO | WO 94/27980 | 12/1994 |
| WO | WO 95/00501 | 1/1995 |
| WO | WO 95/09831 | 4/1995 |
| WO | WO 95/15316 | 6/1995 |
| WO | WO 95/30641 | 11/1995 |
| WO | WO 96/25405 | 8/1996 |
| WO | WO 96/13483 | 9/1996 |
| WO | WO 96/31509 | 10/1996 |
| WO | WO 96/32946 | 10/1996 |
| WO | WO 97/03953 | 2/1997 |
| WO | WO 97/16405 | 5/1997 |
| WO | WO 97/28120 | 8/1997 |
| WO | WO 97/28121 | 8/1997 |
| WO | WO 97/31654 | 9/1997 |
| WO | WO 97/34882 | 9/1997 |
| WO | WO 97/36863 | 10/1997 |
| WO | WO 97/38986 | 10/1997 |
| WO | WO 97/40012 | 10/1997 |
| WO | WO 98/09948 | 3/1998 |
| WO | WO 98/21193 | 5/1998 |
| WO | WO 98/21195 | 5/1998 |
| WO | WO 98/47871 | 10/1998 |
| WO | WO 98/47890 | 10/1998 |
| WO | WO 99/10331 | 3/1999 |
| WO | WO 99/10332 | 3/1999 |
| WO | WO 99/12930 | 3/1999 |
| WO | WO 99/14194 | 3/1999 |
| WO | WO 99/14195 | 3/1999 |
| WO | WO 99/44595 | 9/1999 |
| WO | WO 99/45004 | 9/1999 |
| WO | WO 99/64415 | 12/1999 |
| WO | WO 00/00200 | 1/2000 |
| WO | WO 00/06585 | 2/2000 |
| WO | WO 00/25776 | 5/2000 |
| WO | WO 00/44705 | 8/2000 |
| WO | WO 00/51988 | 9/2000 |
| WO | WO 99/45004 | 9/2000 |
| WO | WO 00/61537 | 10/2000 |
| WO | WO 00/61541 | 10/2000 |
| WO | WO 00/61549 | 10/2000 |
| WO | WO 00/61604 | 10/2000 |
| WO | WO 00/72838 | 12/2000 |
| WO | WO 01/00563 | 1/2001 |
| WO | WO 01/04082 | 1/2001 |
| WO | WO 01/10814 | 2/2001 |
| WO | WO 01/12584 | 2/2001 |
| WO | WO 01/81332 A2 | 11/2001 |
| WO | WO 01/87343 A2 | 11/2001 |
| WO | WO 01/93680 A1 | 12/2001 |
| WO | WO 03/000643 A2 | 1/2002 |
| WO | WO 02/11706 A2 | 2/2002 |
| WO | WO 02/11707 A2 | 2/2002 |
| WO | WO 02/30866 | 4/2002 |
| WO | WO 02/30867 | 4/2002 |
| WO | WO 02/051385 | 7/2002 |
| WO | WO 02/053188 | 7/2002 |
| WO | WO 02/092072 A2 | 11/2002 |
| WO | WO 02/100400 A2 | 12/2002 |
| WO | WO 03/000642 A2 | 1/2003 |
| WO | WO 03/013499 | 2/2003 |
| WO | WO 03/084550 | 10/2003 |
| WO | WO 2004/000300 | 12/2003 |
| WO | WO 2004/000781 | 12/2003 |
| WO | WO 2004/011421 A1 | 2/2004 |

OTHER PUBLICATIONS

Colville-Nash et al., PubMed Abstract (BioDrugs 15(1):1-9) 2001.*
Morales et al., COX-2 Inhibitor-Associated Acute Renal Failure, Pharmacotherapy 22(10):1317-1321, 2002.*
Capone et al., Medscape Abstract (Int J Immunopathol Pharmacol 16(2 Suppl): 49-58), May-Aug 2003.*
Antman et al., COX Inhibition and Cardiovascular Risk, Circulation 112:759-770, Aug. 2005.*
Mukherjee et al., Cardiovascular Risk and COX-2 Inhibitors, Arthritis Research and Therapy, vol. 5, No. 1, pp. 8-11, 2003.*
Del Soldato et al, Br. J. Pharmac., 67:33-37 (1979).
Williams et al., Cancer Research, 61:3285-3289 (Apr. 15, 2001).
Wallace et al, Exp. Opin. Invest. Drugs, 4(7) :613-619 (1995).
Wallace et al., Trends Pharamcol., Sci., 15(11): 405-406 (1994).
Wallace et al., J. Gastroenterol. Hepatol., 9: S40-S44 (1994).
Wallace et al., Novel Molecular Approacehs to Anti-inflammatory Theory, 121-129 (1994).
Wallace et al., Gastroenterol., 106(4), Part 2, A208 (1994) Abstract.
Wallace et al., Eur. J. Pharmacol., 257:249-255 (1994).
Wallace et al., Gastroenterol., 107:173-179 (1994).
Reuter et al., Life Sciences, 55(1):1-8 (1994).
Reuter et al., Gastroenterol., 106 (4), A759 (1994).
Cuzzolin et al, Pharmacol. Res. 29(1);89-97 (1994).
Rachmilewitz et al., Gut, 35:1394-1397 (1994).
Conforti et al., Agents Action, 40(3): 176-180 (1993).
Carty et al., Agents Actions., 39: 157-165 (1993).
Cuzzolin et al, Pharmacol. Res. 31:61-65 (1995).
Barrachina et al., Eur. J. Pharmacol., 281: R3-R4 (1995).
MacNaughton et al., Life Sciences, 45: 1869-1876 (1989).
Kitigawa et al., J. Pharamcol. Exp. Therp., 253: 1133-1137 (1990).
Langford et al., Arterioscler. Thromb. Vasc. Biol. 16: 51-57 (1996).
Palmer et al., Nature, 333:664-444 (1998).
Wallace et al., J. Clin. Invest., 96: 2711-2718 (1995).
Konturek et al., Eur. J. Pharmacol., 239:215-217 (1993).
Boughton-Smith et al., Eur. J. Pharmacol., 191:485-488 (1990).
Elliott et al., Gastroenterol., 109: 524-530 (1995).
Wallace et al., Eur. J. Pharmacol., 280:63-68 (1995).
Brown et al., Eur. J. Pharmacol., 223:103-104 (1992).
Freston, The American Journal of Medicine, 107 (6A) :78S-89S (1999) (full journal arcticle).

Naesdal et al, European Journal of Gastroenterology & Hepatology, 13 (12):1401-1406 (2001) (full journal article).

Erol, Dilek Demir and Mutlu Dilsiz Axtermir. "Synthesis of Ethanone and Ethanol Derivatives of 2-Benzoxazolinone; Potent Analgesic and Antiinflammatory Compounds Inhibiting Prostaglandin E2," II Farmaco, vol. 50, No. 3, pp. 167-173. (1995).

Passarotti, C. M., et al. "In the search for new antiinflammatory drugs: Synthesis and antiinflammatory activity of some Thiazolo (3,2-a) pyrimidine derivatives containing a thioether rgoup." Boll. Chim. Farmaceutico, vol. 134, No. 11, pp. 639-643. (1995).

Winter, Charles A. et al. "Carrageenin-Induced Edema in Hind Paw of the Rat as an Assay for Antiinflammatory Drugs." Proc. Soc. Exp. Biol., vol. 111, pp. 554-547. (1962).

* cited by examiner

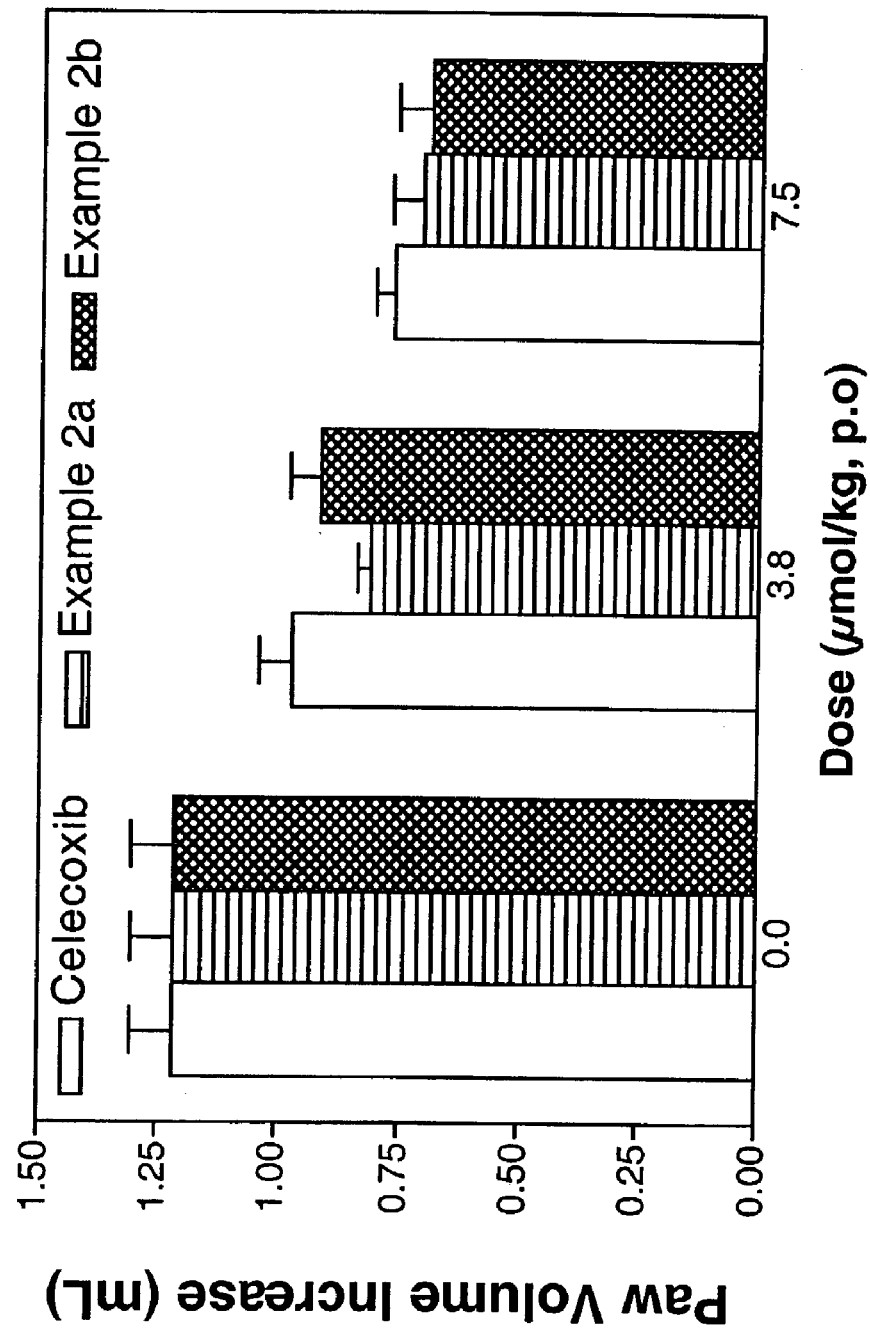

NITROSATED AND NITROSYLATED CYCLOOXYGENASE-2 INHIBITORS, COMPOSITIONS AND METHODS OF USE

RELATED APPLICATIONS

This application is a divisional of U.S. application Ser. No. 09/741,816, filed Dec. 22, 2000, U.S. Pat. No. 6,649,629, which claims priority under 35 USC 119 to U.S. Provisional Application No. 60/17 1,623 filed Dec. 23, 1999 and U.S. Provisional Application No. 60/226,085 filed Aug. 18, 2000.

FIELD OF THE INVENTION

The present invention describes novel nitrosated and/or nitrosylated cyclooxygenase 2 (COX-2) inhibitors and novel compositions comprising at least one nitrosated and/or nitrosylated cyclooxygenase 2 (COX-2) inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The present invention also provides novel compositions comprising at least one COX-2 inhibitor. The present invention also provides methods for treating inflammation, pain and fever; for treating and/or improving the gastrointestinal properties of COX-2 inhibitors; for facilitating wound healing; for treating and/or preventing renal toxicity; and for treating and/or preventing other disorders resulting from elevated levels of cyclooxygenase-2.

BACKGROUND OF THE INVENTION

Nonsteroidal anti-inflammatory compounds (NSAIDs) are widely used for the treatment of pain, inflammation, and acute and chronic inflammatory disorders such as osteoarthritis and rheumatoid arthritis. These compounds inhibit the activity of the enzyme cyclooxygenase (COX), also known as prostaglandin G/H synthase, which is the enzyme that converts arachidonic acid into prostanoids. The NSAIDs also inhibit the production of other prostaglandins, especially prostaglandin $G_2$, prostaglandin $H_2$ and prostaglandin $E_2$, thereby reducing the prostaglandin-induced pain and swelling associated with the inflammation process. The chronic use of NSAIDs has been associated with adverse effects, such as gastrointestinal ulceration and renal toxicity. The undesirable side effects are also due to the inhibition of prostaglandin in the affected organ.

Recently two isoforms of cyclooxygenase, encoded by two distinct genes (Kujubu et al, *J. Biol. Chem.*, 266, 12866–12872 (1991)), have been identified—a constitutive form, cyclooxygenase-1 (COX-1), and an inductive form, cyclooxygenase-2 (COX-2). It is thought that the antiinflammatory effects of NSAIDs are mediated by the inhibition of COX-2, whereas the side effects seem to be caused by the inhibition of COX-1. The NSAIDs currently on the market either inhibit both isoforms of COX with little selectivity for either isoform or are COX-1 selective. Recently compounds that are selective COX-2 inhibitors have been developed and marketed. These selective COX-2 inhibitors have the desired therapeutic profile of an antiinflammatory drug without the adverse effects commonly associated with the inhibition of COX-1. However, these compounds can result in dyspepsia and can cause gastropathy (Mohammed et al, *N. Engl. J. Med.*, 340(25) 2005 (1999)).

Selective COX-2 inhibitors are disclosed in, for example, U.S. Pat. Nos. 5,681,842, 5,750,558, 5,756,531, 5,776,984 and in WO 97/41100, WO 98/39330, WO 99/10331, WO 99/10332 and WO 00/24719 assigned to Abbott Laboratories; and in WO 98/50075, WO 00/29022 and WO 00/29023 assigned to Algos Pharmaceutical Corporation; and in WO 99/15205 assigned to Almirall Prodesfarma S. A.; and in U.S. Pat. No. 5,980,905 assigned to AMBI Inc.; and in U.S. Pat. No. 5,945,538 assigned to American Cyanamid Company; and in U.S. Pat. Nos. 5,776,967, 5,824,699, 5,830,911 and in WO 98/04527 and WO 98/21195 assigned to American Home Products Corporation; and in WO 98/22442 assigned to Angelini Richerche S. P. A. Societa Consortile; and in U.S. Pat. No. 6,046,191 and in WO 99/18960 and WO 00/00200 assigned to Astra Pharmaceuticals Ltd.; and in U.S. Pat. No. 5,905,089 assigned to Board of Supervisors of Louisiana State University; and in WO 97/13767 assigned to Chemisch Pharmazeutische Forschungsgesellschaft MBH; and in WO 98/57924 and WO 99/61436 assigned to Chugai Seiyaku Kabushiki Kaisha; and in WO 00/13685 assigned to Cornell Research Foundation Inc.; and in WO 96/10021 assigned to The Du Pont Merck Pharmaceutical Company; and in EP 0 087 629 B1 assigned to E.I. Du Pont de Nemours and Company; and in WO 99/13799 assigned to Euro-Celtique; and in U.S. Pat. No. 5,134,142 and in WO 91/19708, WO 97/13755, WO 99/15505, WO 99/25695 and in EP 0 418 845 B1 and EP 0 554 829 A2 assigned to Fujisawa Pharmaceutical Co. Ltd.; and in U.S. Pat. Nos. 5,344,991, 5,393,790, 5,434,178, 5,466,823, 5,486,534, 5,504,215, 5,508,426, 5,510,496, 5,516,907, 5,521,207, 5,563,165, 5,580,985, 5,596,008, 5,616,601, 5,620,999, 5,633,272, 5,643,933, 5,668,161, 5,686,470, 5,696,143, 5,700,816, 5,719,163, 5,753,688, 5,756,530, 5,760,068, 5,859,257, 5,908,852, 5,935,990, 5,972,986, 5,985,902, 5,990,148, 6,025,353, 6,028,072, 6,136,839 and in WO 94/15932, WO 94/27980, WO 95/11883, WO 95/15315, WO 95/15316, WO 95/15317, WO 95/15318, WO 95/21817, WO 95/30652, WO 95/30656, WO 96/03392, WO 96/03385, WO 96/03387, WO 96/03388, WO 96/09293, WO 96/09304, WO 96/16934, WO 96/25405, WO 96/24584, WO 96/24585, WO 96/36617, WO 96/38418, WO 96/38442, WO 96/41626, WO 96/41645, WO 97/11704, WO 97/27181, WO 97/29776, WO 97/38986, WO 98/06708, WO 98/43649, WO 98/47509, WO 98/47890, WO 98/52937, WO 99/22720, WO 00/23433, WO 00/37107, WO 00/38730, WO 00/38786 and WO 00/53149 assigned to G. D. Searle & Co.; and in WO 96/31509, WO 99/12930, WO 00/26216 and WO 00/52008 assigned to Glaxo Group Limited; and in EP 1 006 114 A1 and in WO 98/46594 assigned to Grelan Pharmaceutical Co. Ltd.; and in WO 97/34882 assigned to Grupo Farmaceutico Almirall; and in WO 97/03953 assigned to Hafslund Nycomed Pharma AG; and in WO 98/32732 assigned to Hoffmann-La Roche AG; and in U.S. Pat. Nos. 5,945,539, 5,994,381, 6,002,014 and in WO 96/19462, WO 96/19463 and in EP 0 745 596 A1 assigned to Japan Tobacco, Inc.; and in U.S. Pat. Nos. 5,686,460, 5,807,873 and in WO 97/37984, WO 98/05639, WO 98/11080 and WO 99/21585 assigned to Laboratories USPA; and in WO 99/62884 assigned to Laboratories Del Dr. Esteve, S. A.; and in WO 00/08024 assigned to Laboratorios S.A.L.V.A.T., S.A.; and in U.S. Pat. Nos. 5,585,504, 5,840,924, 5,883,267, 5,925,631, 6,001,843, 6,080,876 and in WO 97/44027, WO 97/44028, WO 97/45420, WO 98/00416, WO 98/47871, WO 99/15503, WO 99/15513, WO 99/20110, WO 99/45913, WO 99/55830, WO 00/25779 and WO 00/27382 assigned to Merck & Co. Inc.; and in U.S. Pat. Nos. 5,409,944, 5,436, 265, 5,474,995, 5,536,752, 5,550,142, 5,510,368, 5,521,213, 5,552,422, 5,604,253, 5,604,260, 5,639,780, 5,677,318, 5,691,374, 5,698,584, 5,710,140, 5,733,909, 5,789,413, 5,817,700, 5,840,746, 5,849,943, 5,861,419, 5,981,576, 5,994,379, 6,020,343, 6,071,936, 6,071,954 and in EP 0 788 476 B1, EP 0 863 134 A1, EP 0 882 016 B1 and in WO 94/20480, WO 94/13635, WO 94/26731, WO 95/00501, WO 95/18799, WO 96/06840, WO 96/13483, WO 96/19469, WO 96/21667, WO 96/23786, WO 96/36623, WO 96/37467, WO 96/37468, WO 96/37469, WO 97/14691, WO 97/16435, WO 97/28120, WO 97/28121, WO 97/36863, WO 98/03484, WO 98/41511, WO 98/41516, WO 98/43966, WO 99/14194, WO 99/14195, WO 99/23087, WO 99/41224 and WO 00/68215 assigned to Merck Frosst Canada & Co., and in WO 99/59635 assigned to Merck Sharp & Dohme Limited; and in U.S. Pat. No. 5,380,738 assigned to Monsanto Company; and in WO 00/01380 assigned to A. Nattermann & Co.; and in WO 99/61016 assigned to Nippon Shinyaku Co. Ltd.; and in WO 99/33796 assigned to Nissin Food Products Co. Ltd.; and in WO 99/11605 assigned to Novartis A G; and in WO 98/33769 assigned to Nycomed Austria GMBH; and in U.S. Pat. Nos. 6,077,869 and 6,083,969 and in WO 00/51685 assigned to Ortho-McNeil Pharmaceutical, Inc.; and in U.S. Pat. No. 5,783,597 assigned to Ortho Pharmaceutical Corporation; and in WO 98/07714 assigned to Oxis International Inc.; and in WO 00/10993 assigned to Pacific Corporation; and in EP 0 937 722 A1 and in WO 98/50033, WO 99/05104, WO 99/35130 and WO 99/64415 assigned to Pfizer Inc.; and in WO 00/48583 assigned to Pozen Inc.; and in U.S. Pat. No. 5,908,858 assigned to Sankyo Company Limited; and in WO 97/25045 assigned to SmithKline Beecham Corporation; and in U.S. Pat. No. 5,399,357 assigned to Takeda Chemical Industries, Ltd.; and in WO 99/20589 assigned to The University of Sydney; and in U.S. Pat. No. 5,475,021 and WO 00/40087 assigned to Vanderbilt University; and in WO 99/59634 assigned to Wakamoto Pharmaceutical Co. Ltd., the disclosures of each of which are incorporated by reference herein in their entirety.

There is still a need in the art for COX-2 inhibitor compounds that have gastroprotective properties, facilitate wound healing, decreased renal toxicity and dyspepsia, and that can be used at low dosages. The present invention is directed to these, as well as other, important ends.

SUMMARY OF THE INVENTION

The present invention provides novel nitrosated and/or nitrosylated COX-2 inhibitors, which are COX-2 inhibitors linked to at least one nitrogen monoxide group (NO), and/or at least one nitrogen dioxide group ($NO_2$) (i.e., nitrosylated and/or nitrosated group, respectively). The resulting compounds are potent analgesics, have antiinflammatory properties and have an unexpected potential for facilitating wound healing. The novel compounds also have unexpected properties in the treatment and/or prevention of renal toxicity. The COX-2 inhibitors can be nitrosated and/or nitrosylated through one or more sites, such as oxygen (hydroxyl condensation), sulfur (sulfhydryl condensation) and/or nitrogen. The COX-2 inhibitor can be, for example, a sulfonamide containing 1,5-diarylpyrazole derivative, such as, for example, CELEBREX® (4-(5-(4-methylphenyl)-3-(trifluoromethyl)-1H-pyrazol-1-yl)benzenesulfonamide, Celecoxib). The COX-2 inhibitor can also be, for example, a methylsulfonylphenyl-furanone derivative, such as, for example, Rofecoxib (VIOXX®, 4-(4'-methylsulfonylphenyl)-3-phenyl-2-(5H)-furanone). The present invention also provides compositions comprising such compounds in a pharmaceutically acceptable carrier.

The present invention is also based on the discovery that administering at least one nitrosated and/or nitrosylated COX-2 inhibitor and at least one nitric oxide donor reduces the gastrointestinal distress induced by COX-2 inhibitors. A nitric oxide donor is a compound that contains a nitric oxide moiety and which releases or chemically transfers nitric oxide to another molecule. Nitric oxide donors include, for example, S-nitrosothiols, nitrites, nitrates, N-oxo-N-nitrosamines, and substrates of the various isozymes of nitric oxide synthase. Thus, another aspect of the invention provides compositions comprising at least one COX-2 inhibitor that is substituted with at least one NO and/or $NO_2$ group (i.e., nitrosylated and/or nitrosated), and at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase.

Yet another aspect of the invention provides compositions comprising at least one COX-2 inhibitor that is substituted with at least one NO and/or $NO_2$ group (i.e., nitrosylated and/or nitrosated), and, optionally, at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase, and, optionally, at least one therapeutic agent, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like.

Another aspect of the invention provides compositions comprising at least one parent COX-2 inhibitor and at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase, and, optionally, at least one therapeutic agent, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like.

Yet another aspect of the present invention provides methods for treating and/or preventing inflammation, pain and fever; for treating and/or improving gastrointestinal properties of COX-2 inhibitors; for facilitating wound healing; for treating and/or preventing renal toxicity; and for treating and/or preventing COX-2 mediated disorders (i.e., disorders resulting from elevated levels of COX-2) in a patient in need thereof which comprises administering to the patient a therapeutically effective amount of at least one nitrosated and/or nitrosylated COX-2 inhibitor compound, and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e., NO donors). The method can optionally further comprise the administration of at least one therapeutic agent, such as, for example, steroids, nonsteroidal anti-inflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures thereof. In this aspect of the invention, the methods can involve administering nitrosated and/or nitrosylated COX-2 inhibitors, administering nitrosated and/or nitrosylated COX-2 inhibitors and NO donors, administering nitrosated and/or nitrosylated COX-2 inhibitors and therapeutic agents, or administering nitrosated and/or nitrosylated COX-2 inhibitors, NO donors and therapeutic agents. The nitrosated and/or nitrosylated COX-2 inhibitors, nitric oxide donors, and/or therapeutic agents can be administered separately or as components of the same composition in one or more pharmaceutically acceptable carriers.

Another aspect of the present invention provides methods for treating inflammation, pain and fever; for treating and/or improving the gastrointestinal properties of COX-2 inhibitors; for facilitating wound healing; for treating and/or preventing renal toxicity; and for treating and/or preventing other cyclooxygenase-2 mediated disorders comprising administration of at least one parent COX-2 inhibitor and at least one nitric oxide donor, and, optionally, at least one therapeutic agent.

Yet another aspect of the present invention provides kits comprising at least one nitrosated and/or nitrosylated COX-2 inhibitor, and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase. The kit can further comprise at least one therapeutic agent. The nitrosated and/or nitrosylated COX-2 inhibitor, the nitric oxide donor and/or therapeutic agent, can be separate components in the kit or can be in the form of a composition in one or more pharmaceutically acceptable carriers.

Yet another aspect of the present invention provides kits comprising at least one parent COX-2 inhibitor and at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase. The kit can further comprise at least one therapeutic agent. The parent COX-2 inhibitor, the nitric oxide donor and/or therapeutic agent, can be separate components in the kit or can be in the form of a composition in one or more pharmaceutically acceptable carriers.

These and other aspects of the present invention are explained in detail herein.

BRIEF DESCRIPTION OF THE FIGURES

FIG. 5 shows that anti-inflammatory effect of (a) Celecoxib (open bars); (b) Example 2a (non-nitrosated compound, horizontal stripped bars); and (c) Example 2b (nitrosated compound, hatched bars) using the carrageenan-induced paw edema test. Total samples, 5 for each concentration of test compound. The x axis corresponds to the dose of the test compounds in μmol/kg body weight of the rats. The y axis corresponds to the increase in the paw volume (mL). Results are expressed as the mean±standard error of the change in paw volume. Data was analyzed by AVONA analysis followed by Student Newmann-Keuls post-hoc test.

DETAILED DESCRIPTION OF THE INVENTION

Figure 1:
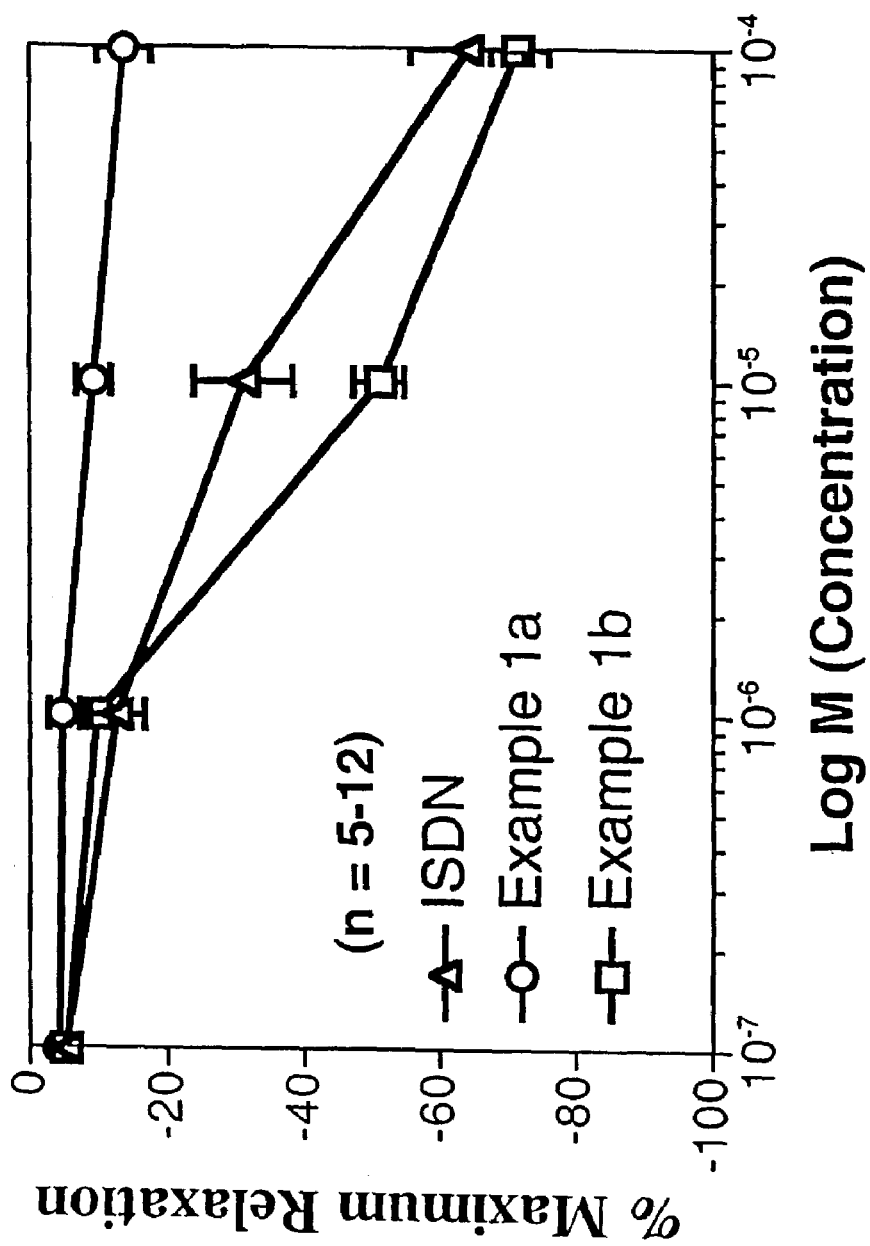
FIG. 1 shows the relaxation of rat aortic smooth muscle rings by (a) isosorbide dinitrate (ISDN, open triangles); (b) Example 1a (non-nitrosated compound, open circles); and (c) Example 1b (nitrosated compound, open squares). The non-nitrosated compound of Example 1a did not relax the tissue. At higher concentrations, the relaxation of the nitrosated compound of Example 1b was similar to that obtained with ISDN. Total number of samples tested varied from a minimum of 5 to a maximum of 12. In the x axis, log M corresponds to ten fold increases of the test compound from 100 nM ($10^{-7}$) to 100 μM ($10^{-4}$). Results are expressed as the mean±standard error of the mean of the percentage of total relaxation induced by 10 μM phenylephrine.

As used throughout the disclosure, the following terms, unless otherwise indicated, shall be understood to have the following meanings.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) inhibitor" refers to a compound that selectively inhibits the cyclooxygenase-2 enzyme over the cyclooxygenase-1 enzyme. Preferably, the compound has a cyclooxygenase-2 $IC_{50}$ of less than about 0.5 µM, and also has a selectivity ratio of cyclooxygenase-2 inhibition over cyclooxygenase-1 inhibition of at least 50, and more preferably of at least 100. Even more preferably, the compound has a cyclooxygenase-1 $IC_{50}$ of greater than about 1 µM, and more preferably of greater than 20 µM. The compound can also inhibit the enzyme, lipoxygenase and/or phosphodiestase. Such preferred selectivity may indicate an ability to reduce the incidence of common NSAID-induced side effects.

"Parent COX-2 inhibitor" refers to a non-nitrosated and/or non-nitrosylated COX-2 inhibitor and includes those described in the prior art, including those described in the patents and publications cited herein, as well as the novel compounds described herein. "Parent COX-2 inhibitor" includes the compounds of formulas I to XVI before they are nitrosated and/or nitrosylated by the methods described herein.

"Therapeutic agent" includes any therapeutic agent that can be used to treat or prevent the diseases described herein. "Therapeutic agents" include, for example, steroids, nonsteroidal antiinflammatory compounds, 5-lipoxygenase inhibitors, leukotriene $B_4$ receptor antagonists, leukotriene $A_4$ hydrolase inhibitors, 5-HT agonists, 3-hydroxy-3-methyl-glutaryl coenzyme A inhibitors, $H_2$ antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. Although NO donors have therapeutic activity, the term "therapeutic agent" does not include the NO donors described herein, since NO donors are separately defined.

"Patient" refers to animals, preferably mammals, most preferably humans, and includes males and females, and children and adults.

"Therapeutically effective amount" refers to the amount of the compound and/or composition that is effective to achieve its intended purpose.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO—, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to a branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, isoamyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$–$C_4$ hydrocarbon which can comprise one or two carbon-carbon double bonds.

"Substituted alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta,1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary aryloxy groups include napthyloxy, quinolyloxy, isoquinolizinyloxy, and the like.

"Alkylthio" refers to $R_{50}S$—, wherein $R_{50}$ is an alkyl group, as defined herein.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxo" refers to =O.

"Oxy" refers to —$O^-R_{77}^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{52}R_{53}N$—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino or arylalkylamino" refers to $R_{52}R_{55}N$—, wherein $R_{52}$ is an alkyl group, as defined herein, and $R_{55}$ is an aryl group, as defined herein.

"Alkylarylalkylamino" refers to $R_{52}R_{79}N$—, wherein $R_{52}$ is an alkyl group, as defined herein, and $R_{79}$ is an arylalkyl group, as defined herein.

"Alkylcycloalkylamino" refers to $R_{52}R_{80}N$—, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —$S(O)_2^-$.

"Sulfonic acid" refers to —$S(O)_2OR_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein "Sulfonic ester" refers to —$S(O)_2OR_{58}$, wherein $R_{58}$ is an alkyl group, an aryl group or an aryl heterocyclic ring, as defined herein.

"Sulfonamido" refers to —$S(O)_2$—$N(R_{51})(R_{57})$, wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S$—, wherein $R_{50}$ is an alkyl group, as defined herein (preferably a lower alkyl group, as defined herein).

"Arylthio" refers to $R_{55}S$—, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}$—S(O)—, wherein $R_{50}$ is an alkyl group, as defined herein.

"Alkylsulfonyl" refers to $R_{50}$—$S(O)_2$—, wherein $R_{50}$ is an alkyl group, as defined herein.

"Alkylsulfonyloxy" refers to $R_{50}$—$S(O)_2$—O—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—$S(O)_2$—, wherein $R_{55}$ is an aryl group, as defined herein.

"Arylsulfonyloxy" refers to $R_{55}$—$S(O)_2$—O—, wherein $R_{55}$ is an aryl group, as defined herein.

"Amidyl" refers to $R_{51}C(O)N(R_{57})$— wherein $R_{51}$ and $R_{57}$ are each independently a hydrogen atom, an alkyl group, an aryl group or an arylheterocyclic ring, as defined herein.

"Ester" refers to $R_{51}C(O)O$— wherein $R_{51}$ is a hydrogen atom, an alkyl group, an aryl group or an arylheterocyclic ring, as defined herein.

"Carbamoyl" refers to —O—$C(O)N(R_{51})(R_{57})$, wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)O$R_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—$R_{52}$—C(O)—, wherein $R_{55}$ is an aryl group, as defined herein, and $R_{52}$ is an alkyl group, as defined herein.

"Alkylarylcarbonyl" refers to $R_{52}$—$R_{55}$—C(O)—, wherein $R_{55}$ is an aryl group, as defined herein, and $R_{52}$ is an alkyl group, as defined herein.

"Heterocyclicalkylcarbonyl" refer to $R_{78}$C(O)— wherein $R_{78}$ is a heterocyclicalkyl group, as defined herein.

"Carboxylic ester" refers to —C(O)O$R_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

"Silyl" refers to —Si($R_{73}$)($R_{74}$)($R_{75}$), wherein $R_{73}$, $R_{74}$ and $R_{75}$ are each independently a covalent bond, a lower alkyl, an alkoxy, an aryl or an arylalkoxy, as defined herein.

Compounds that donate, transfer or release nitric oxide species in vivo have been recognized as having a wide spectrum of advantages and applications. The present invention is based on the unexpected discovery of the effects of such compounds alone and together with one or more COX-2 inhibitors directly or indirectly linked with one or more nitric oxide moieties. Treatment or prevention of inflammation, pain and fever; treatment and/or improvement of the gastrointestinal properties of COX-2 inhibitors; facilitation of wound healing; and treatment and/or prevention of renal toxicity and cyclooxygenase-2 mediated disorders can be obtained by the use of the nitrosated and/or nitrosylated COX-2 inhibitors of the present invention; or by the use of the nitrosated and/or nitrosylated COX-2 inhibitors in conjunction with one or more compounds that donate, release or transfer nitric oxide and/or stimulate endogenous production of NO and/or EDRF in vivo and/or is a substrate for nitric oxide synthase, and, optionally, with one or more therapeutic agents.

In one embodiment, the present invention describes nitrosated and/or nitrosylated COX-2 inhibitors of Formula (I):

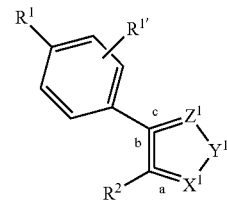

I wherein:
when side b is a double bond, and sides a and c are single bonds, —$X^1$—$Y^1$—$Z^1$— is:
(a) —$CR^4(R^5)$—$CR^5(R^{5'})$—$CR^4(R^5)$—;
(b) —C(O)—$CR^4(R^{4'})$—$CR^5(R^{5'})$—;
(c) —$CR^4(R^{4'})$—$CR^5(R^{5'})$—C(O)—;
(d) —$(CR^5(R^{5'}))_k$—O—C(O)—;
(e) —C(O)—O—$(CR^5(R^{5'}))_k$—;
(f) —$CR^4(R^{4'})$—$NR^3$—$CR^5(R^{5'})$—;
(g) —$CR^5(R^{5'})$—$NR^3$—C(O)—;
(h) —$CR^4$=$CR^{4'}$—S—;
(i) —S—$CR^4$=$CR^{4'}$—;
(j) —S—N=$CR^4$—;
(k) —$CR^4$=N—S—;
(l) —N=$CR^4$—O—;
(m) —O—$CR^4$=N—;
(n) —$NR^3$—$CR^4$=N—;
(o) —N=$CR^4$—S—;
(p) —S—$CR^4$=N—;
(q) —C(O)—$NR^3$—$CR^{5'}(R^{5'})$—;
(r) —$R^3$N—$CR^5$=$CR^{5'}$—;
(s) —$CR^4$=$CR^5$—$NR^3$—;
(t) —O—N=$CR^4$—;
(u) —$CR^4$=N—O—;
(v) —N=N—S—;
(w) —S—N=N—;
(x) —$R^3$N—$CR^4$=N—;
(y) —N=$CR^4$—$NR^3$—;
(z) —$R^3$N—N=N—;
(aa) —N=N—$NR^3$—;
(bb) —$CR^4(R^{4'})$—O—$CR^5(R^{5'})$—;
(cc) —$CR^4(R^{4'})$—S—$CR^5(R^{5'})$—;
(dd) —$CR^4(R^{4'})$—C(O)—$CR^5(R^{5'})$—;
(ee) —$CR^4(R^{4'})$—$CR^5(R^{5'})$—C(S)—;
(ff) —$(CR^5(R^{5'}))_k$—O—C(S)—;
(gg) —C(S)—O—$(CR^5(R^{5'}))_k$—;
(hh) —$(CR^5(R^{5'}))_k$—$NR^3$—C(S)—;
(ii) —C(S)—$NR^3$—$(CR^5(R^{5'}))_k$—;
(jj) —$(CR^5(R^{5'}))_k$—S—C(O)—;
(kk) —C(O)—S—$(CR^5(R^{5'}))_k$—;
(ll) —O—$CR^4$=$CR^5$—;
(mm) —$CR^4$=$CR^5$—O—;
(nn) —C(O)—$NR^3$—S—;

(oo) —S—NR³—C(O)—;
(pp) —C(O)—NR³—O—;
(qq) —O—NR³—C(O)—;
(rr) —NR³—CR⁴=CR⁵—;
(ss) —CR⁴=N—NR³—;
(tt) —NR³—N=CR⁴—;
(uu) —C(O)—NR³—NR³—;
(vv) —NR³—NR³—C(O)—;
(ww) —C(O)—O—NR³—;
(xx) —NR³—O—C(O)—;
(yy) —CR⁴R⁴'—CR⁵R⁵';
(zz) —C(O)—CR⁴R⁴'—
(aaa) —CR⁴R⁴'—C(O)—;
(bbb) —C(S)—CR⁴R⁴'—;
(ccc) —CR⁴R⁴'—C(S)—;
(ddd) —C(=NR³)—CR⁴R⁴'—; or
(eee) —CR⁴R⁴'—C(=NR³)—;

when sides a and c are double bonds and side b is a single bond, —X¹—Y¹—Z¹— is:
(a) =CR⁴—O—CR⁵=;
(b) =CR⁴—NR³—CR⁵=;
(c) =N—S—CR⁴=;
(d) =CR⁴—S—N=;
(e) =N—O—CR⁴=;
(f) =CR⁴—O—N=;
(g) =N—S—N=;
(h) =N—O—N=;
(i) =N—NR³—CR⁴=;
(j) =CR⁴—NR³—N=;
(k) =N—NR³—N=;
(l) =CR⁴—S—CR⁵=; or
(m) =CR⁴—CR⁴(R⁴')—CR⁵=;

R¹ is:
(a) —S(O)₂—CH₃;
(b) —S(O)₂—NR⁸(D¹);
(c) —S(O)₂—N(D¹)—C(O)—CF₃;
(d) —S(O)—(NH)—NH(D¹);
(e) —S(O)—(NH)—N(D¹)—C(O)—CF₃;
(f) —P(O)(CH₃)NH(D¹);
(g) —P(O)(CH₃)₂;
(h) —C(S)—NH(D¹);
(i) —S(O)(NH)CH₃;
(j) —P(O)(CH₃)OD¹; or
(k) —P(O)(CH₃)NH(D¹);

R¹' is:
(a) hydrogen;
(b) halogen;
(c) methyl; or
(d) CH₂OH;

R² is:
(a) lower alkyl;
(b) cycloalkyl;
(c) mono-, di- or tri-substituted phenyl or naphthyl, wherein the substituents are each independently:
(1) hydrogen;
(2) halo;
(3) alkoxy;
(4) alkylthio;
(5) CN;
(6) haloalkyl, preferably CF₃;
(7) lower alkyl;
(8) N₃;
(9) —CO₂D¹;
(10) —CO₂—lower alkyl;
(11) —(C(R⁵)(R⁶))ᵤ—OD¹;
(12) —(C(R⁵)(R⁶))ᵤ—O-lower alkyl;
(13) lower alkyl-CO₂—R⁵;
(14) —OD¹;
(15) haloalkoxy;
(16) amino;
(17) nitro;
(18) alkylsulfinyl; or
(19) heteroaryl;
(d) mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; wherein the substituents are each independently:
(1) hydrogen;
(2) halo;
(3) lower alkyl;
(4) alkoxy;
(5) alkylthio;
(6) CN;
(7) haloalkyl, preferably CF₃;
(8) N₃;
(9) —C(R⁵)(R⁶)—OD¹;
(10) —C(R⁵)(R⁶)—O-lower alkyl; or
(11) alkylsulfinyl;
(e) benzoheteroaryl which includes the benzo fused analogs of (d);
(f) —NR¹⁰R¹¹;
(g) —SR¹¹;
(h) —OR¹¹;
(i) —R¹¹;
(j) alkenyl;
(k) alkynyl;
(l) unsubstituted, mono-, di-, tri- or tetra-substituted cycloalkenyl, wherein the substituents are each independently:
(1) halo;
(2) alkoxy;
(3) alkylthio;
(4) CN;
(5) haloalkyl, preferably CF₃;
(6) lower alkyl;
(7) N₃;
(8) —CO₂D¹;
(9) —CO₂—lower alkyl;
(10) —C(R¹²)(R¹³)—OD¹;
(11) —C(R¹²)(R¹³)—O-lower alkyl;
(12) lower alkyl-CO₂—R¹²;
(13) benzyloxy;
(14) —O—(lower alkyl)—CO₂R¹²;
(15) —O—(lower alkyl)—NR¹²R¹³; or
(16) alkylsulfinyl;
(m) mono-, di-, tri- or tetra-substituted heterocycloalkyl group of 5, 6 or 7 members, or a benzoheterocycle, wherein said heterocycloalkyl or benzoheterocycle contains 1 or 2 heteroatoms selected from O, S, or N and, optionally, contains a carbonyl group or a sulfonyl group, and wherein said substituents are each independently:
(1) halo;
(2) lower alkyl;
(3) alkoxy;
(4) alkylthio;
(5) CN;
(6) haloalkyl, preferably CF₃;
(7) N₃;
(8) —C(R¹²)(R¹³)—OD¹;

(9) —C(R$^{12}$)(R$^{13}$)—O-lower alkyl; or
(10) alkylsulfinyl;
(n) styryl, mono or di-substituted styryl, wherein the substituent are each independently:
  (1) halo;
  (2) alkoxy;
  (3) alkylthio;
  (4) CN;
  (5) haloalkyl, preferably CF$_3$;
  (6) lower alkyl;
  (7) N$_3$;
  (8) —CO$_2$D$^1$;
  (9) —CO$_2$—lower alkyl;
  (10) —C(R$^{12}$)(R$^{13}$)—OD$^1$;
  (11) —C(R$^{12}$)(R$^{13}$)—O-lower alkyl;
  (12) lower alkyl-CO$_2$—R$^{12}$;
  (13) benzyloxy;
  (14) —O-(lower alkyl)-CO$_2$R$^{12}$; or
  (15) —O-(lower alkyl)-NR$^{12}$R$^{13}$;
(o) phenylacetylene, mono- or di-substituted phenylacetylene, wherein the substituents are each independently:
  (1) halo;
  (2) alkoxy;
  (3) alkylthio;
  (4) CN;
  (5) haloalkyl, preferably CF$_3$;
  (6) lower alkyl;
  (7) N$_3$;
  (8) —CO$_2$D$^1$;
  (9) —CO$_2$—lower alkyl;
  (10) —C(R$^{12}$)(R$^{13}$)—OD$^1$;
  (11) —C(R$^{12}$)(R$^{13}$)—O-lower alkyl;
  (12) lower alkyl-CO$_2$—R$^{12}$;
  (13) benzyloxy;
  (14) —O—(lower alkyl)-CO$_2$R$^{12}$; or
  (15) —O—(lower alkyl)-NR$^{12}$R$^{13}$;
(p) fluoroalkenyl;
(q) mono- or di-substituted bicyclic heteroaryl of 8, 9 or 10 members, containing 2, 3, 4 or 5 heteroatoms, wherein at least one heteroatom resides on each ring of said bicyclic heteroaryl, said heteroatoms are each independently O, S and N and said substituents are each independently:
  (1) hydrogen;
  (2) halo;
  (3) lower alkyl;
  (4) alkoxy;
  (5) alkylthio;
  (6) CN;
  (7) haloalkyl, preferably CF$_3$;
  (8) N$_3$;
  (9) —C(R$^5$)(R$^6$)—OD$^1$; or
  (10) —C(R$^5$)(R$^6$)—O-lower alkyl;
(r) K;
(s) aryl;
(t) arylalkyl;
(u) cycloalkylalkyl;
(v) —C(O)R$^{11}$;
(u) hydrogen;
(v) arylalkenyl;
(w) arylalkoxy;
(x) alkoxy;
(y) aryloxy;
(z) cycloalkoxy;
(aa) arylthio;
(bb) alkylthio;
(cc) arylalkylthio; or
(dd) cycloalkylthio;
R$^3$ is:
(a) hydrogen;
(b) haloalkyl, preferably CF$_3$;
(c) CN;
(d) lower alkyl;
(e) —(C(R$_e$)(R$_f$))$_p$—U—V;
(f) K;
(g) unsubstituted or substituted:
  (1) lower alkyl-Q;
  (2) lower alkyl-O-lower alkyl-Q;
  (3) lower alkyl-S-lower alkyl-Q;
  (4) lower alkyl-O—Q;
  (5) lower alkyl-S—Q;
  (6) lower alkyl-O—V;
  (7) lower alkyl-S—V;
  (8) lower alkyl-O—K; or
  (9) lower alkyl-S—K;
wherein the substituent(s) reside on the lower alkyl group;
(h) Q;
(i) alkylcarbonyl;
(j) arylcarbonyl;
(k) alkylarylcarbonyl;
(l) arylalkylcarbonyl;
(m) carboxylic ester;
(n) carboxamido;
(o) cycloalkyl;
(p) mono-, di- or tri-substituted phenyl or naphthyl, wherein the substituents are each independently:
  (1) hydrogen;
  (2) halo;
  (3) alkoxy;
  (4) alkylthio;
  (5) CN;
  (6) haloalkyl, preferably CF$_3$;
  (7) lower alkyl;
  (8) N$_3$;
  (9) —CO$_2$D$^1$;
  (10) —CO$_2$—lower alkyl;
  (11) —(C(R$^5$)(R$^6$))$_z$—OD$^1$;
  (12) —(C(R$^5$)(R$^6$))$_z$—O-lower alkyl;
  (13) lower alkyl-CO$_2$—R$^5$;
  (14) —OD$^1$;
  (15) haloalkoxy;
  (16) amino;
  (17) nitro; or
  (18) alkylsulfinyl;
(q) alkenyl;
(r) alkynyl;
(s) arylalkyl;
(t) lower alkyl-OD$^1$;
(u) alkoxyalkyl;
(v) aminoalkyl;
(w) lower alkyl-CO$_2$R$^{10}$;
(x) lower alkyl-C(O)NR$^{10}$(R$^{10'}$);
(y) heterocyclicalkyl; or
(z) heterocyclic ring-C(O)—;
R$^4$, R$^{4\prime}$, R$^5$ and R$^{5\prime}$ are each independently:
(a) hydrogen;
(b) amino;
(c) CN;
(d) lower alkyl;
(e) haloalkyl;
(f) alkoxy;
(g) alkylthio;
(h) Q;

(i) 13 O—Q;
(j) —S—Q;
(k) K;
(l) cycloalkoxy;
(m) cycloalkylthio;
(n) unsubstituted, mono-, or di-substituted phenyl or unsubstituted, mono-, or di-substituted benzyl, wherein the substituents are each independently:
  (1) halo;
  (2) lower alkyl;
  (3) alkoxy;
  (4) alkylthio;
  (5) CN;
  (6) haloalkyl, preferably $CF_3$;
  (7) $N_3$;
  (8) Q;
  (9) nitro; or
  (10) amino;
(o) unsubstituted, mono-, or di-substituted heteroaryl or unsubstituted, mono-, or di-substituted heteroarylmethyl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; said substituents are each independently:
  (1) halo;
  (2) lower alkyl;
  (3) alkoxy;
  (4) alkylthio;
  (5) CN;
  (6) haloalkyl, preferably $CF_3$;
  (7) $N_3$;
  (8) —C($R^6$)($R^7$)—$OD^1$;
  (9) —C($R^6$)($R^7$)—O-lower alkyl; or
  (10) alkylsulfinyl
(p) —CON($R^8$)($R^8$);
(q) —$CH_2OR^8$;
(r) —$CH_2OCN$;
(s) unsubstituted or substituted:
  (1) lower alkyl-Q;
  (2) —O-lower alkyl-Q;
  (3) —S-lower alkyl-Q;
  (4) lower alkyl-O-lower alkyl-Q;
  (5) lower alkyl-S-lower alkyl-Q;
  (6) lower alkyl-O—Q;
  (7) lower alkyl-S—Q;
  (8) lower alkyl-O—K;
  (9) lower alkyl-S—K;
  (10) lower alkyl-O—V; or
  (11) lower alkyl-S—V;
wherein the substituent(s) resides on the lower alkyl;
  (t) cycloalkyl;
  (u) aryl;
  (v) arylalkyl;
  (w) cycloalkylalkyl;
  (x) aryloxy;
  (y) arylalkoxy;
  (z) arylalkylthio;
  (aa) cycloalkylalkoxy;
  (bb) heterocycloalkyl;
  (cc) alkylsulfonyloxy;
  (dd) alkylsulfonyl;
  (ee) arylsulfonyl;
  (ff) arylsulfonyloxy;
  (gg) —C(O)$R^{10}$;
  (hh) nitro;
  (ii) amino;
  (jj) aminoalkyl;
  (kk) —C(O)-alkyl-heterocyclic ring;
  (ll) halo;
  (mm) heterocyclic ring;
  (nn) —$CO_2D^1$;
  (oo) carboxyl;
  (pp) amidyl; or
  (qq) alkoxyalkyl;
alternatively, $R^4$ and $R^5$ together with the carbons to which they are attached are:
  (a) cycloalkyl;
  (b) aryl; or
  (c) heterocyclic ring;
alternatively, $R^4$ and $R^{4'}$ or $R^5$ and $R^{5'}$ taken together with the carbon to which they are attached are:
  (a) cycloalkyl; or
  (b) heterocyclic ring;
alternatively, $R^4$ and $R^5$, $R^{4'}$ and $R^{5'}$, $R^4$ and $R^{5'}$, or $R^{4'}$ and $R^5$ when substituents on adjacent carbon atoms taken together with the carbons to which they are attached are:
  (a) cycloalkyl;
  (b) heterocyclic ring; or
  (c) aryl;
$R^6$ and $R^7$ are each independently:
  (a) hydrogen;
  (b) unsubstituted, mono- or di-substituted phenyl; unsubstituted, mono- or di-substituted benzyl; unsubstituted, mono- or di-substituted heteroaryl; mono- or di-substituted heteroarylmethyl, wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —C($R^{14}$)($R^{15}$)—$OD^1$; or
    (9) —C($R^{14}$)($R^{15}$)—O-lower alkyl;
  (c) lower alkyl;
  (d) —$CH_2OR^8$;
  (e) CN;
  (f) —$CH_2CN$;
  (g) haloalkyl, preferably fluoroalkyl;
  (h) —CON($R^8$)($R^8$);
  (i) halo; or
  (j) —$OR^8$;
$R^8$ is:
  (a) hydrogen;
  (b) K; or
  (c) $R^9$;
alternatively, $R^5$ and $R^{5'}$, $R^6$ and $R^7$ or $R^7$ and $R^8$ together with the carbon to which they are attached form a saturated monocyclic ring of 3, 4, 5, 6 or 7 atoms; optionally containing up to two heteroatoms selected from oxygen, $S(O)_o$ or $NR_i$;
$R^9$ is:
  (a) lower alkyl;
  (b) lower alkyl-$CO_2D^1$;
  (c) lower alkyl-$NHD^1$;
  (d) phenyl or mono-, di- or tri-substituted phenyl, wherein the substituents are each independently:
    (1) halo;
    (2) lower alkyl;

(3) alkoxy;
(4) alkylthio;
(5) lower alkyl-$CO_2D^1$;
(6) lower alkyl-$NHD^1$;
(7) CN;
(8) $CO_2D^1$; or
(9) haloalkyl, preferably fluoroalkyl;
(e) benzyl, mono-, di- or tri-substituted benzyl, wherein the substituents are each independently:
  (1) halo;
  (2) lower alkyl;
  (3) alkoxy;
  (4) alkylthio;
  (5) lower alkyl-$CO_2D^1$;
  (6) lower alkyl-$NHD^1$;
  (7) CN;
  (8) —$CO_2D^1$; or
  (9) haloalkyl, preferably $CF_3$;
(f) cycloalkyl;
(g) K; or
(h) benzoyl, mono-, di-, or trisubstituted benzoyl, wherein the substituents are each independently:
  (1) halo;
  (2) lower alkyl;
  (3) alkoxy;
  (4) alkylthio;
  (5) lower alkyl-$CO_2D^1$;
  (6) lower alkyl-$NHD^1$;
  (7) CN;
  (8) —$CO_2D^1$; or
  (9) haloalkyl, preferably $CF_3$;
$R^{10}$ and $R^{10\prime}$ are each independently:
  (a) hydrogen; or
  (b) $R^{11}$;
$R^{11}$ is:
  (a) lower alkyl;
  (b) cycloalkyl;
  (c) unsubstituted, mono-, di- or tri-substituted phenyl or naphthyl, wherein the substituents are each independently:
    (1) halo;
    (2) alkoxy;
    (3) alkylthio;
    (4) CN;
    (5) haloalkyl, preferably $CF_3$;
    (6) lower alkyl;
    (7) $N_3$;
    (8) —$CO_2D^1$;
    (9) —$CO_2$—lower alkyl;
    (10) —$C(R^{12})(R^{13})$—$OD^1$;
    (11) —$C(R^{12})(R^{13})$—O-lower alkyl;
    (12) lower alkyl-$CO_2D^1$;
    (13) lower alkyl-$CO_2R^{12}$;
    (14) benzyloxy;
    (15) —O-(lower alkyl)-$CO_2D^1$;
    (16) —O-(lower alkyl)-$CO_2R^{12}$; or
    (17) —O-(lower alkyl)-$NR^{12}R^{13}$;
  (d) unsubstituted, mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or said heteroaryl is a monocyclic ring of 6 atoms, said ring having one heteroatom which is N, and, optionally 1, 2, or 3 additional N atoms, and wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{12})(R^{13})$—$OD^1$; or
    (9) —$C(R^{12})(R^{13})$—O-lower alkyl;
  (e) unsubstituted, mono- or di-substituted benzoheterocycle, wherein the benzoheterocycle is a 5, 6, or 7—membered ring which contains 1 or 2 heteroatoms independently selected from O, S, or N, and, optionally, a carbonyl group or a sulfonyl group, wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{12})(R^{13})$—$OD^1$; or
    (9) —$C(R^{12})(R^{13})$—O-lower alkyl;
  (f) unsubstituted, mono- or di-substituted benzocarbocycle, wherein the carbocycle is a 5, 6, or 7—membered ring which optionally contains a carbonyl group, wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{12})(R^{13})$—$OD^1$; or
    (9) —$C(R^{12})(R^{13})$—O-lower alkyl;
  (g) hydrogen; or
  (h) K
$R^{12}$ and $R^{13}$ are each independently:
  (a) hydrogen;
  (b) lower alkyl; or
  (c) aryl; or
$R^{12}$ and $R^{13}$ together with the atom to which they are attached form a saturated monocyclic ring of 3, 4, 5, 6 or 7 atoms;
$R^{14}$ and $R^{15}$ are each independently:
  (a) hydrogen; or
  (b) lower alkyl; or
$R^{14}$ and $R^{15}$ together with the atom to which they are attached form a carbonyl, a thial, or a saturated monocyclic ring of 3, 4, 5, 6 or 7 atoms;
$D^1$ is:
  (a) hydrogen or
  (b) D;
D is:
  (a) V; or
  (b) K;
U is:
  (a) oxygen;
  (b) sulfur; or
  (c) —$N(R_a)(R_j)$—;
V is:
  (a) —NO;
  (b) —$NO_2$; or
  (c) hydrogen K is —$W_{aa}$—$E_b$—$(C(R_e)(R_f))_p$—$E_c$—$(C(R_e)(R_f))_x$—$W_d$—$(C(R_e)(R_f))_y$—$W_i$—$E_j$—$W_g$—$(C(R_e)(R_f))_z$—U—V; wherein aa, b, c, d, g, i and j are each independently an integer from 0 to 3;

p, x, y and z are each independently an integer from 0 to 10;

W at each occurrence is independently:
- (a) —C(O)—;
- (b) —C(S)—;
- (c) —T—;
- (d) —$(C(R_e)(R_f))_h$—;
- (e) alkyl;
- (f) aryl;
- (g) heterocyclic ring;
- (h) arylheterocyclic ring, or
- (i) —$(CH_2CH_2O)_q$—;

E at each occurrence is independently:
- (a) —T—;
- (b) alkyl;
- (c) aryl;
- (d) —$(C(R_e)(R_f))_h$—;
- (e) heterocyclic ring;
- (f) arylheterocyclic ring; or
- (g) —$(CH_2CH_2O)_q$—;

h is an integer form 1 to 10;
q is an integer from 1 to 5;

$R_e$ and $R_f$ are each independently:
- (a) hydrogen;
- (b) alkyl;
- (c) cycloalkoxy;
- (d) halogen;
- (e) hydroxy;
- (f) hydroxyalkyl;
- (g) alkoxyalkyl;
- (h) arylheterocyclic ring;
- (i) cycloalkylalkyl;
- (j) heterocyclicalkyl;
- (k) alkoxy;
- (l) haloalkoxy;
- (m) amino;
- (n) alkylamino;
- (o) dialkylamino;
- (p) arylamino;
- (q) diarylamino;
- (r) alkylarylamino;
- (s) alkoxyhaloalkyl;
- (t) haloalkoxy;
- (u) sulfonic acid;
- (v) alkylsulfonic acid;
- (w) arylsulfonic acid;
- (x) arylalkoxy;
- (y) alkylthio;
- (z) arylthio;
- (aa) cyano;
- (bb) aminoalkyl;
- (cc) aminoaryl;
- (dd) alkoxy;
- (ee) aryl;
- (ff) arylalkyl;
- (gg) carboxamido;
- (hh) alkylcarboxamido;
- (ii) arylcarboxamido;
- (jj) amidyl;
- (kk) carboxyl;
- (ll) carbamoyl;
- (mm) alkylcarboxylic acid;
- (nn) arylcarboxylic acid;
- (oo) alkylcarbonyl;
- (pp) arylcarbonyl;
- (qq) ester;
- (rr) carboxylic ester;
- (ss) alkylcarboxylic ester;
- (tt) arylcarboxylic ester;
- (uu) haloalkoxy;
- (vv) sulfonamido;
- (ww) alkylsulfonamido;
- (xx) arylsulfonamido;
- (yy) alkylsulfonyl,
- (zz) alkylsulfonyloxy,
- (aaa) arylsulfonyl,
- (bbb) arylsulphonyloxy;
- (ccc) sulfonic ester;
- (ddd) carbamoyl;
- (eee) urea;
- (fff) nitro; or
- (ggg) —U—V; or $R_e$ and $R_f$ taken together are:
- (a) oxo;
- (b) thial; or $R_e$ and $R_f$ taken together with the carbon to which they are attached are:
- (a) heterocyclic ring;
- (b) cycloalkyl group; or
- (c) bridged cycloalkyl group;

k is an integer from 1 to 2;

T at each occurrence is independently:
- (a) a covalent bond,
- (b) carbonyl,
- (c) an oxygen,
- (d) —$S(O)_o$—; or
- (e) —$N(R_a)(R_i)$—;

o is an integer from 0 to 2;

Q is:
- (a) —C(O)—U—$D^1$;
- (b) —$CO_2$-lower alkyl;
- (c) tetrazolyl-5-yl;
- (d) —$C(R^7)(R^8)(S—D^1)$;
- (e) —$C(R^7)(R^8)(O—D^1)$; or
- (f) —$C(R^7)(R^8)$(O-lower alkyl);

$R_a$ is:
- (a) a lone pair of electron;
- (b) hydrogen; or
- (c) lower alkyl;

$R_i$ is:
- (a) hydrogen;
- (b) alkyl;
- (c) aryl;
- (d) alkylcarboxylic acid;
- (e) arylcarboxylic acid;
- (f) alkylcarboxylic ester;
- (g) arylcarboxylic ester;
- (h) alkylcarboxamido;
- (i) arylcarboxamido;
- (j) alkylsulfinyl;
- (k) alkylsulfonyl;
- (l) alkylsulfonyloxy,
- (m) arylsulfinyl;
- (n) arylsulfonyl;
- (o) arylsulphonyloxy;
- (p) sulfonamido;
- (q) carboxamido;
- (r) carboxylic ester;
- (s) aminoalkyl;
- (t) aminoaryl;

(u) —CH$_2$—C(U—V)(R$_e$)(R$_f$);
(v) a bond to an adjacent atom creating a double bond to that atom; or
(w) —(N$_2$O$_2$—)$^-$.M$^+$, wherein M$^+$ is an organic or inorganic cation;
with the proviso that the compounds of Formula I must contain at least one nitrite, nitrate, thionitrite or thionitrate group.

In cases where R$_e$ and R$_f$ are a heterocyclic ring or R$_e$ and R$_f$ taken together with the carbon atoms to which they are attached are a heterocyclic ring, then R$_t$ can be a substituent on any disubstituted nitrogen contained within the radical where R$_t$ is as defined herein.

In cases where multiple designations of variables which reside in sequence are chosen as a "covalent bond" or the integer chosen is 0, the intent is to denote a single covalent bond connecting one radical to another. For example, E$_0$ would denote a covalent bond, while E$_2$ denotes (E—E) and (C(R$_e$)(R$_f$))$_2$ denotes —C(R$_e$)(R$_f$)—C(R$_e$)(R$_f$)—.

Another embodiment of the present invention provides compounds of the Formula (II):

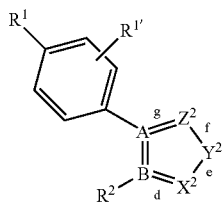

II wherein:
A—B is:
  (a) N—C;
  (b) C—N; or
  (c) N—N;
when sides d and f are double bonds, and sides e and g are single bonds, —X$^2$—Y$^2$—Z$^2$— is:
  (a) =CR$^4$—CR$^{4\prime}$=CR$^5$—;
  (b) =N—CR$^4$=CR$^{4\prime}$—;
  (c) =N—CR$^4$=N—;
  (d) =CR$^4$—N=CR$^{4\prime}$—;
  (e) =CR$^4$—N=N—;
  (f) =N—N=CR$^4$—;
  (g) =N—N=N—;
  (h) =CR$^4$—CR$^5$=N—; or
  (i) =CR$^{2\prime}$—CR$^5$=N—;
R$^2$ and R$^{2\prime}$ taken together are:

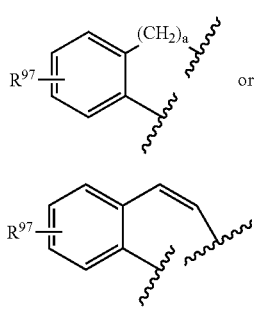

or R$^{2\prime}$ and R$^5$ taken together with the carbon atoms to which they are attached are:
  (a) cycloalkyl; or
  (b) heterocyclic ring;
R$^{97}$ is:
  (a) hydrogen;
  (b) alkylthio;
  (c) alkylsulfinyl;
  (d) alkylsulfonyl;
  (e) cyano;
  (f) carboxyl;
  (g) amino;
  (h) lower alkyl;
  (i) haloalkyl;
  (j) hydroxy;
  (k) alkoxy;
  (l) haloalkoxy;
  (m) alkylarylalkylamino;
  (n) aminoalkyl;
  (o) aminoaryl;
  (p) sulfonamido;
  (q) alkylsulfonamido;
  (r) arylsulfonamido;
  (s) heterocyclic ring;
  (t) hydroxyalkyl; or
  (u) nitro;
a is an integer from 1 to 3;
when sides e and g are double bonds, and sides d and f are single bonds, —X$^2$—Y$^2$—Z$^2$— is:
  (a) —CR$^4$=N—N=;
  (b) —N=N—CR$^4$=;
  (c) —CR$^4$=N—CR$^{4\prime}$=;
  (d) —N=CR$^4$—N=;
  (e) —CR$^4$=CR$^{4\prime}$—N=;
  (f) —N=CR$^4$—CR$^5$=;
  (g) —CR$^4$=CR$^5$—CR$^{5\prime}$=; or
  (h) —N=N—N=;
when side g is a double bond, and sides d, e and f are single bonds, —X$^2$—Y$^2$—Z$^2$— is:
  (a) —C(O)—O—CR$^4$=;
  (b) —C(O)—NR$^3$—CR$^4$=;
  (c) —C(O)—S—CR$^4$=; or
  (d) —C(H)R$^4$—C(OH)R$^5$—N=;
when sides d is a double bond, and sides e, f and g are single bonds, —X$^2$—Y$^2$—Z$^2$— is:
  (a) =CR$^4$—O—C(O)—;
  (b) =CR$^4$—NR$^3$—C(O)—;
  (c) =CR$^4$—S—C(O)—; or
  (d) =N—C(OH)R$^4$—C(H)R$^5$—;
when sides f is a double bond, and sides d, e and g are single bonds, —X$^2$—Y$^2$—Z$^2$— is:
  (a) —CH(R$^4$)—CR$^5$=N—; or
  (b) —C(O)—CR$^4$=CR$^5$—;
when sides e is a double bond, and sides d, f and g are single bonds, —X$^2$—Y$^2$—Z$^2$— is:
  (a) —N=CR$^4$—CH(R$^5$)—; or
  (b) —CR$^4$=CR$^5$—C(O)—;
when sides d, e, f and g are single bonds, —X$^2$—Y$^2$—Z$^2$— is:
  (a) —C(O)—CR$^4$(R$^{4\prime}$)—C(O)—;
R$^1$, R$^{1\prime}$, R$^2$, R$^3$, R$^4$, R$^{4\prime}$, R$^5$ and R$^{5\prime}$ are as defined herein;
with the proviso that the compounds of Formula II must contain at least one nitrite, nitrate, thionitrite or thionitrate group.

Another embodiment of the present invention provides compounds of the Formula (III):

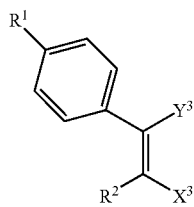

wherein:
$X^3$ is:
   (a) —C(O)—U—$D^1$;
   (b) —$CH_2$—U—$D^1$;
   (c) —$CH_2$—C(O)—$CH_3$;
   (d) —$CH_2$—$CH_2$—C(O)—U—$D^1$;
   (e) —$CH_2$—O—$D^1$; or
   (f) —C(O)H
$Y^3$ is:
   (a) —$(CR^5(R^{5'}))_k$—U—$D^1$;
   (b) —$CH_3$;
   (c) —$CH_2OC(O)R^6$; or (d) —C(O)H;
alternatively, $X^3$ and $Y^3$ taken together are —$CR^{82}(R^{83})$—$CR^{82'}(R^{83'})$—;
$R^{82}$, $R^{82'}$, $R^{83}$ and $R^{83'}$ are each independently:
   (a) hydrogen;
   (b) hydroxy;
   (c) alkyl;
   (d) alkoxy;
   (e) lower alkyl-$OD^1$;
   (f) alkylthio;
   (g) CN;
   (h) —$C(O)R^{84}$; or
   (i) —$OC(O)R^{85}$;
$R^{84}$ is:
   (a) hydrogen;
   (b) lower alkyl; or
   (c) alkoxy;
$R^{85}$ is:
   (a) lower alkyl;
   (b) alkoxy
   (c) unsubstituted, mono-, di- or tri-substituted phenyl or pyridyl, wherein the substituents are each independently:
     (1) halo;
     (2) alkoxy;
     (3) haloalkyl;
     (4) CN;
     (5) —$C(O)R^{84}$;
     (6) lower alkyl;
     (7) —$S(O)_o$-lower alkyl; or
     (8) —$OD^1$;
alternatively, $R^{82}$ and $R^{83}$ or $R^{82'}$ and $R^{83'}$ taken together are:
   (a) oxo;
   (b) thial;
   (c) =$CR^{86}R^{87}$; or
   (d) =$NR^{88}$;
$R^{86}$ and $R^{87}$ are each independently:
   (a) hydrogen;
   (b) lower alkyl;
   (c) lower alkyl-$OD^1$;
   (d) CN; or
   (e) —$C(O)R^{84}$;

$R^{88}$ is:
   (a) $OD^1$;
   (b) alkoxy;
   (c) lower alkyl or
   (d) unsubstituted, mono-, di- or tri-substituted phenyl or pyridyl, wherein the substituents are each independently:
     (1) halo;
     (2) alkoxy;
     (3) haloalkyl;
     (4) CN;
     (5) —$C(O)R^{84}$;
     (6) lower alkyl;
     (7) —$S(O)_o$-lower alkyl; or
     (8) —$OD^1$;
$R^1$, $R^2$, $R^5$, $R^{5'}$, $R^6$, U, $D^1$, o and k are as defined herein;
with the proviso that the compounds of Formula III must contain at least one nitrite, nitrate, thionitrite or thionitrate group.

Another embodiment of the present invention provides compounds of the Formula (IV)

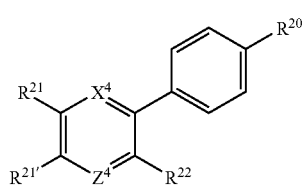

wherein:
$X^4$ and $Z^4$ are each independently:
   (a) N; or
   (b) $CR^{21}$;
$R^{20}$ is:
   (a) —$S(O)_2$—$CH_3$;
   (b) —$S(O)_2$—$NR^8(D^1)$; or
   (c) —$S(O)_2$—$N(D^1)$—C(O)—$CF_3$;
$R^{21}$ and $R^{21'}$ are each independently:
   (a) hydrogen;
   (b) lower alkyl;
   (c) alkoxy;
   (d) alkylthio;
   (e) haloalkyl, preferably fluoroalkyl;
   (f) haloalkoxy, preferably fluoroalkoxy;
   (g) CN;
   (h) —$CO_2D^1$;
   (i) —$CO_2R^{14}$;
   (j) lower alkyl-O—$D^1$;
   (k) lower alkyl—$CO_2D^1$;
   (l) lower alkyl—$CO_2R^{14}$;
   (m) halo;
   (n) —O—$D^1$;
   (o) —$N_3$;
   (p) —$NO_2$;
   (q) —$NR^{14}D^1$;
   (r) —$N(D^1)C(O)R^{14}$;
   (s) —NHK;
   (t) aryl;
   (u) arylalkylthio;
   (v) arylalkoxy;
   (w) alkylamino;
   (x) aryloxy;
   (y) alkylarylalkylamino;

(z) cycloalkylalkylamino; or
(aa) cycloalkylalkoxy;
$R^{22}$ is:
- (a) mono-, di- or tri-substituted phenyl or pyridinyl (or the N-oxide thereof), wherein the substituent are each independently:
  - (1) hydrogen;
  - (2) halo;
  - (3) alkoxy;
  - (4) alkylthio;
  - (5) CN;
  - (6) lower alkyl;
  - (7) haloalkyl, preferably fluoroalkyl;
  - (8) $N_3$;
  - (9) —$CO_2D^1$;
  - (10) —$CO_2$-lower alkyl;
  - (11) —$C(R^{14})(R^{15})$—$OD^1$;
  - (12) —$OD^1$;
  - (13) lower alkyl-$CO_2$—$R^{14}$; or
  - (14) lower alkyl-$CO_2$—$D^1$;
- (b) —T—$C(R^{23})(R^{24})$—$(C(R^{25})(R^{26}))_o$—$C(R^{27})(R^{28})$—U—$D^1$;
- (c)

[structure: N—(CH$_2$)$_s$ / (CH$_2$)$_o$—$Y^5$]

- (d) arylalkyl; or
- (e) cycloalkylalkyl;

wherein:
$R^{14}$ and $R^{15}$ are each independently:
- (a) hydrogen; or
- (b) lower alkyl;

$R^{23}$, $R^{24}$, $R^{25}$, $R^{26}$, $R^{27}R^{28}$ are each independently:
- (a) hydrogen; or
- (b) lower alkyl; or $R^{23}$ and $R^{27}$, or $R^{27}$ and $R^{28}$ together with the atoms to which they are attached form a carbocyclic ring of 3, 4, 5, 6 or 7 atoms, or $R^{23}$ and $R^{25}$ are joined to form a covalent bond;

$Y^5$ is:
- (a) $CR^{29}R^{30}$;
- (b) oxygen; or
- (c) sulfur;

$R^{29}$ and $R^{30}$ are each independently:
- (a) hydrogen;
- (b) lower alkyl;
- (c) $(CH_2)_o$—$OD^1$;
- (d) halo; or $R^{29}$ and $R^{30}$ taken together are an oxo group;
s is an integer from 2 to 4;
$R^8$, $D^1$, T, U, K and o are as defined herein;

with the proviso that the compounds of Formula IV must contain at least one nitrite, nitrate, thionitrite or thionitrate group.

Another embodiment of the present invention provides compounds of the Formula (V):

[Structure V: indole with $R^{31}$ substituent, $CH_3$ at 2-position, N-substituted with $CHR^{38}$—$CR^{39}$ linked to two phenyl groups bearing $R^{40}$, $R^{41}$, $R^{42}$; 3-position bearing —$C(R^{32})(R^{33})$—$(C)_n$—$(CR^{34}R^{35})$—$(CR^{36}R^{37})_n$—C(=$X^5$)—U—K]

wherein:
$X^5$ is:
- (a) oxygen; or
- (b) sulfur;

$R^{31}$ is:
- (a) alkoxy;
- (b) haloalkoxy preferably —$OCH_2F$, —$OCHF_2$, or —$OCHF_2$;
- (c) alkylthio;
- (d) haloalkyl, preferably $CF_3$;
- (e) halo; or
- (f) lower alkyl;

$R^{32}$, $R^{33}$, $R^{34}$, $R^{35}$, $R^{36}$ and $R^{37}$ are each independently:
- (a) hydrogen;
- (b) halo, preferably F or Cl;
- (c) lower alkyl;
- (d) cycloalkyl;
- (e) haloalkyl, preferably $CF_3$, $CF_2H$ or $CFH_2$;
- (f) —$OD^1$;
- (g) —$OR^{43}$;
- (h) —$SD^1$;
- (i) —$SR^{43}$;
- (j) —$S(O)R^{43}$;
- (k) —$S(O)_2R^{43}$;
- (l) unsubstituted, mono- or di-substituted benzyl, wherein the substituents are each independently:
  - (1) haloalkyl, preferably $CF_3$;
  - (2) CN;
  - (3) halo;
  - (4) lower alkyl;
  - (5) —$OR^{43}$;
  - (6) —$SR^{43}$;
  - (7) —$S(O)R^{43}$; or
  - (8) —$S(O)_2R^{41}$;
- (m) phenyl or mono- or di-substituted phenyl, wherein the substituents are each independently:
  - (1) haloalkyl, preferably $CF_3$;
  - (2) CN;
  - (3) halo;
  - (4) lower alkyl;
  - (5) —$OR^{43}$;
  - (6) —$SR^{43}$;
  - (7) —$S(O)R^{43}$; or
  - (8) —$S(O)_2R^{41}$; or $R^{32}$ together with $R^{33}$ form an oxo group; or
$R^{34}$ together with $R^{35}$ form an oxo group; or
$R^{36}$ together with $R^{37}$ form an oxo group; or
$R^{32}$ and $R^{33}$ are joined so that, together with the carbon atom to which they are attached, they form a saturated monocyclic ring of 3, 4, 5, 6 or 7 members, and, optionally, contain one heteroatom which is preferably oxygen; or $R^{33}$ and $R^{34}$ are joined so that, together with the carbon atoms to which they are attached, they form a saturated or aromatic monocyclic ring of 3, 4, 5, 6 or 7 members; or $R^{33}$ and $R^{36}$ are joined so that, together with the carbon atoms to which they are attached, they form a saturated or aromatic monocyclic ring of 3, 4, 5, 6 or 7 members; or $R^{34}$ and $R^{35}$ are joined so that, together with the carbon atom to which they are attached, they form a saturated monocyclic ring of 3, 4, 5, 6 or 7 members, and optionally, contain one heteroatom which is preferably oxygen; or $R^{34}$ and $R^{36}$ are joined so that, together with the carbon atoms to which they are attached, they form a saturated or aromatic monocyclic ring of 3, 4, 5, 6 or 7 members; or $R^{36}$ and $R^{37}$ are joined so that, together with the carbon atom to which they are attached, they form a saturated monocyclic ring of 3, 4, 5, 6 or 7 members, and, optionally, contain one heteroatom which is preferably oxygen;

$R^{38}$ and $R^{39}$ are hydrogen or $R^{38}$ and $R^{39}$ when taken together are oxo;

$R^{40}$, $R^{41}$ and $R^{42}$ are each independently:
  (a) hydrogen;
  (b) halo;
  (c) lower alkyl;
  (d) alkoxy;
  (e) alkylthio;
  (f) —S(O)-lower alkyl;
  (g) haloalkyl, preferably $CF_3$;
  (h) CN;
  (i) —$N_3$;
  (j) —$NO_2$;
  (k) —$SCF_3$; or
  (l) —$OCF_3$;

$R^{43}$ is:
  (a) lower alkyl; or
  (b) benzyl, optionally mono- or di-substituted, wherein the substituents are each independently:
    (1) haloalkyl, preferably $CF_3$;
    (2) CN;
    (3) halo; or
    (4) lower alkyl;

alternatively, $X^5$ and U taken together with the carbon atom to which they are attached form a 5-, 6-, or 7-membered heterocyclic ring;

n at each occurrence is an integer from 0 to 1; and $D^1$, U and K are as defined herein;

with the proviso that the compounds of Formula V must contain at least one nitrite, nitrate, thionitrite or thionitrate group.

Another embodiment of the present invention provides compounds of the Formula (VI):

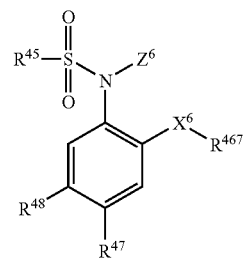

VI wherein:
$X^6$ is:
  (a) oxygen;
  (b) sulfur;
  (c) $CH_2$;
  (d) —$S(O)_o$;
  (e) —NH; or
  (f) —C(O);

$Z^6$ is:
  (a) K;
  (b) —$C(O)CH_3$; or
  (c) hydrogen;

$R^{45}$ is:
  (a) lower alkyl; or
  (b) mono-, di-, tri-, tetra- or per-substituted lower alkyl, wherein the substituent is halo, preferably fluoro;

$R^{46}$ is:
  (a) mono or disubstituted aromatic ring of 5 atoms containing one O, S or N atom, and, optionally, 1, 2 or 3 additional N atoms, wherein the substituents are each independently:
    (1) hydrogen;
    (2) lower alkyl;
    (3) halo;
    (4) —O-lower alkyl;
    (5) —S-lower alkyl;
    (6) haloalkyl, preferably $CF_3$;
    (7) —$COCH_3$; or
    (8) —$S(O)_2$-lower alkyl;
  (b) mono or disubstituted aromatic ring of 6 atoms containing 0, 1, 2, 3 or 4 nitrogen atoms, wherein the substituents are each independently:
    (1) hydrogen;
    (2) lower alkyl;
    (3) halo;
    (4) —O-lower alkyl;
    (5) —S-lower alkyl;
    (4) —O-haloalkyl;
    (5) —S-haloalkyl;
    (6) haloalkyl, preferably $CF_3$;
    (7) CN;
    (8) —$N_3$;
    (9) —$COCH_3$;
    (10) —$S(O)_2$-lower alkyl;
    (11) alkenyl; or
    (12) alkynyl;
  (c) cycloalkylalkyl;
  (d) unsubstituted, mono-, di-, tri-, or tetra substituted phenyl or naphthyl, wherein the substituents are each independently:
    (1) halo;
    (2) CN;

(3) haloalkyl, preferably $CF_3$;
(4) —$N_3$;
(5) vinyl;
(6) acetylenyl;
(7) lower alkyl;
(8) alkoxy;
(9) haloalkoxy;
(10) alkylthio; or
(11) haloalkylthio;
(e) unsubstituted, mono-, di-, tri-, or tetra substituted benzoheteroaryl, wherein the substituents are each independently:
(1) halo;
(2) CN; or
(3) haloalkyl, preferably $CF_3$;
(f) substituted lower alkyl;
(g) substituted alkenyl;
(h) cycloalkyl; or
(i) lower alkyl-O-lower alkyl;
$R^{47}$ is:
(a) —C(O)-lower alkyl;
(b) —CN;
(c) —$CO_2D^1$;
(d) —$CO_2$-lower alkyl ester;
(e) —C(O)—$NHD^1$;
(f) —S(O)-lower alkyl;
(g) —$S(O)_2$-lower alkyl;
(h) —$NO_2$;
(i) haloalkyl, preferably $CF_3$;
(j) halo;
(k) K;
(l) —$S(O)_oNR^{10}R^{11}$; or
(m) —$S(O)_oNR^{12}R^{13}$;
$R^{48}$ is:
(a) hydrogen; or
(b) lower alkyl; or
$R^{47}$ and $R^{48}$ taken together with the atoms to which they are attached form a 5, 6, or 7-membered unsubstituted, mono-, di-, or trisubstituted saturated or unsaturated cyclic ring optionally containing a —$S(O)_2$-group, wherein the substituents are each independently:
(a) oxo;
(b) lower alkyl;
(c) $OD^1$; or
(d) =N—$OD^1$;
$R^{10}$, $R^{11}$, $R^{12}$, $R^{13}$, K, $D^1$ and o are as defined herein;
with the proviso that the compounds of Formula VI must contain at least one nitrite, nitrate, thionitrite or thionitrate group.

Another embodiment of the present invention provides compounds of Formula (VII):

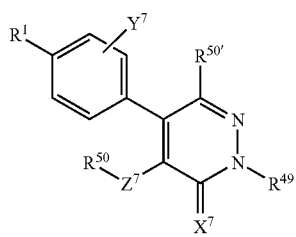

VII wherein:
$X^7$ is:
(a) oxygen;
(b) sulfur;
(c) —$NR^{51}$;
(d) —N—O—$R^{52}$; or
(e) —N—$NR^{52}R^{53}$;
$Y^7$ is:
(a) hydrogen;
(b) halo;
(c) lower alkyl;
(d) alkenyl; or
(e) alkynyl;
$Z^7$ is:
(a) —C(O)—;
(b) oxygen;
(c) —$S(O)_o$—;
(d) —$NR^{93}$—; or
(e) covalent bond;
$R^{49}$ is:
(a) $R^3$; or
(b) $R^4$;
$R^{50}$ and $R^{50'}$ are each independently:
(a) hydrogen;
(b) halo;
(c) lower alkyl;
(d) aryl;
(e) arylalkyl;
(f) cycloalkyl;
(g) cycloalkylalkyl;
(h) —$OD^1$;
(i) lower alkyl-$OD^1$;
(j) carboxamido;
(k) amidyl; or
(l) K;
$R^{51}$ is:
(a) lower alkyl;
(b) alkenyl;
(c) cycloalkyl;
(d) cycloalkylalkyl;
(e) aryl;
(f) arylalkyl;
(g) heterocyclic ring; or
(h) lower alkyl-heterocyclic ring;
$R^{52}$ and $R^{53}$ are each independently:
(a) lower alkyl;
(b) cycloalkyl;
(c) cycloalkylalkyl;
(d) aryl;
(e) arylalkyl;
(f) heterocyclic ring; or
(g) heterocyclicalkyl;
$R^{93}$ is:
(a) hydrogen; or
(b) lower alkyl;
$R^1$, $R^3$, $R^4$, K, $D^1$ and o are as defined herein;
with the proviso that the compounds of Formula VII must contain at least one nitrite, nitrate, thionitrite or thionitrate group.

Another embodiment of the present invention provides compounds of the Formula (VIII):

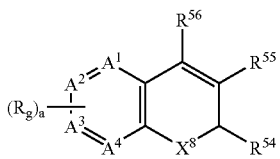

wherein:

X⁸ is:
(a) oxygen;
(b) sulfur;
(c) NR$_i$; or
(d) —CR⁵⁸R⁵⁹;

A¹, A², A³, and A⁴ are each independently carbon or nitrogen, with the proviso that at least two of A¹, A², A³, and A⁴ are carbon atoms;

R⁵⁴ is:
(a) haloalkylalkyl, preferably fluoroalkylalkyl;
(b) halo;
(c) alkylthio;
(d) alkoxy;
(e) —NO₂;
(f) CN;
(g) lower alkyl-CN;
(h) heterocyclic ring;
(i) lower alkyl;
(j) arylalkyl;
(k) cycloalkyl; or
(l) phenyl or mono- or di-substituted phenyl, wherein the substituents are each independently:
  (1) alkylthio;
  (2) nitro; or
  (3) alkylsulfonyl;

R⁵⁵ is:
(a) —CO₂D¹;
(b) —C(O)—N (R⁸)(R⁸);
(c) —CO₂-lower alkyl;
(d) —C(O)—N(D¹)—S(O)₂—(C(R$_e$)(R$_f$))$_p$—U—V; or
(e) —CO₂-lower alkyl-U—V;

R⁵⁶ is:
(a) hydrogen;
(b) phenyl;
(c) thienyl;
(d) alkynyl;
(e) alkenyl; or
(f) alkyl;

R$_g$ is:
(a) hydrogen;
(b) lower alkyl;
(c) arylalkyl;
(d) alkoxy;
(e) aryloxy;
(f) arylalkoxy;
(g) haloalkyl;
(h) haloalkoxy;
(i) alkylamino;
(j) arylamino;
(k) arylalkylamino;
(l) nitro;
(m) sulfonamido;
(n) carboxamido;
(o) aryl;
(p) —C(O)-aryl; or
(q) —C(O)-alkyl;

alternatively, R$_g$ and the monocyclic ring radical of which A¹, A², A³, and A⁴ comprise four of the six atoms are:
(a) naphthyl;
(b) quinolyl;
(c) isoquinolyl;
(d) quinolizinyl;
(e) quinoxalinyl; or
(f) dibenzofuryl;

R⁵⁸ and R⁵⁹ are each independently:
(a) hydrogen;
(b) lower alkyl;
(c) lower alkyl-phenyl;
(d) haloalkyl, preferably fluoroalkyl;
(e) halo;
(f) —NO₂;
(g) CN;
(h) lower alkyl-CN;
(i) alkoxy;
(j) alkylthio; or
(k) alkenyl;

alternatively, R⁵⁸ and R⁵⁹ taken together along with the atoms to which they are attached are cycloalkyl;

R⁸, R$_i$, R$_e$, R$_f$, D¹, U, V, a and p are as defined herein;

with the proviso that the compounds of Formula VIII must contain at least one nitrite, nitrate, thionitrite or thionitrate group.

Another embodiment of the present invention provides compounds of the Formula (IX):

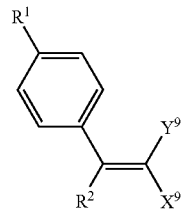

wherein:

X⁹ is —C(O)—U—D¹ and Y⁹ is —CH₂—CR⁵(R⁵')—U—D¹'; or

X⁹ is —CH₂—CR⁵(R⁵')—U—D¹ and Y⁹ is —C(O)—U—D¹; or

X⁹ and Y⁹ taken together are:
(a) —C(O)—O—CR⁴(R⁴')—CR⁵(R⁵')—;
(b) —(CR⁴(R⁴'))$_k$—CR⁵(R⁵')—CR⁵(R⁵)—;
(c) —C(O)—(CR⁴(R⁴'))$_k$—CR⁵(R⁵')—;
(d) —(CR⁴(R⁴'))$_k$—CR⁵(R⁵')—C(O)—; or
(e) —C(O)—CR⁴(R⁴')—CR⁵(R⁵')—;

wherein X⁹ is the first carbon atom of a, b, c, d and e;

R¹, R², R⁴, R⁴', R⁵, R⁵', U, D¹ and k are as defined herein;

with the proviso that the compounds of Formula IX contain at least one nitrite, nitrate, thionitrite or thionitrate group.

Another embodiment of the present invention provides compounds of the Formula (X):

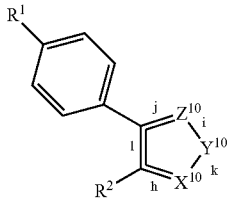

wherein:
when side h, k, and j are single bonds, and side i and l are a double bond, —$X^{10}$—$Y^{10}$—$Z^{10}$— is:

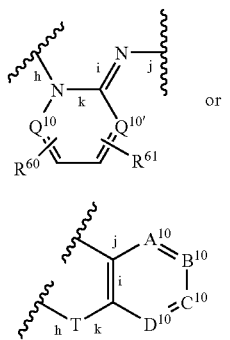

(a)

or (b)

when sides i, k and l are single bonds, and sides h and j are double bonds, —$X^{10}$—$Y^{10}$—$Z^{10}$— is:

when side h and j are single bonds, and side k and i is a single or a double bond, —$X^{10}$—$Y^{10}$—$Z^{10}$— is:

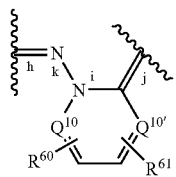

(a)

or

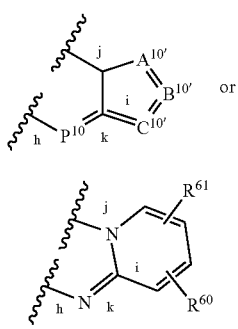

(b)

$P^{10}$ is:
(a) —N=;
(b) —$NR^3$—;
(c) —O—; or
(d) —S—;

$Q^{10}$ and $Q^{10'}$ are each independently:
(a) $CR^{60}$; or
(b) nitrogen;

—$A^{10}$····$B^{10}$—$C^{10}$····$D^{10}$— is:
(a) —$CR^4$=$CR^{4'}$—$CR^5$=$CR^{5'}$—;
(b) —$CR^4(R^{4'})$—$CR^5(R^{5'})$—$CR^4(R^{4'})$—C(O)—;
(c) —$CR^4(R^{4'})$—$CR^5(R^{5'})$—C(O)—$CR^4(R_{4'})$—;
(d) —$CR^4(R^{4'})$—C(O)—$CR^4(R^{4'})$—$CR^5(R^{5'})$—;
(e) —C(O)—$CR^4(R^{4'})$—$CR^5(R^{5'})$—$CR^4(R^{4'})$—;
(f) —$CR^4(R^{4'})$—$CR^5(R^{5'})$—C(O)—;
(g) —$CR^4(R^{4'})$—C(O)—$CR^5(R^{5'})$—;
(h) —C(O)—$CR^4(R^{4'})$—$CR^5(R^{5'})$—;
(i) —$CR^4(R^{4'})$—$CR^5(R^{5'})$—O—C(O)—;
(j) —$CR^4(R^{4'})$—O—C(O)—$CR^5(R^{5'})$—;
(k) —O—C(O)—$CR^4(R^{4'})$—$CR^5(R^{5'})$—;
(l) —$CR^4(R^{4'})$—$CR^5(R^{5'})$—C(O)—O—;
(m) —$CR^4(R^{4'})$—C(O)—O—$CR^5(R^{5'})$—;
(n) —C(O)—O—$CR^4(R^{4'})$—$CR^5(R^{5'})$—;
(o) —$CR^{12}(R^{13})$—O—C(O)—;
(p) —C(O)—O—$CR^{12}(R^{13})$—;
(q) —O—C(O)—$CR^{12}(R^{13})$—;
(r) —$CR^{12}(R^{13})$—C(O)—O—;
(s) —N=$CR^4CR^{4'}$=$CR^5$—;
(t) —$CR^4$=N—$CR^{4'}$=$CR^5$—;
(u) —$CR^4$=$CR^{4'}$—N=$CR^5$—;
(v) —$CR^4$=$CR^5$—$CR^{5'}$=N—;
(w) —N=$CR^4CR^{4'}$=N—;
(x) —N=$CR^4$—N=$CR^{4'}$—;
(y) —$CR^4$=N—$CR^{4'}$=N—;
(z) —S—$CR^4$=N—;
(aa) —S—N=$CR^4$—;
(bb) —N=N—$NR^3$—;
(cc) —$CR^4$=N—S—;
(dd) —N=$CR^4$—S—;
(ee) —O—$CR^4$=N—;
(ff) —O—N=$CR^4$—; or
(gg) —N=$CR^4$—O—;

—$A^{10'}$····$B^{10'}$····$D^{10'}$···· is:
(a) —$CR^4$=$CR^5$—$CR^{5'}$=
(b) —$CR^4(R^{4'})$—$CR^5(R^{5'})$—$CR^4(R^{4'})$—;
(c) —C(O)—$CR^4(R^{4'})$—$CR^5(R^{5'})$—;
(d) —$CR^4(R^{4'})$—$CR^5(R^{5'})$—C(O)—;
(e) —N=$CR^4$—$CR^5$=;
(g) —N=N—$CR^4$=;
(h) —N=N—$NR^3$—;
(i) —N=N—N=;
(j) —N=$CR^4$—$NR^3$—;
(k) —N=$CR^4$—N=;
(l) —$CR^4$=N—$NR^3$—;
(m) —$CR^4$=N—N=;
(n) —$CR^4$=N—$CR^5$=;
(o) —$CR^4$=$CR^5$—$NR^3$—;
(p) —$CR^4$=$CR^5$—N=;
(q) —S—$CR^4$=$CR^5$—;
(r) —O—$CR^4$=$CR^5$;
(s) —$CR^4$=$CR^5$—O—;
(t) —$CR^4$=$CR^5$—S—;
(u) —$CR^4$=N—S—;
(v) —$CR^4$=N—O—;
(w) —N=$CR^4$—S—;
(x) —N=$CR^4$—O—;
(y) —S—$CR^4$=N—;
(z) —O—$CR^4$=N—;
(aa) —N=N—S—;
(bb) —N=N—O—;
(cc) —S—N=N—;

(dd) —O—N=N—;
(ee) —CR$^4$=CR$^5$—S—;
(ff) —CR$^4$(R$^{4'}$)—CR$^5$(R$^{5'}$)—S—;
(gg) —CR$^4$(R$^{4'}$)—CR$^5$(R$^{5'}$)—O—;
(hh) —S—CR$^4$(R$^{4'}$)—CR$^5$(R$^{5'}$)—; or
(ii) —O—CR$^4$(R$^{4'}$)—CR$^5$(R$^{5'}$)—;

R$^{60}$ and R$^{61}$ are each independently:
(a) lower alkyl;
(b) haloalkyl, preferably fluoroalkyl;
(c) alkoxy;
(d) alkylthio;
(e) lower alkyl-OD$^1$;
(f) —C(O)H;
(h) —(CH$_2$)$_q$—CO$_2$-lower alkyl;
(i) —(CH$_2$)$_q$—CO$_2$D$^1$;
(j) —O—(CH$_2$)$_q$—S-lower alkyl;
(k) —(CH$_2$)$_q$—S-lower alkyl;
(l) —S(O)$_2$-lower alkyl;
(m) —(CH$_2$)$_q$—NR$^{12}$R$^{13}$; or
(n) —C(O)N(R$^8$)(R$^8$);

R$^1$, R$^2$, R$^3$, R$^4$, R$^{4'}$, R$^5$, R$^{5'}$, R$^8$, R$^{12}$, R$^{13}$, T, D$^1$ and q are as defined herein;

with the proviso that the compounds of Formula X must contain at least one nitrite, nitrate, thionitrite or thionitrate group.

Another embodiment of the present invention provides compounds of the Formula (XI):

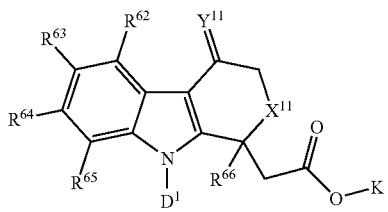

XI wherein:
X$^{11}$ is:
(a) oxygen; or
(b) CH$_2$;
Y$^{11}$ is:
(a) oxygen;
(b) —H$_2$;
(c) —N—OD$^1$;
(d) —N—O-lower alkyl;
(e) —N—O-aryl;
(f) —N—C(O)—O-lower alkyl;
(g) —N—N(R$^8$)(R$^8$); or
(h) —N—N(R$^8$)—S(O)$_2$-lower alkyl;

R$^{62}$, R$^{63}$, R$^{64}$ and R$^{65}$ are each independently:
(a) hydrogen;
(b) lower alkyl;
(c) alkoxy;
(d) halo;
(e) CN;
(f) OD$^1$;
(g) aryloxy;
(h) —NR$^{12}$R$^{13}$;
(i) —CF$_3$;
(j) —NO$_2$;
(k) alkylthio;
(l) —S(O)$_o$-lower alkyl;
(m) —C(O)N(R$^8$)(R$^8$);
(n) —CO$_2$D$^1$
(o) —CO$_2$-lower alkyl; or
(p) —NR$^8$—C(O)-lower alkyl;

R$^{66}$ is:
(a) hydrogen;
(b) lower alkyl;
(c) alkenyl;
(d) alkoxyalkyl; or
(e) cycloalkylalkyl;

R$^8$, R$^{12}$, R$^{13}$, o, K and D$^1$ are as defined herein;

with the proviso that the compounds of Formula XI must contain at least one nitrite, nitrate, thionitrite or thionitrate group.

Another embodiment of the present invention provides compounds of the Formula (XII):

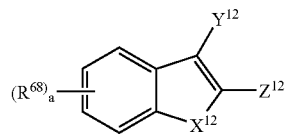

XII wherein:
X$^{12}$ is:

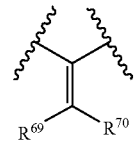

(a)

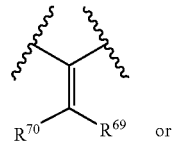

(b)

NR$^{71}$;

(c)

Y$^{12}$ is:

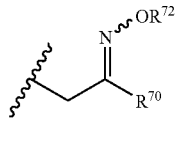

(a)

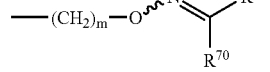

(b)

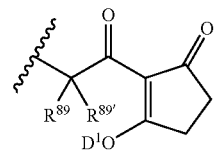

(c)

-continued (d) 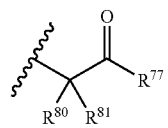

(e) —NR$^{73}$(R$^{74}$);
(f) hydrogen; or
(g) K;

Z$^{12}$ is:

(a) 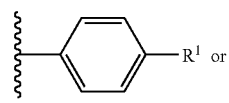

(b) R$^{67}$;

R$^{67}$ is:
(a) hydrogen;
(b) lower alkyl;
(c) lower alkyl-OD$^1$;
(d) —OD$^1$;
(e) haloalkyl; or
(f) 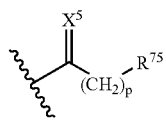

R$^{68}$ is:
(a) lower alkyl;
(b) halo;
(c) alkoxy
(d) haloalkyl;
(e) alkylthio;
(f) haloalkylthio;
(g) —OCH$_2$—
(h) unsubstituted, mono-, or di-substituted heteroaryl, wherein the heteroaryl is a monocyclic aromatic ring of 5 atoms, said ring having one heteroatom which is S, O, or N, and, optionally, 1, 2, or 3 additional N atoms; or said heteroaryl is a monocyclic ring of 6 atoms, said ring having one heteroatom which is N, and, optionally 1, 2, or 3 additional N atoms, and wherein said substituents are each independently:
(1) halo; or
(2) lower alkyl
(i) —S(O)$_o$-lower alkyl;
(j) —S(O)$_o$-lower haloalkyl;
(k) amino;
(l) alkylamino;
(m) dialkylamino;
(n) —N(H)SO$_2$-lower alkyl;
(o) N(H)SO$_2$-lower haloalkyl;
(p) nitro;
(q) cyano;
(r) —CO$_2$D$^1$;
(s) carboxylic ester;
(t) lower alkyl-OD$^1$;
(q) carboxamide; or
(r) —C(O)N(R$^{12}$)D$^1$;

R$^{69}$ is:
(a) lower alkyl;
(b) hydrogen;
(c) alkoxy
(d) mono-, di-, tri, tetra- or penta-substituted phenyl, wherein the substituent are each independently:
(1) hydrogen;
(2) halo;
(3) alkoxy;
(4) alkylthio;
(5) —S(O)$_o$-lower alkyl;
(6) lower alkyl;
(7) haloalkyl;
(8) —CO$_2$D$^1$;
(9) -lower alkyl—CO$_2$D$^1$;
(10) —OD$^1$;
(11) -lower alkyl-OD$^1$; or
(12) haloalkoxy;
(e) mono-, di-, or tri-substituted heteroaryl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms; said ring having one heteroatom which is N, and, optionally, 1, 2, 3, or 4 additional N atoms; wherein the substituents are each independently:
(1) hydrogen;
(2) halo;
(3) lower alkyl;
(4) alkoxy;
(5) alkylthio;
(6) aryloxy;
(7) arylthio;
(8) —CO$_2$D$^1$;
(9) —C(O)NH(D$^1$)
(10) haloalkyl; or
(11) —OD$^1$;

R$^{70}$ is:
(a) lower alkyl;
(b) hydrogen; or
(c) mono- or di-substituted phenyl, wherein the substituent are each independently:
(1) hydrogen;
(2) halo;
(3) alkoxy;
(4) haloalkyl; or
(5) lower alkyl;

R$^{71}$ is:
(a) benzoyl, or mono-, or disubstituted benzoyl, wherein the substituents are each independently:
(1) halo;
(2) lower alkyl; or
(3) alkoxy;
(b) benzyl, mono- or disubstituted benzyl, wherein the substituents are each independently:
(1) halo;
(2) lower alkyl; or
(3) alkoxy;
(c) lower alkyl-pyridinyl, or unsubstituted, mono-, or disubstituted pyridinyl, wherein the substituents are each independently:
(1) halo;
(2) lower alkyl; or
(3) alkoxy;

(d) —C(O)-pyridinyl, or mono-, or disubstituted —C(O)-pyridinyl wherein the substituents are each independently:
  (1) halo;
  (2) lower alkyl; or
  (3) alkoxy;
(e) hydrogen;
(f) aryl;
(g) cycloalkyl;
(h) cycloalkylalkyl;
$R^{72}$ is:
  (a) lower alkenyl-$CO_2D^1$; or
  (b) K;
$R^{73}$ is unsubstituted or mono substituted lower alkyl, wherein the substituents are each independently:
  (a) hydroxy;
  (b) alkoxy;
  (c) nitro;
  (c) —$NH_2$;
  (d) alkylamino;
  (e) dialkylamino;
  (f) carboxyl;
  (g) carboxylic ester; or
  (h) carboxamide;
$R^{74}$ is:
  (a) hydrogen;
  (b) lower alkyl; or
  (c) —C(O)$R^{76}$;
$R^{75}$ is:
  (a) lower alkyl;
  (b) haloalkyl
  (c) substituted lower alkyl;
  (d) cycloalkyl;
  (e) unsubstituted, mono-, di- or tri-substituted phenyl or naphthyl, wherein the substituents are each independently:
    (1) halo;
    (2) alkoxy;
    (3) —S(O)$_o$-lower alkyl;
    (4) hydroxy;
    (5) —S(O)$_o$-haloalkyl;
    (6) lower alkyl;
    (7) haloalkyl;
    (8) —$CO_2D^1$;
    (9) —$CO_2$-lower alkyl;
    (10) —S(O)$_2$$NR^8(D^1)$;
    (11) -lower alkyl-O-lower alkyl;
    (12) —CN;
    (13) lower alkyl-$OD^1$;
    (14) arylalkoxy;
    (15) —C(O)$NR^8(D^1)$; or
    (16) aryl;
  (f) mono-, di- or tri-substituted heteroaryl, wherein the heteroaryl is a monocyclic aromatic ring of 5 atoms, said ring having one heteroatom which is selected from S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; wherein the substituents are each independently:
    (1) halo;
    (2) alkoxy;
    (3) —S(O)$_o$-lower alkyl;
    (4) hydroxy;
    (5) —S(O)$_o$-haloalkyl;
    (6) lower alkyl;
    (7) haloalkyl;
    (8) —$CO_2D^1$;
    (9) —$CO_2$-lower alkyl;
    (10) —S(O)$_2$$NR^8(D^1)$;
    (11) -lower alkyl-O-lower alkyl;
    (12) —$N(D^1)S(O)_2$-lower alkyl;
    (13) lower alkyl-$OD^1$;
    (14) —$N(D^1)S(O)_2$-haloalkyl;
    (15) —C(O)$NR^8(D^1)$; or
    (16) aryl;
$R^{76}$ is:
  (a) alkyl;
  (b) substituted alkyl;
  (c) alkyl-$N(D^1)S(O)_2$-aryl;
  (d) substituted alkyl-cycloalkyl;
  (e) substituted alkyl-heterocyclic ring; or
  (f) arylalkoxy;
R77 is:
  (a) —$OD^1$;
  (b) alkoxy; or
  (c) —$NR^{78}R^{79}$;
$R^{78}$ and $R^{79}$ are each independently:
  (a) hydrogen;
  (b) hydroxy;
  (c) alkoxy;
  (d) lower alkyl; or
  (e) substituted lower alkyl; or
$R^{78}$ and $R^{79}$ taken together with the nitrogen to which they are attached form a heterocyclic ring;
$R^{80}$ and $R^{81}$ are each independently:
  (a) hydrogen;
  (b) lower alkyl; or
  (c) halo;
$R^{89}$ and $R^{89'}$ are each independently:
  (a) hydrogen; or
  (b) lower alkyl; or
$R^{89}$ and $R^{89'}$ taken together with the carbon to which they are attached form a cycloalkyl ring;
m is an integer from 0 to 6;
$D^1$, $R^1$, $R^8$, $R^{12}$, K, $X^5$, a, p and o are as defined herein; and
with the proviso that the compounds of Formula XII must contain at least one nitrite, nitrate, thionitrite or thionitrate group.

Another embodiment of the present invention provides compounds of the Formula (XIII):

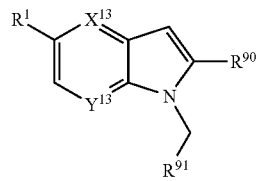

XIII wherein:
$X^{13}$ and $Y^{13}$ are each independently:
  (a) =C(H)—; or
  (b) =N—;
$R^{90}$ is:
  (a) lower alkyl;
  (b) lower alkyl-$OD^1$;
  (c) alkenyl;
  (d) lower alkyl-CN;
  (e) lower alkyl-$CO_2D^1$;

(f) aryl;
(g) heterocyclic ring; or
(i) heterocyclicalkyl;
$R^{91}$ is:
(a) mono-, di- or tri-substituted phenyl, wherein the substituents are each independently:
(1) hydrogen;
(2) halo;
(3) alkoxy;
(4) alkylthio;
(5) CN;
(6) haloalkyl;
(7) lower alkyl;
(8) —$CO_2D^1$;
(9) —$CO_2$-lower alkyl;
(10) lower alkyl-$OD^1$;
(11) lower alkyl-$NR^{12}R^{13}$;
(12) lower alkyl-$CO_2D^1$; or
(13) —$OD^1$;
(b) mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; wherein the substituents are each independently:
(1) hydrogen;
(2) halo;
(3) alkoxy;
(4) alkylthio;
(5) CN;
(6) haloalkyl;
(7) lower alkyl;
(8) —$CO_2D^1$;
(9) —$CO_2$-lower alkyl;
(10) lower alkyl-$OD^1$;
(11) lower alkyl-$NR^{12}R^{13}$;
(12) lower alkyl-$CO_2D^1$; or
(13) —$OD^1$;
$D^1$, $R^1$, $R^{12}$, and $R^{13}$, are as defined herein; and
with the proviso that the compounds of Formula XIII must contain at least one nitrite, nitrate, thionitrite or thionitrate group.

Another embodiment of the present invention provides compounds of the Formula (XIV):

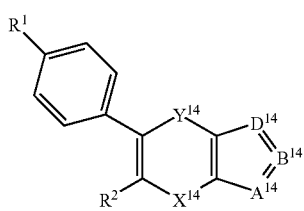

XIV wherein:
$X^{14}$ is:
(a) —C(O)—; or
(b) —C(S)—;
$Y^{14}$ is:
(a) —O—; or
(b) —S—;

$A^{14}\cdots B^{14}\cdots D^{14}$ is:
(a) —$CR^4$=$CR^{4'}$—$CR^5$=$CR^{5'}$—;
(b) —$CR^4(R^{4'})$—$CR^5(R^{5'})$—C(O)—;
(c) —$CR^4(R^{4'})$—C(O)—$CR^5(R^{5'})$—;
(d) —C(O)—$CR^4(R^{4'})$—$CR^5(R^{5'})$—;
(e) —$CR^4(R^5)$—O—C(O)—;
(f) —C(O)—O—$CR^4(R^5)$—;
(g) —O—C(O)—$CR^4(R^5)$—;
(h) —S—N=$CR^4$—;
(i) —O—N=$CR^4$—;
(j) —$CR^4(R^5)$—$NR^3$—C(O)—;
(k) —C(O)—$NR^3$—$CR^4(R^5)$—;
(l) —$NR^3$—C(O)—$CR^4(R^5)$—;
(m) —$CR^4(R^5)$—S—C(O)—;
(n) —C(O)—S—$CR^4(R^5)$—;
(o) —S—C(O)—$CR^4(R^5)$—;
(p) —$CR^4$=$CR^{4'}$—C(O)—;
(q) —C(O)—$CR^4$=$CR^{4'}$—;
(r) —O—$CR^4$=$CR^{4'}$—;
(s) —S—$CR^4$=$CR^{4'}$;
(t) —$NR^3$—$CR^4$=$CR^5$—;
(u) —S—$NR^3$—C(O)—;
(v) —O—$NR^3$—C(O)—; or
(w) —$NR^3$—N=$CR^4$—;
$R^1$, $R^2$, $R^3$, $R^4$, $R^{4'}$, $R^5$ and $R^{5'}$ are as defined herein; and with the proviso that the compounds of Formula XIV must contain at least one nitrite, nitrate, thionitrite or thionitrate group.

Another embodiment of the present invention provides compounds of the Formula (XV):

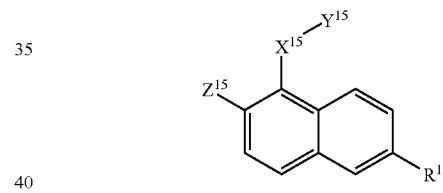

XV wherein:
$X^{15}$ is:
(a) —C(O)—;
(b) —$CH_2$—;
(c) —$CH(OD^1)$—;
(d) —C=N—O-lower alkyl-;
(e) —O—;
(f) —$S(O)_o$—;
(g) —$NR^{92}$; or
(g) covalent bond;
$Y^{15}$ is:
(a) aryl; or
(b) cycloalkyl;
$Z^{15}$ is:
(a) hydrogen;
(b) alkyl;
(c) haloalkyl;
(d) cycloalkyl;
(e) alkoxy;
(f) alkylthio;
(g) cycloalkylalkylthio;
(h) cycloalkylalkoxy;
(i) —$OD^1$;
(j) halo;
(k) cyano;

(l) —C(O)OD$^1$;
(m) —C(O)-lower alkyl;
R$^{92}$ is:
 (a) hydrogen;
 (b) lower alkyl;
 (c) —C(O)-lower alkyl; or
 (d) K;
R$^1$, D$^1$, K and o are as defined herein; and
with the proviso that the compounds of Formula XV contain at least one nitrite, nitrate, thionitrite or thionitrate group.

Another embodiment of the present invention provides compounds of the Formula (XVI):

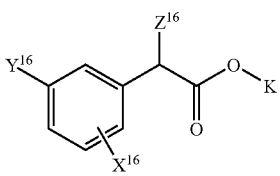

XVI wherein X$^{16}$ is:

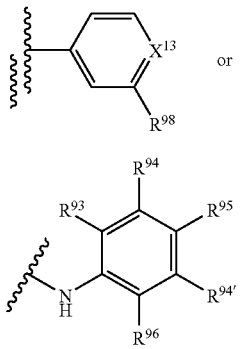

(a)

(b)

Y$^{16}$ is:
 (a) hydrogen;
 (b) halogen;
 (c) methyl; or
 (d) ethyl;
Z$^{16}$ is:
 (a) hydrogen; or
 (b) methyl;
R$^{93}$ is:
 (a) chloro; or
 (b) fluoro;
R$^{94}$ and R$^{94'}$ are each independently:
 (a) hydrogen; or
 (b) fluoro;
R$^{95}$ is:
 (a) chloro;
 (b) fluoro;
 (c) hydrogen;
 (d) methyl;
 (e) ethyl;
 (f) methoxy;
 (g) ethoxy; or
 (i) hydroxy;
R$^{96}$ is:
 (a) chloro;
 (b) fluoro;
 (c) trifluoromethyl; or
 (d) methyl;

R$^{98}$ is:
 (a) lower alkyl;
 (b) lower alkenyl;
 (c) alkoxy; or
 (d) alkylthio;
K and X$^{13}$ are as defined herein; and
with the proviso that the compounds of Formula XVI must contain at least one nitrite, nitrate, thionitrite or thionitrate group.

Compounds of the present invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. The present invention includes within its scope all such isomers and mixtures thereof.

Another aspect of the present invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The compounds of Formulas (I), (II), (III), (IV), (V), (VI), (VII), (VIII), (IX), (X), (XI), (XII), (XIII), (XIV), (XV) and (XVI) can be synthesized by one skilled in the art following the methods and examples described herein. The synthesis of the parent COX-2 inhibitors (i.e. non-nitrosated and/or non-nitrosylated COX-2 inhibitors) are disclosed in, for example, U.S. Pat. Nos. 5,344,991, 5,393,790, 5,466,823, 5,474,995, 5,486,534, 5,504,215, 5,508,426, 5,510,496, 5,516,907, 5,521,207, 5,536,752, 5,550,142, 5,563,165, 5,616,601, 5,620,999, 5,677,318, 5,668,161, 5,691,374, 5,698,584, 5,710,140, 5,753,688, 5,859,257, 5,908,858, 5,945,539, 5,994,381, 6,080,876, 6,083,969 and 6,071,954 and in WO 91/19708, WO 94/15932, WO 94/26731, WO 94/27980, WO 95/00501, WO 95/11883, WO 95/15315, WO 95/15316, WO 95/15317, WO 95/15318, WO 95/18799, WO 95/21817, WO 95/30652, WO 96/30656, WO 96/03387, WO 96/03392, WO 96/03385, WO 96/03387, WO 96/03388, WO 96/09293, WO 96/09304, WO 96/16934, WO 96/19462, WO 96/19463, WO 96/19469, WO 96/25405, WO 96/36617, WO 96/36623, WO 97/11704, WO 97/13755, WO 97/27181, WO 97/14691, WO 97/16435, WO 97/34882, WO 97/36863, WO 97/40012, WO 97/45420, WO 98/00416, WO 98/11080, WO 98/22422, WO 98/41516, WO 98/46594, WO 98/52937, WO 99/15531, WO 99/23087, WO 99/33796, WO 99/25695, WO 99/61016, WO 99/62884 and WO 99/64415 and in EP 0 745 596 A1, EP 0 087 629 B1, EP 0 418 845 B1, EP 0 554 829 A2,EP 0 863 134 A1, EP 1 006 114 A1 for the parent compounds of Formulas (I) and (II); and in U.S. Pat. Nos. 5,733,909, 5,789,413 and 5,849, 943 and in WO 96/13483, WO 97/28120 and WO 97/28121 for the parent compounds of Formula (III); and in U.S. Pat. Nos. 5,861,419 and 6,001,843 and in WO 96/10012, WO 96/16934, WO 96/24585, WO 98/03484, WO 98/24584, WO 98/47871, WO 99/14194 and WO 99/14195 for the parent compounds of Formula (IV); and in U.S. Pat. Nos. 5,436,265, 5,510,368, 5,604,253 and 5,639,780 and in WO 96/37467, WO 96/37468, WO 96/37469, WO 98/39330 and WO 00/40087 for the parent compounds of Formula (V); and in U.S. Pat. Nos. 5,409,9444, 5,604,260, 5,968,859, 5,776,984, 5,968,958 and in WO 94/13635, WO 94/20480, WO 96/23786, WO 97/03953, WO 98/33769 and WO 99/15503 for the parent compounds of Formula (VI); and in WO 98/41511, WO 99/10331, WO 99/10332 and WO 00/24719 for the parent compounds of Formula (VII); and in WO 98/47890 and WO 00/23443 for the parent compounds of Formula (VIII), and in U.S. Pat. Nos. 5,807,873 and WO 98/43966 for the parent compounds of Formula (IX); and in U.S. Pat. Nos. 5,521,213 and 5,552,422 and in WO 96/06840, WO 96/21667, WO 96/31509, WO 99/12930, WO 00/08024 and WO 00/26216 for the parent compounds of Formula (X); and in U.S. Pat. Nos. 5,776,967, 5,824,699 and 5,830,911 and in WO 98/04527 for the parent compounds of Formula (XI); and in U.S. Pat. Nos. 5,750,558 and 5,756,531 and in WO 97/41100, WO 98/05639, WO 98/21195, WO 98/57924, WO 99/05104 and WO 99/35130 for the parent compounds of Formula (XII); and in WO 99/61436 for the parent compounds of Formula (XIII); and in WO 00/10993 for the parent compounds of Formula (XIV); and in WO 98/32732 for the parent compounds of Formula (XV); and in WO 97/09977, WO 99/11605 and WO 99/41224 for the parent compounds of Formula (XVI); the disclosures of each of which are incorporated by reference herein in their entirety. The parent COX-2 inhibitor compounds can then be nitrosated and/or nitrosylated through one or more sites-such as oxygen, sulfur and/or nitrogen using the methods described in the examples herein and using conventional methods known to one skilled in the art. For example, known methods for nitrosating and nitrosylating compounds are described in U.S. Pat. Nos. 5,380,758 and 5,703,073; WO 97/27749; WO 98/19672; and Oae et al, Org. Prep. Proc. Int., 15(3):165–198 (1983), the disclosures of each of which are incorporated by reference herein in their entirety. The methods of nitrosating and/or nitrosylating the compounds described in the examples herein and in these references can be applied by one skilled in the art to produce any of the nitrosated and/or nitrosylated COX-2 inhibitors described herein.

The compounds of the present invention include the parent COX-2 inhibitors, including those described herein, which have been nitrosated and/or nitrosylated through one or more sites such as oxygen (hydroxyl condensation), sulfur (sulfhydryl condensation) and/or nitrogen. The nitrosated and/or nitrosylated COX-2 inhibitors of the present invention donate, transfer or release a biologically active form of nitrogen monoxide (i.e., nitric oxide).

Nitrogen monoxide can exist in three forms: NO– (nitroxyl), NO. (uncharged nitric oxide) and NO$^+$ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO$^+$) does not react with $O_2$ or $O_2^-$ species, and functionalities capable of transferring and/or releasing NO$^+$ and NO— are also resistant to decomposition in the presence of many redox metals. Consequently, administration of charged NO equivalents (positive and/or negative) is a more effective means of delivering a biologically active NO to the desired site of action.

Compounds contemplated for use in the present invention (e.g., nitrosated and/or nitrosylated COX-2 inhibitors) are, optionally, used in combination with nitric oxide and compounds that release nitric oxide or otherwise directly or indirectly deliver or transfer a biologically active form of nitrogen monoxide to a site of its intended activity, such as on a cell membrane in vivo.

The term "nitric oxide" encompasses uncharged nitric oxide (NO.) and charged nitrogen monoxide species, preferably charged nitrogen monoxide species, such as nitrosonium ion (NO$^+$) and nitroxyl ion (NO—). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexene amines or amides, nitrosoamines, furoxans as well as substrates for the endogenous enzymes which synthesize nitric oxide. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, Org. Prep. Proc. Int., 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetyl-penicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_{mm}SNO$;

(ii) $ONS(C(R_e)(R_f))_{mm}R_e$; and (iii) $H_2N\text{—}CH(CO_2H)\text{—}(CH_2)_{mm}\text{—}C(O)NH\text{—}CH(CH_2SNO)\text{—}C(O)NH\text{—}CH_2\text{—}CO_2H$;

wherein mm is an integer from 2 to 20; $R_e$ and $R_f$ are each independently a hydrogen, an alkyl, a cycloalkoxy, a halogen, a hydroxy, an hydroxyalkyl, an alkoxyalkyl, an aryl-heterocyclic ring, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an alkoxy, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a carbamoyl, a urea, a nitro, —T—Q—, or $(C(R_e)(R_f))_k$—T—Q, or $R_e$ and $R_f$ taken together are an oxo, a methanthial, a heterocyclic ring, a cycloalkyl group or a bridged cycloalkyl group; Q is —NO or —$NO_2$; and T is independently a covalent bond, a carbonyl, an oxygen, —$S(O)_o$— or —$N(R_a)R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —$CH_2$—C(T—Q)($R_e$)($R_f$), or —($N_2O_2$—)⁻.M⁺, wherein M⁺ is an organic or inorganic cation; with the proviso that when $R_i$ is —$CH_2$—C(T—Q)($R_e$)($R_f$) or —($N_2O_2$—).M⁺; then "—T—Q" can be a hydrogen, an alkyl group, an alkoxyalkyl group, an aminoalkyl group, a hydroxy group or an aryl group.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetraflurorborate in an inert solvent.

Another group of NO adducts for use in the present invention, where the NO adduct is a compound that donates, transfers or releases nitric oxide, include compounds comprising at least one ON—O—, ON—N— or ON—C-group. The compounds that include at least one ON—O—, ON—N— or ON—C-group are preferably ON—O—, ON—N— or ON—C-polypeptides (the term "polypeptide" includes proteins and polyamino acids that do not possess an ascertained biological function, and derivatives thereof); ON—O—, ON—N— or ON—C-amino acids (including natural and synthetic amino acids and their stereoisomers and racemic mixtures); ON—O—, ON—N— or ON—C-sugars; ON—O—, ON—N— or ON—C-modified or unmodified oligonucleotides (comprising at least 5 nucleotides, preferably 5–200 nucleotides); ON—O—, ON—N— or ON—C-straight or branched, saturated or unsaturated, aliphatic or aromatic, substituted or unsubstituted hydrocarbons; and ON—O—, ON—N— or ON—C-heterocyclic compounds.

Another group of NO adducts for use in the present invention include nitrates that donate, transfer or release nitric oxide, such as compounds comprising at least one $O_2N$—O—, $O_2N$—N—, $O_2N$—S— or $O_2N$—C-group. Preferred among these compounds are $O_2N$—O—, $O_2N$—N—, $O_2N$—S— or $O_2N$—C-polypeptides (the term "polypeptide" includes proteins and also polyamino acids that do not possess an ascertained biological function, and derivatives thereof); $O_2N$—O—, $O_2N$—N—, $O_2N$—S— or $O_2N$—C-amino acids (including natural and synthetic amino acids and their stereoisomers and racemic mixtures); $O_2N$—O—, $O_2N$—N—, $O_2N$—S— or $O_2N$—C-sugars; $O_2N$—O—, $O_2N$—N—, $O_2N$—S— or $O_2N$—C-modified and unmodified oligonucleotides (comprising at least 5 nucleotides, preferably 5–200 nucleotides); $O_2N$—O—, $O_2N$—N—, $O_2N$—S— or $O_2N$—C-straight or branched, saturated or unsaturated, aliphatic or aromatic, substituted or unsubstituted hydrocarbons; and $O_2N$—O—, $O_2N$—N—, $O_2N$—S— or $O_2N$—C-heterocyclic compounds. Preferred examples of compounds comprising at least one $O_2N$—O—, $O_2N$—N—, $O_2N$—S— or $O_2N$—C-group include isosorbide dinitrate, isosorbide mononitrate, clonitrate, erythrityltetranitrate, mannitol hexanitrate, nitroglycerin, pentaerythritoltetranitrate and pentrinitrol. Preferred are those —S—$NO_2$ compounds that are polypeptides or hydrocarbons with a pair or pairs of thiols that are sufficiently structurally proximate, i.e., vicinal, that the pair of thiols will be reduced to a disulfide. Compounds which form disulfide species release nitroxyl ion (NO—) and uncharged nitric oxide (NO.). Compounds where the thiol groups are not sufficiently close to form disulfide bridges generally provide nitric oxide as the NO— form and not as the uncharged NO. form.

Another group of NO adducts are N-oxo-N-nitrosoamines that donate, transfer or release nitric oxide and are represented by the formula: $R^1R^2N$—N(O—M⁺)—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where M⁺ is an organic or inorganic cation, such as, for example, an alkyl substituted ammonium cation or a Group I metal cation.

The present invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoargrnine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, omithine or glutamine, inhibitors of the enzyme arginase (e.g., N-hydroxy-L-arginine and 2(S)-amino-6-boronohexanoic acid) and the substrates for nitric oxide synthase, cytokines, adenosine, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524–526 (1987); Ignarro et al, *Proc. Natl. Acad. Sci. USA*, 84:9265–9269 (1987)).

Another embodiment of the present invention provides compositions comprising at least one parent COX-2 inhibitor and at least one compound that donates, transfers or releases nitric oxide, or elevates levels of endogenous EDRF or nitric oxide, or is a substrate for nitric oxide synthase. The parent COX-2 inhibitors includes any of those described in the prior art, including those described in the patents and publications cited herein, as well as the novel compounds described herein.

The present invention is also based on the discovery that compounds and compositions of the present invention may also be used in conjunction with other therapeutic agents for co-therapies, partially or completely, in place of other conventional antiinflammatory compounds, such as, for example, together with steroids, NSAIDs, 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG-CoA inhibitors, $H_2$ receptor antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures thereof.

Leukotriene $A_4$ ($LTA_4$) hydrolase inhibitors refers to compounds that selectively inhibit leukotriene $A_4$ hydrolase with an $IC_{50}$ of less than about 10 µM, and more preferably with an $IC_{50}$ of less than about 1 µM. Suitable $LTA_4$ hydrolase inhibitors include, but are not limited to, RP-64966, (S,S)-3-amino-4-(4-benzyloxyphenyl)-2-hydroxybutyric acid benzyl ester (Scripps Res. Inst.), N-(2(R)-(cyclohexylmethyl)-3-(hydroxycarbamoyl)propionyl)-L-alanine (Searle), 7-(4-(4-ureidobenzyl)phenyl) heptanoic acid (Rhone-Poulenc Rorer), and 3(3-(1E,3E-tetradecadienyl)-2-oxiranyl) benzoic acid lithium salt (Searle), and mixtures thereof.

Suitable $LTB_4$ receptor antagonists include, but are not limited to, ebselen, linazolast, ontazolast; WAY 121006 (American Home Products); Bay-x-1005 (Bayer); BI-RM-270 (Boehringer Ingleheim); CGS-25019C (Ciba Geigy); ETH-615 (Leo Denmark); MAFP (Merck); TMK-688 (Terumo); T-0757 (Tanabe); LY 213024, LY 210073, LY 223982, LY 233469, LY 255283, LY 264086, LY 292728 and LY 293111 (Eli Lilly); ONO-LB457, ONO-4057, and ONO-LB-448 (ONO), S-2474, calcitrol (Shionogi); PF 10042 (Perdu Frederick); Pfizer 105696 (Pfizer Inc.); RP 66153 (Rhone-Poulenc); SC-53228, SC-41930, SC-50605, SC-51146 and SC-53228 (Searle); SB-201146 and SB-209247 (SmithKline Beecham); SKF-104493 (SmithKline & French); SM 15178 (Sumitamo); TMK-688 (Terumo); BPC 15, (Warner Lambert); and mixtures thereof. The preferred $LTB_4$ receptor antagonists are calcitrol, ebselen, Bay-x-1005, CGS-25019C, ETH-615, LY-293111, ONO-4057 and TMK-688, and mixtures thereof.

Suitable 5-LO inhibitors include, but are not limited to, A-76745, 78773 and ABT761 (Abbott compounds); Bay-x-1005 (Bayer); CMI-392 (Cytomed); E-3040 (Eisai); EF-40 (Scotia Pharmaceutical); F-1322 (Fujirebio); ML-3000 (Merckle); PF-5901 (Purdue Frederick); R-840 (3M Pharmaceuticals); rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast, and mixtures thereof. Suitable 5-LO inhibitors are also described more fully in WO 97/29776 assigned to G. D. Searle & Co.

Suitable 5-HT agonists, include, but are not limited to, rizatriptan, sumatriptan, naratriptan, zolmitroptan, eleptriptan, almotriptan, ergot alkaloids. ALX 1323, Merck L 741604 SB 220453 and LAS 31416. Suitable 5-HT agonists are described more fully in WO 0025779, assigned to Merck & Co., Inc and in WO 00/48583, assigned to Pozen Inc. 5-HT agonists refers to a compound that is an agonist to any 5-HT receptor, including but not limited to, $5\text{-HT}_1$ agonists, $5\text{-HT}_{1B}$ agonists and $5\text{-HT}_{1D}$ agonists.

Suitable steroids, include, but are not limited to, budesonide, dexamethasone, corticosterone, prednisolone, and the like. Suitable steroids are described more fully in the literature, such as in the Merck Index on CD-ROM, Twelfth Edition, Version 12:1, 1996.

Suitable HMG CoA inhibitors, include, but are not limited to, reductase and synthase inhibitors, such as, for example, squalene synthetase inhibitors, benzodiazepine squalene synthase inhibitors, squalene epoxidase inhibitors, acyl-coenzyme A, bile acid sequestrants, cholesterol absorption inhibitors, and the like.

Suitable NSAIDs, include, but are not limited to, acetaminophen, aspirin, diclofenac, ibuprofen, ketoprofen, naproxen and the like. Suitable NSAIDs are described more fully in the literature, such as in Goodman and Gilman, The Pharmacological Basis of Therapeutics (9th Edition), McGraw-Hill, 1995, Pgs. 617–657; and the Merck Index on CD-ROM, Twelfth Edition, Version 12:1, 1996.

Suitable $H_2$ receptor antagonists, include, but are not limited to, cimetidine, roxatidine, rantidine and the like. Suitable $H_2$ receptor antagonists are described more fully in the literature, such as in Goodman and Gilman, The Pharmacological Basis of Therapeutics (9th Edition), McGraw-Hill, 1995, Pgs. 901–915; and the Merck Index on CD-ROM, Twelfth Edition, Version 12:1, 1996.

Suitable antineoplastic agents, include but are not limited to, 5-FU-fibrinogen, acanthifolic acid, aminothiadiazole, altretamine, anaxirone, aclarubicin and the like. Suitable antineoplastic agents are also described more fully in U.S. Pat. No. 6,025,353 and WO 00/38730 assigned to G. D. Searle & Co.

Suitable antiplatelet agents, include but are not limited to, aspirin, ticlopidine, dipyridamole, clopidogrel, glycoprotein IIb/IIIa receptor antagonists, and the like.

Suitable decongestants include, but are not limited to, phenylephrine, phenylpropanolamine, pseudophedrine, oxymetazoline, ephinephrine, naphazoline, xylometazoline, propylhexedrine, levo-desoxyephedrine, and the like.

Suitable antitussives include, but are not limited to, codeine, hydrocodone, caramiphen, carbetapentane, dextramethorphan, and the like.

Suitable proton pump inhibitors, include, but are not limited to, omeprazole, lansoprazole, rabeprazole, pantoprazole, and the like. Suitable proton pump inhibitors are described more fully in the literature, such as in Goodman and Gilman, The Pharmacological Basis of Therapeutics (9th Edition), McGraw-Hill, 1995, Pgs. 901–915; and the Merck Index on CD-ROM, Twelfth Edition, Version 12:1, 1996.

The compounds and compositions of the present invention, may also be used in combination therapies with opioids and other analgesics, including, but not limited to, narcotic analgesics, Mu receptor antagonists, Kappa receptor antagonists, non-narcotic (i.e. non-addictive) analgesics, monoamine uptake inhibitors, adenosine regulating agents, cannabinoid derivatives, neurokinin 1 receptor antagonists, Substance P antagonists, neurokinin 1 receptor antagonists, sodium channel blockers, N-methyl-D-aspartate receptor antagonists, and mixtures thereof. Preferred combination therapies would be with morphine, meperidine, codeine, pentazocine, buprenorphine, butorphanol, dezocine, meptazinol, hydrocodone, oxycodone, methadone, Tramadol ((+) enantiomer), DuP 747, Dynorphine A, Enadoline, RP-60180, HN-11608, E-2078,ICI-204448, acetaminophen (paracetamol), propoxyphene, nalbuphine, E-4018, filenadol, mirtentanil, amitriptyline, DuP631, Tramadol ((−) enantiomer), GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, CP-99,994, and mixtures thereof.

The compounds and compositions of the present invention can also be used in combination with inducible nitric oxide synthase (iNOS) inhibitors. Suitable iNOS inhibitors are disclosed in U.S. Pat. Nos. 5,132,453 and 5,273,875, and in WO 97/38977 and WO 99/18960, the disclosures of each of which are incorporated by reference herein in their entirety.

The present invention is also based on the discovery that the administration of a therapeutically effective amount of the compounds and compositions described herein is effective for treating inflammation, pain (both chronic and acute), and fever, such as, for example, analgesic in the treatment of pain, including, but not limited to headaches, migraines, postoperative pain, dental pain, muscular pain, and pain resulting from cancer; as an antipyretic for the treatment of fever, including but not limited to, rheumatic fever, symptoms associated with influenza or other viral infections, common cold, low back and neck pain, dysmenorrhea, headache, toothache, sprains, strains, myositis, neuralgia, synovitis; arthritis, including but not limited to rheumatoid arthritis, degenerative joint disease (osteoarthritis), spondyloarthropathies, gouty arthritis, systemic lupus erythematosus and juvenile arthritis. For example, the patient can be administered a therapeutically effective amount of at least one nitrosated and/or nitrosylated COX-2 inhibitor of the present invention. In another embodiment, the patient can be administered a therapeutically effective amount of at least one nitrosated and/or nitrosylated COX-2 inhibitor and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated and/or nitrosylated COX-2 inhibitor, and, at least one therapeutic agent, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Another embodiment of the invention provides methods for decreasing and/or preventing gastrointestinal disorders and improving the gastrointestinal properties of the parent COX-2 inhibitor (i.e., non-nitrosated and/or non-nitrosylated COX-2 inhibitor) by administering to the patient in need thereof a therapeutically effective amount of the compounds and/or compositions described herein. Such gastrointestinal disorders refer to any disease or disorder of the upper gastrointestinal tract (e.g., esophagus, stomach, duodenum and jejunum) including, for example, inflammatory bowel disease, Crohn's disease, gastritis, irritable bowel syndrome, ulcerative colitis, peptic ulcers, stress ulcers, gastric hyperacidity, dyspepsia, gastroparesis, Zollinger-Ellison syndrome, gastroesophageal reflux disease, bacterial infections (including, for example, a *Helicobacter Pylori* associated disease), short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns. For example, the patient can be administered a therapeutically effective amount of at least one nitrosated and/or nitrosylated COX-2 inhibitor of the present invention. In another embodiment, the patient can be administered a therapeutically effective amount of at least one nitrosated and/or nitrosylated COX-2 inhibitor and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated and/or nitrosylated COX-2 inhibitor and at least one therapeutic agent, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Yet another embodiment of the invention provides methods for facilitating wound healing (such as, for example, ulcer healing) by administering to the patient in need thereof a therapeutically effective amount of the compounds and/or compositions described herein. Wound refers to, and includes, any lesion that is characterized by loss of tissue, and, includes, but is not limited to, ulcers, cuts, burns, and the like. Ulcers refers to lesions of the upper gastrointestinal tract lining that are characterized by loss of tissue, and, include, but are not limited to, gastric ulcers, duodenal ulcers, gastritis, and the like. For example, the patient can be administered a therapeutically effective amount of at least one nitrosated and/or nitrosylated COX-2 inhibitor of the present invention. In another embodiment, the patient can be administered a therapeutically effective amount of at least one nitrosated and/or nitrosylated COX-2 inhibitor and at least one nitric oxide donor. In yet another embodiment, the patient can be administered a therapeutically effective amount of at least one nitrosated and/or nitrosylated COX-2 inhibitor and at least one therapeutic agent, and, optionally, at least one nitric oxide donor. The compounds can be administered separately or in the form of a composition.

Another embodiment of the invention provides methods to decrease or reverse renal and other toxicities (such as, for example, kidney toxicity) by administering to a patient in need thereof a therapeutically effective amount of the compounds and/or compositions described herein. For example, the patient can be administered a therapeutically effective amount of at least one nitrosated and/or nitrosylated COX-2 inhibitor of the present invention. In another embodiment, the patient can be administered a therapeutically effective amount of at least one nitrosated and/or nitrosylated COX-2 inhibitor and at least one nitric oxide donor. In yet another embodiment, the patient can be administered a therapeutically effective amount of at least one nitrosated and/or nitrosylated COX-2 inhibitor and at least one therapeutic agent, and, optionally, at least one nitric oxide donor. The compounds can be administered separately or in the form of a composition.

Another embodiment of the invention provides methods to treat or prevent disorders resulting from elevated levels of COX-2 by administering to a patient in need thereof a therapeutically effective amount of the compounds and/or compositions described herein. For example, the patient can be administered a therapeutically effective amount of at least one nitrosated and/or nitrosylated COX-2 inhibitor of the present invention. In another embodiment, the patient can be administered a therapeutically effective amount of at least one nitrosated and/or nitrosylated COX-2 inhibitor and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated and/or nitrosylated COX-2 inhibitor and at least one therapeutic agent, including but not limited to, steroids, a non-steroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Disorders resulting from elevated levels of COX-2 (e.g., COX-2 mediated disorders) include, but are not limited to, for example, angiogenesis, arthritis, asthma, bronchitis, menstrual cramps, premature labor, tendinitis, bursitis; skin-related conditions, such as, for example, psoriasis, eczema, surface wounds, burns and dermatitis; post-operative inflammation including from ophthalmic surgery, such as, for example, cataract surgery and refractive surgery, and the like; treatment of neoplasia, such as, for example, brain cancer, bone cancer, epithelial cell-derived neoplasia (epithelial carcinoma), such as, for example, basal cell carcinoma, adenocarcinoma, gastrointestinal cancer, such as, for example, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body, benign and cancerous tumors, growths, polyps, adenomatous polyps, including, but not limited to, familial adenomatous polyposis, fibrosis resulting from radiation therapy, and the like; treatment of inflammatory processes in diseases, such as, for example, vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like; treatment of ophthalmic diseases and disorders, such as, for example, retinitis, retinopathies, uveitis, ocular photophobia, acute injury to the eye tissue, glaucoma, inflammation of the eye and elevation of intraocular pressure and the like; treatment of pulmonary inflammation, such as, for example, those associated with viral infections and cystic fibrosis, and the like; treatment of certain central nervous system disorders, such as, for example, cortical dementias including Alzheimer's disease, vascular dementia, multi-infarct dementia, pre-senile dementia, alcoholic dementia, senile dementia, and central nervous system damage resulting from stroke, ischemia and trauma, and the like; treatment of allergic rhinitis, respiratory distress syndrome, endotoxin shock syndrome, atherosclerosis; treatment of inflammations and/or microbial infections including, for example, inflammations and/or infections of the eyes, ears, nose, throat, and/or skin; treatment and/or prevention of cardiovascular disorders, such as, for example, coronary artery disease, aneurysm, arteriosclerosis, atherosclerosis, including, but not limited to, cardiac transplant atherosclerosis, myocardial infarction, ischemia, embolism, stroke, thrombosis, hypertension, venous thrombosis, thromboembolism, thrombotic occlusion and reclusion, restenosis, angina, unstable angina, shock, heart failure, coronary plaque inflammation, bacterial-induced inflammation, such as, for example, *Chlamydia*-induced inflammation, viral induced inflammation, inflammation associated with surgical procedures, such as, for example, vascular grafting, coronary artery bypass surgery, revascularization procedures, such as, for example, angioplasty, stent placement, endarterectomy, vascular procedures involving arteries, veins, capillaries, and the like; treatment and/or prevention of urinary and/or urological disorders, such as, for example, incontinence and the like; treatment and/or prevention of endothelial dysfunctions, such as, for example, diseases accompanying these dysfunctions, endothelial damage from hypercholesterolemia, endothelial damage from hypoxia, endothelial damage from mechanical and chemical noxae, especially during and after drug, and mechanical reopening of stenosed vessels, for example, following percutaneous transluminal angiography (PTA) and percuntaneous transluminal coronary angiography (PTCA), endothelial damage in postinfarction phase, endothelium-mediated reocclusion following bypass surgery, blood supply disturbances in peripheral arteries, as well as, cardiovascular diseases, and the like; preservation of organs and tissues, such as, for example, for organ transplants, and the like; inhibition and/or prevention of activation, adhesion and infiltration of neutrophils at the site of inflammation; inhibition and/or prevention of platelet aggregation. The compounds and compositions of the present invention can also be used as a pre-anesthetic medication in emergency operations to reduce the danger of aspiration of acidic gastric contents.

When administered in vivo, the compounds and compositions of the present invention can be administered in combination with pharmaceutically acceptable carriers and in dosages described herein. When the compounds and compositions of the present invention are administered as a mixture of at least one nitrosated and/or nitrosylated COX-2 inhibitor and at least one nitric oxide donor and/or therapeutic agent, they can also be used in combination with one or more additional compounds which are known to be effective against the specific disease state targeted for treatment. The nitric oxide donors, therapeutic agents and/or other additional compounds can be administered simultaneously with, subsequently to, or prior to administration of the nitrosated and/or nitrosylated COX-2 inhibitor.

Another embodiment of the present invention provides methods for treating inflammation, pain and fever; for treating and/or improving the gastrointestinal properties of COX-2 inhibitors; for facilitating wound healing; for treating and/or preventing renal toxicity; and for treating and/or preventing other cyclooxygenase-2 mediated disorders comprising administration of at least one parent COX-2 inhibitor and at least one nitric oxide donor, and, optionally, at least one therapeutic agent. For example, the patient can be administered a therapeutically effective amount of at least one parent COX-2 inhibitor of the present invention and at least one nitric oxide donor. In yet another embodiment, the patient can be administered a therapeutically effective amount of at least one parent COX-2 inhibitor, at least one nitric oxide donor and at least one therapeutic agent. The compounds can be administered separately or in the form of a composition.

The compounds and compositions of the present invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the present invention, including, for example, encapsulation in liposomes, microbubbles, emulsions, microparticles, microcapsules and the like. The required dosage can be administered as a single unit or in a sustained release form.

The bioavailability of the compositions can be enhanced by micronization of the formulations using conventional techniques such as grinding, milling, spray drying and the like in the presence of suitable excipients or agents such as phospholipids or surfactants.

The preferred methods of administration of the nitrosated and/or nitrosylated COX-2 inhibitor compositions or the parent COX-2 inhibitor for the treatment of gastrointestinal disorders are orally, bucally or by inhalation. The preferred methods of administration for the treatment of inflammation and microbial infections are orally, bucally, topically, transdermally or by inhalation.

The compounds and compositions of the present invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesuifonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given nitrosated and/or nitrosylated COX-2 inhibitor or the parent COX-2 inhibitor which will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the COX-2 inhibitor. The usual daily doses of nitrosated and/or nitrosylated COX-2 inhibitors are about 0.001 mg to about 140 mg/kg of body weight per day, preferably 0.005 mg to 30 mg/kg per day, or alternatively about 0.5 mg to about 7 g per patient per day. For example, inflammations may be effectively treated by the administration of from about 0.01 mg to 50 mg of the compound per kilogram of body weight per day, or alternatively about 0.5 mg to about 3.5 g per patient per day. The compounds may be administered on a regimen of up to 6 times per day, preferably 1 to 4 times per day, and most preferably once per day. Effective doses may be extrapolated from dose-response curves derived from in vitro or animal model test systems and are in the same ranges or less than as described for the commercially available compounds in the Physician's Desk Reference, supra.

The present invention also provides pharmaceutical kits comprising one or more containers filled with one or more of the ingredients of the pharmaceutical compounds and/or compositions of the present invention, including, at least, one or more of the COX-2 inhibitors optionally substituted with at least one NO and/or $NO_2$ group, described herein and one or more of the NO donors described herein. Associated with such kits can be additional therapeutic agents or compositions (e.g., steroids, NSAIDs, 5-lipoxygenase (5-LO) inhibitors, leukotriene B$_4$ (LTB$_4$) receptor antagonists and leukotriene A$_4$ (LTA$_4$) hydrolase inhibitors, 5-HT agonists, HMG-CoA inhibitors, H$_2$ antagonists, antineoplastic agents, antiplatelet agents, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like), devices for administering the compositions, and notices in the form prescribed by a governmental agency regulating the manufacture, use or sale of pharmaceuticals or biological products which reflects approval by the agency of manufacture, use or sale for humans.

EXAMPLES

The following non-limiting examples further describe and enable one of ordinary skill in the art to make and use the present invention. In each of the examples, flash chromatography was performed on 40 micron silica gel (Baker).

Example 1

4-(5-(4-Chlorophenyl)-3-((nitrooxy)methyl)-3-hydropyrazolyl) benzenesulfonamide.

1a. 4-(5-(4-Chlorophenyl)-3-(hydroxymethyl)-3-hydropyrazolyl) benzenesulfonamide.

This compound was synthesized as described by Penning et al, *J. Med. Chem.*, 40: 1347–1365 (1997), (the disclosure of which is incorporated by reference herein in its entirety), Example 14a. $^1$H NMR (300 MHz, CDCl$_3$) δ 7.87 (d, J=8.7 Hz, 2H), 7.39 (d, J=8.7 Hz, 2H), 7.33 (d, J=8.7 Hz, 2 H), 7.15 (d, J=8.4 Hz, 2H), 6.54 (s, 1H), 4.79 (s, 2H).

1b. 4-(5-(4-Chlorophenyl)-3-((nitrooxy)methyl)-3-hydropyrazolyl) benzenesulfonamide.

To a solution of the product of Example 1a (348 mg, 0.95 mmol) in EtOAc (10 mL) was added over 5 minutes at room temperature a mixture of HNO$_3$ (85 μl, fuming 90%) in acetic anhydride (400 μL). The reaction was stirred for 15 minutes at room temperature. The mixture was poured into excess aqueous Na$_2$CO$_3$. The aqueous layer was extracted with EtOAc. The combined organic layers were dried over Na$_2$SO$_4$ and concentrated. The residue was chromatographed on silica gel eluting with 2:1 Hex:EtOAc to give 210 mg (54%) of the title compound. $^1$H NMR (300 MHz, CDCl$_3$) δ 7.90 (d, J=8.2 Hz, 2H), 7.41 (d, J=8.8 Hz, 2H), 7.34 (d, J=8.5 Hz, 2H), 7.15 (d, J=8.5 Hz, 2H), 6.61 (s, 1H), 5.55 (s, 2H), 4.97 (s, 2H); $^{13}$C NMR (75 MHz, CDCl$_3$) δ 146.2, 143.8, 142.4, 141.2, 135.4, 130.0, 129.2, 128.2, 127.6, 127.5, 125.1, 109.2, 67.8.

Example 2

4-(5-((Nitrooxy)methyl)-3-phenylisoxazol-4-yl)benzenesulfonamide.

2a. 4-(5-(Hydroxymethyl)-3-phenylisoxazol-4-yl) benzenesulfonamide.

This compound was synthesized as described in patent application WO 96/25405, (the disclosure of which is incorporated by reference herein in its entirety), Example 10. $^1$H NMR (300 MHz, DMSO-d$_6$) δ 7.80 (d, J=8.3 Hz, 2H), 7.32–7.45 (mult, 9H), 5.71 (t, J=5.3 Hz, 1H), 4.52 (d, J=4.5 Hz, 2H); $^{13}$C NMR (75 MHz, DMSO-d$_6$) δ 69.5, 160.7, 143.5, 132.6, 130.1, 129.8, 128.8, 128.3, 128.2, 126.0, 115.2, 53.3; mass spectrum (API-TIS), m/z 331 (MH$^+$).

2b. 4-(5-((Nitrooxy)methyl)-3-phenylisoxazol-4-yl) benzenesulfonamide.

Concentrated HNO$_3$ (40 μL, 0.90 mmol) was added to stirred solution of acetic anhydride (200 μL, 2.1 mmol) in EtOAc (0.3 mL) at 0° C. via a syringe and stirred for 5 minutes at 0° C. The product of Example 2a (0.1 g, 0.3 mmol) in EtOAc (0.1 mL) was then added and stirred for 5 minutes at 0° C. The resulting mixture was then subjected to preparative thin layer chromatography (PTLC) eluting with 1:1 Hex:EtOAc to give the title compound (65 mg, 57%) as an oil. The oil was dissolved in CH$_2$Cl$_2$ (5 mL) and solvent was evaporated slowly overnight at room temperature to give the title compound as white crystals. mp 47–50° C. $^1$H-NMR (300 MHz, CDCl$_3$) δ 7.96 (d, J=8.4 Hz, 2H), 7.30–7.45 (mult, 7H), 5.49 (s, 2H), 4.89 (br s, 2H); $^{13}$C NMR (75 MHz, CDCl$_3$) δ 161.4, 160.5, 142.3, 133.0, 130.4, 130.3, 128.9, 128.4, 127.2, 127.1, 119.5, 62.7; mass spectrum (API-TIS), m/z 376 (MH$^+$)

Example 3

2-(1-Methyl-4-(nitrosothio)-4-piperidyl)ethyl 3-(N-((4-(5-methyl-3-phenylisoxazol-4-yl)phenyl)sulfonyl)carbamoyl)propanoate citrate salt 3a. Ethyl 2-(1-methyl-4-piperidylidene)acetate A solution of n-BuLi (1.6M in Hex, 58.7 mL, 93.6 mmol) was added to a stirred solution of triethyl phosphonoacetate (17.5 g, 78.0 mmol) in THF (30 mL) at −78° C. under N$_2$. The resulting brownish solution was stirred for 30 min and then a solution of 4-N-methylpiperidone (8.8 g, 78.0 mmol) in THF (20 mL) was added. The cold bath was removed and the mixture was stirred at room temperature for 2 hours. Water (250 mL) was added and the mixture was extracted with EtOAc (3×100 mL). The combined organic extracts were dried over Na$_2$SO$_4$. The solvent was evaporated to afford the title compound (13.2 g, 92%). $^1$H NMR (300 MHz, CDCl$_3$) δ 5.64 (s, 1H), 4.14 (q, J=7.1 Hz, 2H), 3.00 (t, J=5.1 Hz, 10H), 2.32–2.53 (mult, 5H), 2.29 (s, 3H), 1.27 (t, J=7.1 Hz, 3H); $^{13}$C NMR (75 MHz, CDCl$_3$) δ 1.664, 158.6, 114.2, 59.5, 56.7, 56.1, 45.7, 36.7, 29.3, 14.2.

3b. Ethyl 2-(1-methyl-4-(phenylmethylthio)piperidyl)acetate

The product of Example 3a (13.2 g, 72.01 mmol) and benzylmercaptan (8.4 mL, 72.01 mmol) in piperidine (35 mL) were heated at 100° C. for 12 hours and then cooled to room temperature. Water (50 mL) was added and the aqueous layer was extracted with EtOAc (3×100 mL). The combined organic layers were dried over Na$_2$SO$_4$. The solvent was evaporated and the residue was purified by chromatography on silica gel eluting with 1:9 MeOH:CH$_2$Cl$_2$ to afford the title compound (11.7 g, 53%) as a viscous liquid. $^1$H NMR (300 MHz, CDCl$_3$) δ 7.18–7.34 (mult, 5H), 4.17(q, J=7.1 Hz, 2H), 3.71 (s, 2H), 2.64 (s, 2H), 2.46–2.54 (mult, 4H), 2.29 (s, 3H), 1.83–1.95 (mult, 4H), 1.29 (t, J=7.1 Hz, 3H).

3c. 2-(1-Methyl-4-(phenylmethylthio)-4-piperidyl) ethan-1-ol

A solution of diisobutylaluminium hydride in hexane (83 mL, 83 mmol) was added to a stirred solution of the product of Example 3b (11.7 g, 38.74 mmol) in THF (40 mL) at −78° C. under $N_2$. The cold bath was removed and the mixture was stirred for 1.5 hours. Solid $Na_2SO_4 \cdot 10H_2O$ (3 g) was added portionwise with stirring until a thick precipitate was formed. 10% MeOH in $CH_2Cl_2$ (100 mL) was added and the mixture was filtered. The solid was washed with additional 10% MeOH in $CH_2Cl_2$ (100 mL) and the solvent was evaporated. The residue was chromatographed on silica gel eluting with 1:9 MeOH:$CH_2Cl_2$ to give the title compound (5.2 g, 50.6%) as a solid. $^1$H NMR (300 MHz, $CDCl_3$) δ 7.20–7.35 (mult, 5H), 3.86 (t, J=6.4 Hz, 2H), 3.66 (s, 2H), 2.50–2.57 (mult, 4H), 2.29 (s, 3H), 1.88 (t, J=6.5 Hz, 2H), 1.65–1.84 (mult, 4H).

3d. 2-(1-Methyl-4-(nitrosothio)-4-piperidyl)ethan-1-ol

The product of Example 3c (7.8 g, 29.38 mmol) was dissolved in THF (50 mL) and cooled to −78° C. and liquid $NH_3$ (~100 mL) was added. Small pieces of metallic sodium (2 g) were added until the blue color persisted for 10 minutes. Solid $NH_4Cl$ (~5 g) was added to discharge the color and the cold bath was removed and ammonia was evaporated (12 hours). Ether (100 mL) was added to the pale yellow solid and HCl in $Et_2O$ (10 mL) was added until the solution became acidic. The mixture was left in a freezer for 30 min. The solid which formed was removed by filtration and washed with $Et_2O$ (50 mL). The residue was triturated with MeOH (100 mL) and undissolved solid was removed by filtration. The solvent was concentrated to 25 mL and concentrated HCl (2 mL) was added. 90% t-BuONO (3.1 mL, 23.7 mmol) was added via syringe. The resulting olive green solution was stirred at room temperature for 20 minutes and then poured onto crushed ice (5 g). 10% $Na_2CO_3$ (10 mL) was added and the mixture was extracted with EtOAc (3×50 mL). The combined organics were dried over $Na_2SO_4$ and concentrated to give the title compound (3.6 g, 60%) as a green oil. $^1$H NMR (300 MHz, $CDCl_3$) δ 3.88 (t, J=6.9 Hz, 2H), 2.25–2.95 (mult, 13H), 2.30 (s, 3H); $^{13}$C NMR (75 MHz, $CDCl_3$) δ 62.5, 58.5, 57.8, 51.5, 46.1, 36.4.

3e. 4-(5-(Methyl)-3-phenylisoxazol-4-yl)benzenesulfonamide.

This compound was synthesized as described in patent application WO 96/25405, Example 1, the disclosure of which is incorporated by reference herein in its entirety. mp 170° C. $^1$H NMR (300 MHz, $CD_3CN$) δ 7.90 (d, J=8.4 Hz, 2 H), 7.39–7.49 (mult, 7 H), 5.48 (s, 2 H), 2.50 (s, 2 H); mass spectrum (API-TIS), m/z 315 (MH$^+$).

3f. 2-(1-Methyl-4-(nitrosothio)-4-piperidyl)ethyl 3-(N-((4-(5-methyl-3-phenyl isoxazol-4-yl)phenyl) sulfonyl)carbamoyl)propanoate.

To a stirred solution of the product of Example 3d (0.21 g, 1.03 mmol), the product of Example 3e (0.43 g, 1.03 mmol), and 4-(dimethylamino)pyridine (DMAP, 0.05 g) in $CH_2Cl_2$ (10 mL) was added solid DCC (0.34 g, 164 mmol). The solution was stirred for 24 hours at room temperature. The precipitate which formed was removed by filtration and the filtrate was concentrated under reduced pressure. The crude product was chromatographed on silica gel eluting with 1:1 EtOAc:Hex followed by 1:9 MeOH:$CH_2Cl_2$. This gave the title compound (178 mg, 29%) as a green foam. $^1$H-NMR (300 MHz, $CDCl_3$) δ 7.94 (d, J=8.2 Hz, 2H), 7.22–7.39 (mult, 7H), 4.47–4.57 (mult, 2H), 3.56–3.60 (mult, 2H), 3.15–3.25 (mult, 2H), 2.45–2.90 (mult, 10OH), 2.42 (s, 6H); $^{13}$C-NMR (75 MHz, $CDCl_3$) δ 178.5, 173.4, 167.1, 161.0, 143.0, 133.5, 129.7, 129.5, 128.6, 128.5, 128.4, 126.7, 114.9, 60.0, 56.2, 51.7, 45.5, 41.0, 33.9, 31.8, 30.3, 11.6; mass spectrum (API-TIS), m/z 601 (MH$^+$).

3g. 2-(1-Methyl-4-(nitrosothio)-4-piperidyl)ethyl 3-(N-((4-(5-methyl-3-phenyl isoxazol-4-yl)phenyl) sulfonyl)carbamoyl)propanoate Citrate Salt.

Citric acid (65 mg, 0.34 mmol) in MeOH (0.2 mL) was added to the product of Example 3f (170 mg, 0.28 mmol) dissolved in EtOAc (0.8 mL) and MeOH (0.4 mL). The green solution was left to crystallize at −20° C. for 48 hours. The solvent was decanted and the solid was dried under reduced pressure for 16 hours to give the title compound (124 mg, 55%) as shiny, olive green crystals. mp 82–84° C. (decom). $^1$H-NMR (300 MHz, $CDCl_3$) δ 8.16 (d, J=8.4 Hz, 2H), 7.52–7.60 (mult, 7H), 4.43 (t, J=6.4 Hz, 2H), 3.15–3.25 (mult, 2H), 2.50–2.99 (mult, 22H); mass spectrum (API-TIS), m/z 601 (MH$^+$).

Example 4

(2-(1-((4-Chlorophenyl)methyl)-5-methoxy-2-methylindol-3-yl)ethyl)nitrooxy

4a. 2-(1-((4-Chlorophenyl)methyl)-5-methoxy-2-methylindol-3-yl)ethan-1-ol

A solution of indomethacin (10 g, 28 mmol) in THF (90 mL) was immersed in an ice bath to maintain an internal temperature of 10–15° C. To this solution was added $BF_3$-$Et_2O$ (30 mL, 230 mmol) over 5 min, resulting in the formation of a precipitate. Sodium borohydride (4.2 g, 110 mmol) was added portionwise over 10 min resulting in vigorous effervescence. After gas evolution subsided the flask was stoppered and allowed to warm to room temperature. After 1 hour the pressure was vented through a needle. The heterogeneous mixture was stirred for 6 hours. The mixture was cooled in an ice bath and was quenched by adding saturated $NaHCO_3$. To break the resultant emulsion the mixture was made acidic with 1N HCl and extracted with a 3:1 mixture of $Et_2O$:Hexane (270 mL). The organic layer was washed with brine, dried over $Na_2SO_4$, and evaporated. The residue was taken up in a 3:1 mixture of hot Hex:EtOAc (80 mL). Upon cooling to room temperature, crystals began to form. Crystallization was completed by cooling to −20° C. The solid was removed by filtration, washed with cold 3:1 Hex:EtOAc (2×25), Hexane (1×25) and dried in vacuo. This gave the title compound (4.5 g, 49%) as a white solid. mp 113–115° C. $^1$H-NMR (300 MHz, $CDCl_3$) δ 7.24 (d, J=8.4 Hz, 2H), 7.06 (d, J=9.1 Hz, 1H), 7.03 (d, J=3.5 Hz, 1H), 6.87 (d, J=8.3 Hz, 2H), 6.78 (dd, J=2.4 and 8.7 Hz, 1H), 5.23 (s, 2H), 3.86 (s, 3H), 3.84 (t, J=6.5 Hz, 2H), 2.99 (t, J=6.5 Hz, 2H), 2.29 (s, 3H); mass spectrum (API-TIS) m/z 330 (MH+). Anal calcd for $C_{19}H_{20}ClNO_2$: C, 69.19; H, 6.11; N, 4.25; Cl, 10.75. Found: C, 68.98; H, 6.30; N, 4.08; Cl, 10.60.

4b. 3-(2-Bromoethyl)-1-((4-chlorophenyl)methyl)-5-methoxy-2-methylindole

To the product of Example 4a (160 mg, 0.5 mmol) in toluene (1 mL) was added $PBr_3$ (17 μL, 0.18 mmol). The reaction mixture was heated to 100° C. for 10 min then cooled to room temperature. The mixture was partitioned between EtOAc and 1N HCl. The aqueous layer was extracted with EtOAc (1×10). The combined organic layers were washed with H₂O (1×10), brine (2×10), dried over Na₂SO₄, and evaporated. This gave the title compound (170 mg, 87%) which solidified on standing. This material was used in the next reaction without further purification. ¹H-NMR (300 MHz, CDCl₃) δ 7.24 (d, J=8.4 Hz, 2H), 7.06 (d, J=9.1 Hz, 1H), 6.99 (d, J=2.4 Hz, 1H), 6.86 (d, J=8.4 Hz, 2H), 6.78 (dd, J=2.4 and 8.8 Hz, 1H), 5.23 (s, 2H), 3.87 (s, 3H), 3.56 (t, J=7.5 Hz, 2H), 3.28 (t, J=7.5 Hz, 2H), 2.29 (s, 3H).

4c. (2-(1-((4-Chlorophenyl)methyl)-5-methoxy-2-methylindol-3-yl)ethyl)nitrooxy The product of Example 4b (170 mg, 0.43 mmol) was dissolved in CH₃CN (6 mL). Addition of AgNO₃ (85 mg, 0.5 mmol) caused immediate formation of a precipitate. After 20 min, the reaction mixture was filtered through Celite and concentrated. The residue was purified by chromatography on silica gel eluting with 5:1 Hex:EtOAc. This gave the title compound (90 mg, 56%) as a white crystalline solid. mp 94–95° C. ¹H-NMR (300 MHz, CDCl₃) δ 7.23 (d, J=8.5 Hz, 2H), 7.07 (d, J=8.9 Hz, 1H), 6.99 (d, J=2.4 Hz, 1H), 6.86 (d, J=8.4 Hz, 2H), 6.79 (dd, J=2.4 and 8.4 Hz, 1H), 5.23 (s, 2H), 4.60 (t, J=7.2 Hz, 2H), 3.87 (s, 3H), 3.14 (t, J=7.3 Hz, 2H), 2.28 (s, 3H); mass spectrum (API-TIS): m/z 375 (MH⁺). Anal calcd for C₁₉H₁₉ClN₂O₄: C, 60.88; H, 5.11; N, 7.47; Cl, 9.46. Found: C, 60.89; H, 5.23; N, 7.36; Cl, 9.58.

Example 5

1-(3-(4-Fluorophenyl)-7-(nitrooxymethyl)(3a-hydroimidazolo(1,2-a)pyridin-2-yl))-4-(methylsulfonyl)benzene

5a. 1-(3-(4-Fluorophenyl)-7-(hydroxymethyl)(3a-hydroimidazolo(1,2-a)pyridin-2-yl))-4-(methylsulfonyl)benzene This compound was prepared according to a procedure described in patent application WO 96/31509, (the disclosure of which is incorporated by reference herein in its entirety), Example 15. ¹H-NMR (300 MHz, CDCl₃) δ 7.80–7.87 (m, 5H), 7.40–7.46 (m, 2H), 7.20–7.33 (m, 3H), 6.82–6.86 (t, 2H, J=7.0 Hz), 5.11 (s, 2H), 3.04 (s, 3H; mass spectrum (API-TIS) m/z 397 (MH⁺).

5b. 1-(3-(4-Fluorophenyl)-7-(nitrooxymethyl)(3a-hydroimidazolo(1,2-a)pyridin-2-yl))-4-(methylsulfonyl)benzene A suspension of the product of Example 5a (210 mg, 0.52 mmol) was added to an ice-cold mixture of acetic anhydride (393 µL, 4.16 mmol) and nitric acid (110 µL, 2.61 mmol). The resulting mixture was allowed to warm up to 10° C. and stirred for 1 hour. The mixture was then diluted with methylene chloride, washed with cold saturated sodium bicarbonate solution and brine, dried over anhydrous sodium sulfate and concentrated in vacuo. The residue was suspended in hexane/ethyl acetate (2:1) mixture and filtered to give 230 mg (99% yield) of the title compound as a yellow-orange solid. m.p. 145–147° C. ¹H-NMR (300 MHz, CDCl₃) δ 8.07–8.12 (d, 1 H, J=7.0 Hz), 7.82–7.56 (m, 4 H), 7.48–7.56 (m, 2 H), 7.32–7.39 (m, 2 H), 6.95–7.01 (t, 1 H, J=7.0 Hz), 5.96 (s, 2 H), 3.12 (s, 3 H).

Example 6

Ethyl 6-chloro-8-((nitrooxy)methyl)-2-(trifluoromethyl)-2H-chromene-3 carboxylate

6a. Ethyl 6-chloro-8-formyl-2-(trifluoromethyl)-2H-chromene-3 carboxylate

This compound was synthesized as described in patent application WO 98/47890, (the disclosure of which is incorporated by reference herein in its entirety), Example 76. ¹H-NMR (300 MHz, CDCl₃) δ 10.39 (s, 1H), 7.79 (s, 1H), 7.69 (s, 1H), 7.40 (s, 1H), 5.86 (q, J=6.6 Hz, 1H), 4.31–4.44 (mult, 2H), 1.37 (t, J=7.1 Hz, 3H); ¹³C-NMR (75 MHz, CDCl₃) δ 186.3, 163.0, 153.5, 134.4, 134.1, 130.1, 128.4, 125.0, 124.8, 121.8, 121.0, 119.2, 71.1 (q, $J_{C-F}$=134 Hz), 62.0, 14.1.

6b. Ethyl 6-chloro-8-(hydroxymethyl)-2-(trifluoromethyl)-2H-chromene-3 carboxylate Na(OAc)₃BH (2.4 g, 11.2 mmol) was added to a stirred solution of the product of Example 6a (1.5 g, 4.5 mmol) in CH₂Cl₂ (50 mL) and the resulting solution was stirred at room temperature for 3 days. The solution was poured into water (100 mL), the CH₂Cl₂ layer was separated and the aqueous layer was extracted with CH₂Cl₂ (2×25 mL). The combined organic layers were dried over Na₂SO₄. The solvent was evaporated under reduced pressure and the crude material was chromatographed on silica gel eluting with EtOAc:Hexane (1:5) to give the title compound (1.2 g, 79%) as a white solid. mp 98–100° C. ¹H-NMR (300 MHz, CDCl₃) 7.66 (s, 1H), 7.41 (d, J=2.3 Hz, 1H), 7.16 (d, J=2.4 Hz, 1H), 5.76 (q, J=6.7 Hz, 1H), 4.71 (d, J=5.5 Hz, 2H), 4.26–4.70 (mult, 2H), 2.06–2.10 (br mult, 1H), 1.15–1.21 (mult, 3H); ¹³C-NMR (75 MHz, CDCl₃) δ 163.4, 146.7, 135.7, 131.2, 130.3, 127.7, 127.6, 121.3, 120.1, 118.0, 70.6 (q, $J_{C-F}$=133 Hz), 61.7, 59.6, 14.1; mass spectrum (API-TIS) m/z 354 (M+NH₄⁺). Anal. Calcd for C₁₄H₁₂ClF₃O₄: C, 49.94; H, 3.59; F, 16.93; Cl, 10.53. Found: C, 49.83; H, 3.52; F, 17.10; Cl, 10.77.

6c. Ethyl 6-chloro-8-((nitrooxy)methyl)-2-(trifluoromethyl)-2H-chromene-3 carboxylate Fuming HNO₃ (340 µL, 3.6 mmol) was added to a stirred solution of acetic anhydride (1.12 mL, 11.8 mmol) in EtOAc (10 mL) at 0° C. via syringe. The mixture was allowed to stir for 5 min at 0° C. The product of Example 6b. (0.5 g, 1.49 mmol) in EtOAc (10 mL) was then added and stirred for 15 min at 0° C. The reaction mixture was poured into ice cold saturated NaHCO₃ (25 mL) and shaken well. The organic layer was separated and dried over Na₂SO₄. The solvent was evaporated under reduced pressure to afford a viscous oil which was dissolved in hexane (15 mL). The resulting solution was left in a freezer at −20° C. for 12 hours to give the title compound (0.44 g, 77%). mp 53° C. ¹H-NMR (300 MHz, CDCl₃) δ 7.65 (s, 1H), 7.34 (d, J=2.4 Hz, 1H), 7.25 (d, J=2.4 Hz, 1H), 5.78 (q, J=6.6 Hz, 1H), 5.46 (s, 2H), 4.28–4.38 (mult, 3H), 1.35 (t, J=7.1 Hz, 3H); ¹³C-NMR (75 MHz, CDCl₃) δ 163.0, 150.0, 135.0, 133.0, 130.0, 127.6, 125.0, 121.8, 121.1, 120.8, 118.8, 71.3 (q, $J_{C-F}$=133 Hz), 68.0, 61.8, 14; mass spectrum (API-TIS) m/z 399 (M+NH₄⁺). Anal. Calcd for C₁₄H₁₁ClF₃O₆: C, 44.06; H, 2.90; F, 14.93; Cl, 9.29; N, 3.67. Found: C, 44.00; H, 2.85; F, 14.83; Cl, 9.14; N, 3.57.

Example 7

2-(1-((4-Chlorophenyl)carbonyl)-5-methoxy-2-methylindol-3-yl)-N-(2-methyl-2-(nitrosothio)propyl)acetamide

7a. 2-(1-((4-Chlorophenyl)carbonyl)-5-methoxy-2-methylindol-3-yl)-N-(2-methyl-2-sulfanylpropyl)acetamide A solution of indomethacin (3.6 g, 10 mmol) and $Et_3N$ (1.5 mL, 11 mmol) in THF (50 mL) was cooled to 0° C. i-Butyl chloroformate (1.5 mL, 11 mmol) was added dropwise and the reaction was allowed to stir for 20 min. To the resulting solution was added a slurry of 1-amino-2-methyl-2-propanethio.HCl (1.4 g, 10 mmol) and $Et_3N$ (1.5 mL, 11 mmol) in DMF (20 mL). The reaction mixture was kept cold for 2 hours, warmed to room temperature and stirred for 1 hour. The mixture was partitioned between $Et_2O$ and dilute HCl. The organic layer was separated and washed with saturated $NaHCO_3$, brine, filtered and dried over $Na_2SO_4$. Evaporation of the solvent gave a residue which was recrystallized from EtOAc to give the title compound (1.1 g, 25%) as a white solid. mp 177–178° C. $^1$H-NMR (300 MHz, $CDCl_3$) δ 7.67 (d, J=8.5 Hz, 2H), 7.48 (d, J=8.4 Hz, 2H), 6.92 (d, J=2.3 Hz, 1H), 6.91 (d, J=9.0 Hz, 1H), 6.71 (dd, J=2.5 and 9.1 Hz, 1H), 6.10 (br t, J=6.3 Hz, 1H), 3.83 (s, 3H), 3.69 (s, 2H), 3.27 (d, J=6.3 Hz, 2H), 2.42 (s, 3H), 1.36 (s, 1H), 1.26 (s, 6H); mass spectrum (API-TIS) m/z 445 (447) MH$^+$ (1-Cl).

7b. 2-(1-((4-Chlorophenyl)carbonyl)-5-methoxy-2-methylindol-3-yl)-N-(2-methyl-2-(nitrosothio)propyl)acetamide The product of Example 7a (25 mg, 0.056 mmol) was dissolved in $CH_2Cl_2$ (1 mL) and cooled to 0° C. A solution of t-BuONO (7.5 µL, 0.056 mmol) in $CH_2Cl_2$ was added dropwise. The reaction mixture was allowed to warm to room temperature with stirring for 30 min. Evaporation of the solvent gave the title compound (25 mg, 100%) as a green crystalline solid. mp 122–125° C. dec. $^1$H-NMR (300 MHz, $CDCl_3$) δ 7.64 (d, J=8.5 Hz, 2H), 7.51 (d, J=8.4 Hz, 2H), 6.84 (d, J=9.1 Hz, 1H), 6.82 (d, J=2.5 Hz, 1H), 6.78 (dd, J=2.5 and 9.1 Hz, 1H), 5.96 (br t, J=6.4 Hz, 1H), 3.97 (d, J=6.4 Hz, 2H), 3.79 (s, 3H), 3.67 (s, 2H), 2.32 (s, 3H), 1.78 (s, 6H); mass spectrum (API-TIS) m/z 491(493) M+NH$^+$ (1-Cl).

Example 8

Ethyl (2Z)-3-(4-chlorophenyl)-3-(4-(methylsulfonyl)phenyl)-2-(2-(nitrooxy)ethyl)prop-2-enoate

8a. Ethyl (2Z)-3-(4-chlorophenyl)-2-(2-hydroxyethyl)-3-(4-(methylsulfonyl)phenyl) prop-2-enoate This compound was synthesized as described in U.S. Pat. No. 5,807,873, (the disclosure of which is incorporated by reference herein in its entirety), Example 64. mp 126° C. $^1$H-NMR (300 MHz, $CDCl_3$) δ 7.93 (dd, J=1.75 and 8.3 Hz, 2H), 7.46 (dd, J=1.78 and 6.7 Hz, 2H), 7.25–7.30 (mult, 2H), 7.04–7.09 (mult, 2H), 4.01 (q, J=7.1 Hz, 2H), 3.76 (t, J=6.2 Hz, 2H), 3.09 (s, 3H), 2.62 (t, J=6.1 Hz, 2H), 0.97 (t, J=7.1 Hz, 3H); $^{13}$C NMR (75 MHz, $CDCl_3$) δ 170.2, 145.6, 144.6, 140.0, 139.5, 134.2, 132.7, 130.3, 129.9, 128.5, 127.6, 61.3, 61.1, 44.4, 35.0, 13.6; mass spectrum (API-TIS) m/z 409 (MH$^+$), 426 (MNH$_4^+$). Anal. Calcd for $C_{20}H_{21}ClO_5S$: C, 58.75; H, 5.18; Cl, 8.67; S, 7.84. Found: C, 58.64; H, 5.02; Cl, 8.80; S, 7.79.

8b. Ethyl (2Z)-3-(4-chlorophenyl)-3-(4-(methylsulfonyl)phenyl)-2-(2-(nitrooxy)ethyl)prop-2-enoate A suspension of the product of Example 8a (2.02 g, 4.95 mmol) in $CHCl_3$ (20 mL) was added dropwise to a mixture of acetic anhydride (3.71 mL, 4.04 g, 39.6 mmol) and 90% fuming nitric acid (1.03 mL, 1.56 g, 24.8 mmol) at −12° C. The resultant solution was stirred at −12° C. for 1 hour. $CH_2Cl_2$ (30 mL) was added, washed with ice cold saturated $NaHCO_3$, dried over $Na_2SO_4$ and filtered. Evaporation of the solvent gave a residue that was recrystallized from 1:2 Hexane:$CH_2Cl_2$ to give the title compound (1.82 g, 82%) as a white solid. mp 127–128° C. $^1$H-NMR (300 MHz, $CDCl_3$) δ 7.97 (d, J=8.3 Hz, 2H), 7.41 (d, J=7.8 Hz, 2H), 7.27–7.31 (mult, 2H), 7.03–7.08 (mult, 2H), 4.59 (t, J=6.4 Hz, 2H), 4.02 (q, J=7.1 Hz, 2H), 3.09 (s, 3H), 2.76 (t, J=6.4 Hz, 2H), 0.98 (t, J=7.1 Hz, 3H); $^{13}$C NMR (75 MHz, $CDCl_3$) δ 168.8, 147.6, 145.3, 140.5, 139.2, 134.6, 129.9, 129.8, 129.4, 128.7, 128.0, 70.8, 61.4, 44.5, 29.9, 13.6; mass spectrum (API-TIS) m/z 471 (MNH$_4^+$). Anal. Calcd for $C_{20}H_{20}ClNO_7S$: C, 52.92; H, 4.44; N, 3.09; Cl, 7.81; S, 7.06. Found: C, 52.91; H, 4.35; N, 2.93; Cl, 7.89, S, 7.20.

Example 9

(2Z)-3-(4-Chlorophenyl)-3-(4-(methylsulfonyl)phenyl)-2-(2-(nitrooxy)ethyl)prop-2-enoic acid

9a. (2Z)-3-(4-Chlorophenyl)-2-(2-hydroxyethyl)-3-(4-(methylsulfonyl)phenyl)prop-2-enoic acid NaOH (6.4 mL of 1.5 N, 0.38 g, 9.6 mmol) was added dropwise to a solution of

8a. Ethyl (2Z)-3-(4-chlorophenyl)-2-(2-hydroxyethyl)-3-(4-(methylsulfonyl)phenyl) prop-2-enoate This compound was synthesized as described in U.S. Pat. No. 5,807,873, (the disclosure of which is incorporated by reference herein in its entirety), Example 64. mp 126° C. $^1$H-NMR (300 MHz, $CDCl_3$) δ 7.93 (dd, J=1.75 and 8.3 Hz, 2H), 7.46 (dd, J=1.78 and 6.7 Hz, 2H), 7.25–7.30 (mult, 2H), 7.04–7.09 (mult, 2H), 4.01 (q, J=7.1 Hz, 2H), 3.76 (t, J=6.2 Hz, 2H), 3.09 (s, 3H), 2.62 (t, J=6.1 Hz, 2H), 0.97 (t, J=7.1 Hz, 3H); $^{13}$C NMR (75 MHz, $CDCl_3$) δ 170.2, 145.6, 144.6, 140.0, 139.5, 134.2, 132.7, 130.3, 129.9, 128.5, 127.6, 61.3, 61.1, 44.4, 35.0, 13.6; mass spectrum (API-TIS) m/z 409 (MH$^+$), 426 (MNH$_4^+$). Anal. Calcd for $C_{20}H_{21}ClO_5S$: C, 58.75; H, 5.18; Cl, 8.67; S, 7.84. Found: C, 58.64; H, 5.02; Cl, 8.80; S, 7.79.

8b. Ethyl (2Z)-3-(4-chlorophenyl)-3-(4-(methylsulfonyl)phenyl)-2-(2-(nitrooxy)ethyl)prop-2-enoate A suspension of the product of Example 8a (2.02 g, 4.95 mmol) in $CHCl_3$ (20 mL) was added dropwise to a mixture of acetic anhydride (3.71 mL, 4.04 g, 39.6 mmol) and 90% fuming nitric acid (1.03 mL, 1.56 g, 24.8 mmol) at −12° C. The resultant solution was stirred at −12° C. for 1 hour. $CH_2Cl_2$ (30 mL) was added, washed with ice cold saturated $NaHCO_3$, dried over $Na_2SO_4$ and filtered. Evaporation of the solvent gave a residue that was recrystallized from 1:2 Hexane:$CH_2Cl_2$ to give the title compound (1.82 g, 82%) as a white solid. mp 127–128° C. $^1$H-NMR (300 MHz, CDCl$_3$) δ 7.97 (d, J=8.3 Hz, 2H), 7.41 (d, J=7.8 Hz, 2H), 7.27–7.31 (mult, 2H), 7.03–7.08 (mult, 2H), 4.59 (t, J=6.4 Hz, 2H), 4.02 (q, J=7.1 Hz, 2H), 3.09 (s, 3H), 2.76 (t, J=6.4 Hz, 2H), 0.98 (t, J=7.1 Hz, 3H); $^{13}$C NMR (75 MHz, CDCl$_3$) δ 168.8, 147.6, 145.3, 140.5, 139.2, 134.6, 129.9, 129.8, 129.4, 128.7, 128.0, 70.8, 61.4, 44.5, 29.9, 13.6; mass spectrum (API-TIS) m/z 471 (MNH$_4^+$). Anal. Calcd for C$_{20}$H$_{20}$ClNO$_7$S: C, 52.92; H, 4.44; N, 3.09; Cl, 7.81; S, 7.06. Found: C, 52.91; H, 4.35; N, 2.93; Cl, 7.89, S, 7.20.

Example 9

(2Z)-3-(4-Chlorophenyl)-3-(4-(methylsulfonyl)phenyl)-2-(2-(nitrooxy)ethyl)prop-2-enoic acid 9a. (2Z)-3-(4-Chlorophenyl)-2-(2-hydroxyethyl)-3-(4-(methylsulfonyl)phenyl)prop-2-enoic acid NaOH (6.4 mL of 1.5 N, 0.38 g, 9.6 mmol) was added dropwise to a solution of the product of Example 8a (3.62 g, 8.87 mmol) in EtOH (80 mL) at 0° C. The resultant pale yellow solution was stirred at room temperature for 2 hours. The residue, after evaporation of the solvent, was dissolved in water and washed with EtOAc. Crushed ice was added to the aqueous layer which was then acidified with 10% HCl to ~pH=4 and extracted with EtOAc. The organic layer was dried over Na$_2$SO$_4$ and filtered. Evaporation of the solvent gave a residue that was recrystallized from EtOAc:Hex:CH$_2$Cl$_2$ to give the title compound (2.79 g, 82%) as a white solid. mp 144–145° C. $^1$H-NMR (300 MHz, CDCl$_3$/MeOH-d$_4$) δ 7.98 (d, J=7.1 Hz, 2H), 7.53 (d, J=7.0 Hz, 2H), 7.29–7.32 (mult, 2H), 7.16–7.19 (mult, 2H), 3.71 (t, J=6.9 Hz, 2H), 3.15 (s, 3H), 2.56 (t, J=6.8 Hz, 2H); $^{13}$C NMR (75 MHz, CDCl$_3$) δ 173.1, 147.4, 145.1, 141.4, 141.2, 134.9, 134.3, 131.4, 131.3, 129.4, 128.7, 61.3, 61.3, 44.3, 36.3; mass spectrum (API-TIS) m/z 363 (M—H$_2$O), 381 (MH$^+$), 398 (MNH$_4^+$). Anal. Calcd for C$_{18}$H$_{17}$ClO$_5$S: C, 56.77; H, 4.50; Cl, 9.31; S, 8.42. Found: C, 56.64; H, 4.44; Cl, 9.40; S, 8.18.

9b. (2Z)-3-(4-Chlorophenyl)-3-(4-(methylsulfonyl) phenyl)-2-(2-(nitrooxy)ethyl) prop-2-enoic acid A suspension of the product of Example 9a (1.37 g, 3.66 mmol) in CHCl$_3$ (54 mL) was added dropwise to a mixture of acetic anhydride (2.72 mL, 2.94 g, 28.8 mmol) and 90% fuming nitric acid (0.76 mL, 1.14 g, 18.0 mmol) at −12° C. The resultant solution was stirred at −12° C. for 30 min. CH$_2$Cl$_2$ (25 mL) was added, washed with water, dried over Na$_2$SO$_4$ and filtered. Evaporation of the solvent gave a residue that was recrystallized from EtOAc:Hexane:CH$_2$Cl$_2$ to give the title compound (0.9 g, 59%) as a white solid. mp 143–144° C. $^1$H-NMR (300 MHz, CDCl$_3$) δ 7.98 (d, J=8.2 Hz, 2H), 7.40 (d, J=8.2 Hz, 2H), 7.27–7.32 (mult, 2H), 7.07–7.11 (mult, 2H), 4.61 (t, J=6.3 Hz, 2H), 3.10 (s, 3H), 2.78 (t, J=6.3 Hz, 2H); $^{13}$C NMR (75 MHz, CDCl$_3$) δ 172.8, 150.9, 145.4, 140.7, 138.7, 135.1, 129.8, 129.7, 129.0, 128.1, 127.7, 70.8, 44.5, 30.0; mass spectrum (API-TIS) m/z 443 (MNH$_4^+$). Anal. Calcd for C$_{18}$H$_{16}$ClNO$_7$S: C, 50.77; H, 3.79; N, 3.29; Cl, 8.33; S, 7.53. Found: C, 50.87; H, 3.67; N, 3.13; Cl, 8.26, S, 7.43.

Example 10

(2Z)-3-(4-Chlorophenyl)-2-(2-hydroxyethyl)-N-(2-methyl-2(nitrosothio)propyl)-3-(4-(methylsulfonyl) phenyl)prop-2-enamide 10a. (2Z)-3-(4-Chlorophenyl)-N-(2-methyl-2-sulfanylpropyl)-3-(4-(methylsulfonyl)phenyl)-2-(2-(1,1,2,2,-tetramethyl-1-silapropoxy)ethyl)prop-2-enamide To a solution of the product of Example 9a (0.5 g, 1.32 mmol) and imidazole (0.18 g, 2.63 mmol) in dry THF (10 mL) was added a solution of t-butyldimethyl-chlorosilane (0.4 g, 2.63 mmol) in dry THF (10 mL) dropwise at room temperature. The resulting white suspension was stirred at room temperature for 16 hours. The reaction mixture was partitioned between EtOAc and saturated NaHCO$_3$. The organic layer was separated, washed with 10% HCl, dried over Na$_2$SO$_4$, filtered and concentrated in vacuo to give 1:1 mono:disilylated product as a white foam which was used in the next step without further purification. Mass spectrum (API-TIS) m/z 495 and 609 (MH$^+$). The entire white foam was dissolved in THF (10 mL). Bis(2-oxo-3-oxazolidinyl) phosphonic chloride (0.70 g, 1.58 mmol) and 4-(dimethylamino)pyridine (0.16 g, 1.32 mmol) were added at room temperature. After 5 min, 1-amino-2-methyl-2-propanethiol (0.15 g, 1.41 mmol) in THF (2 mL) was added dropwise. The resulting pale yellow solution was stirred at room temperature for 2.5 hours. Evaporation of the solvent gave a residue that was chromatographed on silica gel eluting with 1:1 EtOAc:Hexane to give the title compound (0.28 g, 37%) as a white foam. $^1$H-NMR (300 MHz, CDCl$_3$) δ 7.90 (d, J=8.3 Hz, 2H), 7.56 (d, J=8.3 Hz, 2H), 7.29 (d, J=8.4 Hz, 2H), 7.15 (d, J=6.7 Hz, 2H), 5.91 (t, J=6.2 Hz, 1H), 3.77 (t, J=5.9 Hz, 2H), 3.15 (d, J=6.2 Hz, 2H), 3.09 (s, 3H), 2.64 (t, J=5.9 Hz, 2H), 1.28 (s, 1H), 1.11 (s, 6H), 0.96 (s, 9H), 0.09 (s, 6H); $^{13}$C NMR (75 MHz, CDCl$_3$) δ 170.2, 145.9, 140.2, 139.8, 139.4, 137.9, 134.4, 130.9, 130.6, 129.1, 127.4, 60.6, 60.4, 53.5, 52.7, 44.6, 44.5, 35.0, 29.9, 26.1, 21.1, 18.4, 14.3, −5.2; mass spectrum (API-TIS) m/z 582 (MH$^+$). Anal. Calcd for C$_{28}$H$_{40}$ClNO$_4$S$_2$Si: C, 57.76; H, 6.92; N, 2.41. Found: C, 57.79; H, 6.67; N, 2.30.

10b. (2Z)-3-(4-Chlorophenyl)-2-(2-hydroxyethyl)-N-(2-methyl-2-sulfanylpropyl)-3-(4-(methylsulfonyl)phenyl)prop-2-enamide To a solution of the product of Example 10a (225 mg, 0.39 mmol) in THF (13 mL) was added dropwise trifluoroacetic acid (129 μL, 1.67 mmol) at 0° C. To this was added tetrabutylammonium fluoride (385 μL of 1M solution in THF, 0.39 mmol) dropwise. The resultant solution was gradually warmed to room temperature and stirred for 25 hours. The reaction mixture was partitioned between EtOAc (50 mL) and ice cold 1% HCl. The organic layer was separated, dried over Na$_2$SO$_4$ and filtered. The solvent was evaporated and the residue was chromatographed on silica gel eluting with 5% MeOH:CH$_2$Cl$_2$ to give the title compound (175 mg, 97%) as a white foam. mp 62–64° C. $^1$H-NMR (300 MHz, CDCl$_3$) δ 7.93 (d, J=8.2 Hz, 2H), 7.47 (d, J=8.2 Hz, 2H), 7.28 (d, J=8.5 Hz, 2H), 7.16 (d, J=8.4 Hz, 2H), 6.05 (t, J=6.1 Hz, 1H), 3.72 (t, J=5.7 Hz, 2H), 3.14 (d, J=6.1 Hz, 2H), 3.09 (s, 3H), 2.59 (t, J=5.7 Hz, 2H), 1.36 (s, 1H), 1.16 (s, 6H); $^{13}$C NMR (75 MHz, CDCl$_3$) δ 171.1, 145.8, 141.1, 140.0, 138.8, 137.3, 134.7, 130.5, 130.4, 129.2, 127.8, 61.0, 52.9, 44.7, 44.6, 34.9, 30.0; mass spectrum (API-TIS) m/z 468 (MH$^+$).

10c. (2Z)-3-(4-Chlorophenyl)-2-(2-hydroxyethyl)-N-(2-methyl-2-(nitrosothio)propyl)-3-(4-(methylsulfonyl)phenyl)prop-2-enamide To a solution of t-butyl nitrite (0.2 mL of 90% solution, 158 mg, 1.53 mmol) in 1:1 MeOH:CH$_2$Cl$_2$ (1.2 mL) was added dropwise a solution of the product of Example 10b (156 mg, 0.33 mmol) in 1:1 MeOH:CH$_2$Cl$_2$ (2 mL) at 0° C. The resultant solution was stirred at 0° C. in the dark for 30 min. Additional-t-butyl nitrite (0.15 mL of 90% solution, 118 mg, 1.15 mmol) was added and the resultant green solution was stirred at 0° C. for a further 30 min and then at room temperature for 20 min. The volatiles were removed in vacuo and the residue was chromatographed on silica gel eluting with 1:1 EtOAc:CH$_2$Cl$_2$ to give the title compound (96 mg, 58%) as a green solid. mp 150–153° C. $^1$H-NMR (300 MHz, CDCl$_3$) δ 7.90 (d, J=8.3 Hz, 2H), 7.45 (d, J=8.4 Hz, 2H), 7.24 (dd, J=1.9 and 6.6 Hz, 2H), 7.09–7.12 (mult, 2H), 6.40 (br t, J=6.3 Hz, 1H), 3.86 (J=6.3 Hz, 2H), 3.66 (t, J=5.9 Hz, 2H), 3.09 (s, 3H), 2.54 (t, J=5.8 Hz, 2H), 1.67 (s, 6H), $^{13}$C NMR (75 MHz, CDCl$_3$) δ 171.4, 145.8, 141.2, 139.8, 138.8, 136.9, 134.5, 130.5, 130.3, 129.0, 127.6, 60.5, 56.5, 44.5, 34.7, 26.8; mass spectrum (API-TIS) m/z 467 (M–NO), 497 (MH$^+$).

Example 11

1-(5-methyl-1-(2-methyl-2-(nitrosothio)propyl)pyrrol-2-yl)-4-(methylsulfonyl)benzene

11a. 1-(4-Methylthiophenyl)pentane-1,4-dione 4-(Methylthio)benzaldehyde (20 mL, 150 mmol), 3-benzyl-5-(2-hydroxyethyl)-4-methylthiazolium chloride (7 g, 30 mmol), methyl vinyl ketone (15 mL, 180 mmol), and Et$_3$N (21 mL, 150 mmol) were placed in a flask and immersed in an oil bath at 80° C. The initial purple colored solution became orange over 30 min. The solution was cooled to room temperature, EtOAc (30 mL) was added to precipitate the thiazolium salt which was removed by filtration. The filter cake was washed with hot EtOAc (2×30 mL). The combined mother liquor and washes were concentrated to give 43 g of residue. The residue was taken up in hot 1:1 Hexane:EtOAc (100 mL), which upon cooling deposited a solid. This solid was isolated on a glass frit and washed with hot 4:1 Hexane:EtOAc (50 mL). From this hot wash was deposited the title compound (16.4 g, 49%) as a tan solid. mp 72–73° C. $^1$H-NMR (300 MHz, CDCl$_3$) δ 7.88 (d, J=8.4 Hz, 2H), 7.25 (d, J=8.4 Hz, 2H), 3.22 (t, J=6.5 Hz, 2H), 2.87 (t, J=6.2 Hz, 2H), 2.51 (s, 3H), 2.24 (s, 3H); mass spectrum (API-TIS) m/z 223 (MH$^+$). Anal. Calcd. for C$_{12}$H$_{14}$O$_2$S: C, 64.84; H, 6.35; S, 14.42. Found C, 64.68; H, 6.19; S, 14.24.

11b. 1-(4-(Methylsulphonyl)phenyl)pentane-1,4-dione

The product of Example 11a (16.4 g, 74 mmol) was dissolved in CH$_2$Cl$_2$ (300 mL) and cooled to 0° C. Solid 70% m-chloroperbenzoic acid (37 g, 150 mmol) was added portionwise over 5 min. After complete addition the cold bath was removed and the reaction mixture was allowed to warm to room temperature with stirring for 3 hours. The precipitate that had formed was removed by filtration and washed with CH$_2$Cl$_2$ (2×50 mL). The combined organic filtrates were washed with 1M Na$_2$CO$_3$, dried over Na$_2$SO$_4$, and concentrated. The residue was partitioned between EtOAc (200 mL) and 1M Na$_2$CO$_3$ (50 mL). The solid was kept with the aqueous layer and the mixture was extracted with EtOAc (50 mL). The aqueous layer was filtered to give the title compound (8.9 g) after drying in vacuo. The combined organic layers were washed with water, brine, dried over Na$_2$SO$_4$, and concentrated to give additional title compound (6.5 g). Overall yield of the title compound was 15.4 g, 82%. mp 132–133° C. $^1$H-NMR (300 MHz, CDCl3) δ 8.15 (d, J=8.4 Hz, 2H), 8.05 (d, J=8.3 Hz, 2H), 3.27 (t, 6.6 Hz, 2H), 3.07 (s, 3H), 2.93 (t, J=6.4 Hz, 2H), 2.26 (s, 3H); mass spectrum (API-TIS) m/z 255 (MH+). Anal. Calcd. for C$_{12}$H$_{14}$O$_4$S: C, 56.68; H, 5.55; S, 12.61. Found: C, 56.39; 5.40; S, 13.36.

11c. 1-(5-Methyl-1-(2-methyl-2-sulfanylpropyl)pyrrol-2-yl)-4-(methylsulfonyl)benzene The product of Example 11b (2 g, 7.9 mmol), NaOAc (1.3 g, 16 mmol), and 1-amino-2-methyl-2-propanethiol.HCl (1.2 g, 8.7 mmol) were added to HOAc (15 mL) and heated to 80° C. for 3 hours. The reaction mixture was cooled to room temperature and the HOAc was removed at reduced pressure. The residue was partitioned between EtOAc (40 mL) and 1N Na$_2$CO$_3$ (15 mL). The organic layer was separated and washed with 1N Na$_2$CO$_3$, brine, then dried over Na$_2$SO$_4$ and concentrated. The residue was crystallized from hot MeOH (5 mL) to gave the title compound (1.6 g, 63%) as an orange-tan solid. mp 124–126° C. $^1$H-NMR (300 MHz, CDCl$_3$) δ 7.93 (d, J=8.4 Hz, 2H), 7.52 (d, J=8.4 Hz, 2H), 6.22 (d, J=3.6 Hz, 1H), 6.03 (d, J=3.6 Hz, 1H), 4.24 (br, 2H), 3.08 (s, 3H), 2.41 (s, 3H), 1,55 (s, 1H), 1.04 (s, 6H); mass spectrum (API-TIS) m/z 324 (MH+).

11d. 1-(5-Methyl-1-(2-methyl-2-(nitrosothio)propyl) pyrrol-2-yl)-4-(methylsulfonyl) benzene The product of Example 11c (100 mg, 0.31 mmol) was dissolved in CH$_2$Cl$_2$ and cooled to 0° C. A solution of t-BuONO (40 mL, 31 mmol) in CH$_2$Cl$_2$ (1 mL) was added dropwise. After complete addition the reaction mixture was warmed to room temperature and allowed to stir 1 hour. The solvent was evaporated and the residue was chromatographed on silica gel eluting with 2:1 Hexane:EtOAc. This gave a 1:3 mixture of starting material and desired product (67 mg, 61%). A small fraction of this mixture was reacted with t-BuONO to give the title compound as a dark foam. $^1$H-NMR (300 MHz, CDCl$_3$) δ 7.89 (d, J=8.5 Hz, 2H), 7.44 (d, J=8.5 Hz, 2H), 6.22 (d, J=3.6 Hz, 1H), 6.05 (d, J=3.5 Hz, 1H), 4.60–5.00 (br, 2H), 3.15 (s, 3H), 2.39 (s, 3H), 1.6–2.0 (br s, 6H); mass spectrum (API-TIS) m/z 353 (MH+).

Example 12

3-(4-(1-Methyl-1-(nitrosothio)ethyl)-2-oxo-1,3-oxazolidin-3 yl) propyl (2Z)-4-acetyloxy-2-(4-fluorophenyl)-3-(4 (methylsulfonyl) phenyl)but-2-enoate

12a. 3-(4-Fluorophenyl)-4-(4-(methylsulfonyl)phenyl)-5-hydrofuran-2-one

This compound was synthesized as described in patent EP 0 788 476 B1, (the disclosure of which is incorporated by reference herein in its entirety), lactone 11. mp 163° C. $^1$H-NMR (300 MHz, CDCl$_3$) δ 7.94 (d, J=8.6 Hz, 2H), 7.51 (d, J=8.5 Hz, 2H), 7.38–7.43 (mult, 2H), 7.06–7.27 (mult, 2H), 5.18 (s, 2H), 3.08 (s, 3H); $^{13}$C NMR (75 MHz, CDCl$_3$)

δ 172.5, 165.0, 161.7, 153.7, 142.2, 136.3, 131.4, 131.3, 128.6, 128.3, 128.0, 125.3, 125.2, 116.4, 116.1, 70.5, 44.4; mass spectrum (API-TIS) m/z 333 (MH$^+$), 350 (MNH$_4^+$). Anal. Calcd for $C_{17}H_{13}FO_4S$: C, 61.44; H, 3.94; F, 5.72; S, 9.65. Found: C, 61.24; H, 3.89; F, 5.70; S, 9.52.

12b. 1-((1Z)-2-(4-Fluorophenyl)-3-hydroxy-1-(hydroxymethyl)prop-1-enyl)-4-(methylsulfonyl)benzene A solution of diisobutylaluminium hydride (70.2 mL, 1M solution in THF, 9.98 g, 70.2 mmol) was added dropwise to a solution of the product of Example 12a (4.68 g, 14.1 mmol) in THF (190 mL) at 0° C. After stirring for 30 min at 0° C. and then 1 hour at room temperature, the mixture was cooled to 0° C. Additional DIBAL (30 mL, 1M solution in THF, 4.27 g, 30 mmol) was added dropwise and stirred for 1 hour at room temperature. This reaction mixture was poured into a solution of 1M sodium potassium tartrate (200 mL) containing MeOH (50 mL). The aqueous mixture was extracted with EtOAc. The organic layer was dried over Na$_2$SO$_4$, and filtered. The solvent was removed in vacuo to give the title compound (4.7 g, 99%) as a colorless oil. $^1$H-NMR (300 MHz, MeOH-d$_4$) δ 7.73 (d, J=8.5 Hz, 2H), 7.35 (d, J=8.5 Hz, 2H), 7.07–7.12 (mult, 2H), 6.85–6.91 (mult, 2H), 4.64 (s, 2H), 4.62 (s, 2H), 3.06 (s, 3H); mass spectrum (API-TIS) m/z 337 (MH$^+$), 354 (MNH$_4^+$).

12c. (2Z)-3-(4-Fluorophenyl)-4-hydroxy-2-(4-(methylsulfonyl)phenyl)but-2-enyl acetate Acetic anhydride (1.33 mL, 1.4 g, 14.0 mmol) was added dropwise to a solution of the product of Example 12b (4.7 g, 14.0 mmol), DMAP (56 mg, 0.46 mmol) and triethylamine (5.89 mL, 42.3 mmol) in CH$_2$Cl$_2$ (600 mL) at room temperature. The mixture was stirred for 1 hour at room temperature, washed with water and dried over Na$_2$SO$_4$. The residue, after evaporation of the solvent, was chromatographed on silica gel eluting with 1:1 to 3:2 EtOAc:Hexane to give the title compound (1.31 g, 25%) as a colorless oil, followed by its regio-isomer, (2Z)-2-(4-fluorophenyl)-4-hydroxy-3-(4-(methylsulfonyl)phenyl)but-2-enyl acetate (1.37 g, 26%) also as a colorless oil. (2Z)-3-(4-fluorophenyl)-4-hydroxy-2-(4-(methylsulfonyl)phenyl)but-2-enyl acetate: $^1$H-NMR (300 MHz, CDCl$_3$) δ 7.73 (d, J=8.4 Hz, 2H), 7.21 (d, J=8.5 Hz, 2H), 7.02–7.06 (mult, 2H), 6.80–6.86 (mult, 2H), 5.17 (s, 2H), 4.63 (s, 2H), 3.01 (s, 3H), 1.99 (s, 3H); $^{13}$C NMR (75 MHz, CDCl$_3$) δ 171.4, 163.6, 160.4, 145.9, 143.6, 139.0, 135.6 (J$_{19F-C}$=3.4 Hz), 134.3, 131.0, 130.9, 130.5, 127.3, 115.5, 115.2, 64.4, 63.4, 44.5, 21.0; mass spectrum (API-TIS) m/z 396 (MNH$_4^+$). (2Z)-2-(4-Fluorophenyl)-4-hydroxy-3-(4-(methylsulfonyl)phenyl)but-2-enyl acetate: $^1$H-NMR (300 MHz, CDCl$_3$) δ 7.70 (d, J=8.4 Hz, 2H), 7.30 (d, J=8.4 Hz, 2H), 6.82–6.97 (mult, 4H), 5.16 (s, 2H), 4.61 (s, 2H), 2.99 (s, 3H), 1.99 (s, 3H); $^{13}$C NMR (75 MHz, CDCl$_3$) δ 171.4, 163.4, 160.1, 146.8, 141.0, 138.5, 136.7, 134.7 (J$_{19F-C}$=3.5 Hz), 131.0, 130.9, 130.1, 126.9, 115.4, 115.1, 64.4, 62.8, 44.3, 20.8; mass spectrum (API-TIS) m/z 396 (MNH$_4^+$).

12d. (2Z)-3-(4-Fluorophenyl)-2-(4-(methylsulfonyl)phenyl)-4-oxobut-2-enyl acetate A mixture of the product of Example 12c (1.31 g, 3.47 mmol) and MnO$_2$ (6.96 g, 80 mmol) in CH$_2$Cl$_2$ (175 mL) was stirred for 16 hours at room temperature and then filtered through a pad of Celite. The filtrate was dried over Na$_2$SO$_4$, filtered and concentrated in vacuo to give the title compound (0.81 g, 62%) as yellow solid. $^1$H-NMR (300 MHz, CDCl$_3$) δ 10.39 (s, 1H), 7.79 (d, J=10.3 Hz, 2H), 7.31 (d, J=12.2 Hz, 2H), 6.88–6.91 (mult, 4H), 5.45 (s, 2H), 3.02 (s, 3H), 2.00 (s, 3H); $^{13}$C NMR (75 MHz, CDCl$_3$) δ 190.9, 170.4, 164.1, 160.8, 149.6, 143.9, 141.3, 140.3, 132.4, 132.3, 130.0, 129.9, 127.4, 115.7, 115.5, 62.1, 44.4, 20.7; mass spectrum (AFI-TIS) m/z 394 (MNH$_4^+$).

12e (2Z)-4-Acetyloxy-2-(4-fluorophenyl)-3-(4-(methylsulfonyl)phenyl)but-2-enoic acid To a solution of the product of Example 12d (0.81 g, 2.15 mmol) and 2-methyl-2-butene (28.9 mL, 19.1 g, 273 mmol) in t-butanol (170 mL), was added a solution of NaClO$_2$ (4.87 g, 53.9 mmol) and NaH$_2$PO$_4$ (4.80 g, 40.1 mmol) in water (10 mL). The mixture was stirred for 2 hours at room temperature. The residue, after evaporation of the solvent, was dissolved in pH=7 buffer solution (250 mL) and extracted with EtOAc. The aqueous layer was acidified with 10% HCl (~pH=4–5) and extracted with EtOAc. The combined organic layers were dried over Na$_2$SO$_4$ and filtered. The residue after evaporation of the solvent was recrystallized from EtOAc:Hex:CH$_2$Cl$_2$ to give the title compound (0.31 g, 37%) as a white solid. mp 187° C. $^1$H-NMR (300 MHz, THF-d$_8$) δ 7.87 (d, J=8.1 Hz, 2H), 7.47 (d, J=8.1 Hz, 2H), 7.21–7.25 (mult, 2H), 6.97–7.03 (mult, 2H), 5.35 (mult, 2H), 3.08 (s, 3H), 1.97 (s, 3H); $^{13}$C NMR (75 MHz, CDCl$_3$) δ 170.8, 169.7, 165.2, 162.0, 144.9, 142.2, 141.9, 137.7, 133.9 (J$_{C-F}$=3.5 Hz), 133.2, 133.1, 131.6, 128.4, 116.3, 116.0, 65.9, 44.5, 20.8; mass spectrum (API-TIS) m/z 333 (M–HOAc), 410 (M+NH$_4^+$). Anal. Calcd for $C_{19}H_{17}FO_6S.1/2H_2O$: C, 56.85; H, 4.52; F, 4.73; S, 7.99. Found: C, 56.83; H, 4.45; F, 5.07; S, 7.94.

12f. 2-Amino-3-methyl-3-((2,4,6-trimethoxyphenyl)methylthio)butanoic acid

A suspension of 2-amino-3-methyl-3-sulfanylbutanoic acid (D-penicillamine) (5.0 g, 34 mmol) in CH$_2$Cl$_2$ (150 mL) was cooled to 0° C. Trifluoroacetic acid (54 mL, 703 mmol) was added dropwise over a period of 5 min. Then 2,4,6-trimethoxy-benzyl alcohol (6.64 g, 34 mmol) in CH$_2$Cl$_2$ (137 mL) was added dropwise at 0° C. with stirring. Stirring was continued for 1 hour at 0° C. and then for 2 hours at room temperature. The solvent was removed in vacuo and the residue was dried under high vacuum for 3 hours. The crude red solid was recrystallized from 1:1:1 CH$_2$Cl$_2$/MeOH/EtOAc to give the title compound (10.5 g, 95%) as a white solid. $^1$H-NMR (300 MHz, CDCl$_3$) δ 6.10 (s, 2H), 3.84 (s, 6H), 3.76 (s, 3H), 3.40–4.10 (m, 3H), 1.69 (s, 3H), 1.23 (s, 3H); mass spectrum (API-TIS) m/z 330 (MH$^+$).

12g. 2-Amino-3-methyl-3-((2,4,6-trimethoxyphenyl)methylthio)butan-1-ol

To a stirred solution of the product of Example 12f (10.5 g, 32 mmol) in THF (80 mL) was added dropwise lithium aluminum hydride (1 M in THF, 64 mL, 64 mmol) at 0° C. under nitrogen. The resulting solution was stirred at 0° C. for 1 hour and then at room temperature for 2 hours. The excess reducing agent was destroyed by careful portionwise addition of Na$_2$SO$_4$.10H$_2$O at 0° C. The granular white precipitate was filtered and washed with 30% methanol in CH$_2$Cl$_2$. The combined filtrate was dried over Na$_2$SO$_4$, filtered and evaporated to give the title compound (7.6 g, 76%) as a yellow oil which was used for the next step without further purification. $^1$H-NMR (300 MHz, CDCl$_3$) δ 6.10 (s, 2H), 3.85 (s, 6H), 3.81 (s, 3H), 3.74 (s, 2H), 3.60–3.80 (mult, 2H), 3.37–3.43 (mult, 1H), 2.93–2.98 (mult, 1H), 1.45 (s, 3H), 1.30 (s, 3H); mass spectrum (API-TIS) m/z 316 (MH$^+$).

12h. 4-(1-Methyl-1-((2,4,6-trimethoxyphenyl)methylthio)ethyl)-1,3-oxazolidin-2-one A mixture of K$_2$CO$_3$ (0.33 g, 2.4 mmol), diethylcarbonate (50 mL) and the product of Example 12g (7.6 g, 24 mmol) was heated at 100° C. for 24 hours. Excess diethylcarbonate was evaporated and the resultant light brown slurry was cooled to room temperature, diluted with CH$_2$Cl$_2$ and filtered to remove the K$_2$CO$_3$. The filtrate was evaporated and the residue was chromatographed on silica gel eluting with 1:1 EtOAc:Hexane to give the title compound 2.6 g (32%) as a viscous yellow oil. $^1$H-NMR (300 MHz, CDCl$_3$) δ 6.13 (s, 2H), 6.07 (bs, 1H), 4.30–4.40 (mult, 1H), 4.25–4.28 (mult, 1H), 4.03–4.08 (mult, 1H), 3.86 (s, 6H), 3.83 (s, 2H), 3.81 (s, 3H), 1.32 (s, 3H), 1.27 (s, 3H); $^{13}$C NMR (75 MHz, CDCl$_3$) δ 160.7, 159.5, 158.7, 106.3, 90.9, 66.5, 59.5, 56.0, 55.5, 47.1, 23.8, 22.3, 20.3; mass spectrum (API-TIS) m/z 342 (MH$^+$), 359 (MNH$_4$$^+$).

12i. 3-Bromo-1-(1,1,2,2-tetramethyl-1-silapropoxy)propane t-Butyldimethylchlorosilane (17.4 g, 115 mmol) in dry THF (50 mL) was added dropwise to a solution of 1,3-bromopropanol (16 g, 115 mmol) and imidazole (7.85 g, 115 mmol) in dry THF (50 mL) at room temperature. The resulting white suspension was stirred at room temperature for 16 hours. The reaction mixture was diluted with EtOAc (200 mL), washed with water, brine, dried over Na$_2$SO$_4$, filtered, and concentrated in vacuo at room temperature to give the title compound 28.5 g (98%) as a colorless volatile liquid. $^1$H-NMR (300 MHz, CDCl$_3$) δ 3.74 (t, J=5.7 Hz, 2H), 3.52 (t, J=6.5 Hz, 2H), 2.02–2.06 (mult, 2H), 0.90 (s, 9H), 0.07 (s, 6H); $^{13}$C NMR (75 MHz, CDCl$_3$) δ 60.6, 35.7, 30.8, 26.1, −5.2.

12j. 4-(1-Methyl-1-((2,4,6-trimethoxyphenyl)methylthio)ethyl)-3-(3-(1,1,2,2-tetramethyl-1-silapropoxy)propyl)-1,3-oxazolidin-2-one NaH (0.84 g, 35.3 mmol) was added portionwise to a solution of the product of Example 12 h (8.03 g, 23.5 mmol) in dry DMF (25 mL) under nitrogen at 0° C. The resulting suspension was stirred at 0° C. for 20 min to give a brown red solution. The product of Example 12i (7.14 g, 28.2 mmol) in DMF (7 mL) was added dropwise and stirred at room temperature for 16 hours and then the solvent was evaporated. The residue was treated with 1:1 EtOAc:water and the organic layer was separated. The aqueous layer was extracted with EtOAc and the combined organic phases were washed with water, dried over Na$_2$SO$_4$, and filtered. Evaporation of the solvent left a residue that was chromatographed on silica gel eluting with 5% to 25% EtOAc:Hexane to give the title compound 6.2 g (51%) as a white foam. $^1$H-NMR (300 MHz, CDCl$_3$) δ 6.11 (s, 2H), 4.38–4.42 (mult, 1H), 4.05–4.11 (mult, 1H), 3.93–3.96 (mult, 1H), 3.83 (s, 6H), 3.80 (s, 3H), 3.77 (s, 2H), 3.65 (t, J=6.1 Hz, 2H), 3.58–3.71 (mult, 1H), 3.34–3.44 (mult, 1H), 1.66–1.96 (mult, 2H), 1.56 (s, 3H), 1.24 (s, 3H), 0.89 (s, 9H), 0.04 (s, 6H); $^{13}$C NMR (75 MHz, CDCl$_3$) δ 160.7, 159.5, 158.7, 107.0, 90.8, 65.7, 61.7, 60.6, 55.9, 54.4, 48.3, 42.6, 30.3, 26.8, 26.0, 22.2, 20.4, 18.4, −5.3; mass spectrum (API-TIS) m/z 514 (MH$^+$).

12k. 3-(3-Hydroxypropyl)-4-(1-methyl-1-sulfanylethyl)-1,3-oxazolidin-2-one

The product of Example 12j (5.0 g, 9.75 mmol) was treated with water (4.0 mL), phenol (4.0 g), anisole (4.0 mL) and finally trifluoroacetic acid (49 mL). The resultant solution was stirred at room temperature for 1 hour. The volatiles were evaporated to give a yellow oil. The crude yellow oil was chromatographed on silica gel eluting with 1:1 EtOAc:Hexane to 5% MeOH:CH$_2$Cl$_2$ to give the title compound 1.4 g (66%) as a pale yellow oil. $^1$H-NMR (300 MHz, CDCl$_3$) δ 4.30–4.35 (mult, 2H), 3.50–3.82 (mult, 5H), 2.80–2.95 (bs, 1H), 1.83–1.89 (mult, 2H), 1.78 (s, 1H), 1.42 (s, 6H); $^{13}$C NMR (75 MHz, CDCl$_3$) δ 160.5, 65.8, 65.4, 59.2, 47.2, 42.2, 30.1, 29.0, 28.0; mass spectrum (API-TIS) m/z 220 (MH$^+$), 237 (MNH$_4$$^+$). Anal. Calcd for C$_9$H$_{17}$NO$_3$S: C, 49.29; H, 7.81; N, 6.39. Found: C, 48.99; H, 7.71; N, 6.04.

12l. 3-(3-Hydroxypropyl)-4-(1-methyl-1-(nitrosothio)ethyl)-1,3-oxazolidin-2-one To a solution of t-BuONO (1.67 mL of 90% solution, 1.32 g, 12.8 mmol) in CH$_2$Cl$_2$ (10 mL) was added dropwise a solution of the product of Example 12k (1.4 g, 6.4 mmol) in CH$_2$Cl$_2$ (16 mL) at 0° C. The resulting green solution was stirred at 0° C. for 1 hour and then at room temperature for 20 min in the dark. Evaporation of the solvent gave a residue that was chromatographed on silica gel eluting with 1:1 EtOAc:CH$_2$Cl$_2$ to 5% MeOH:CH$_2$Cl$_2$ to give the title compound 0.98 g (62%) as a green oil. $^1$H-NMR (300 MHz, CDCl$_3$) δ 4.61–4.66 (mult, 1H), 4.36–4.46 (mult, 2H), 3.42–3.75 (mult, 4H), 2.30–2.45 (br s, 1H), 1.97 (s, 3H), 1.96 (s, 3H), 1.74–1.80 (mult, 2H); $^{13}$C NMR (75 MHz, CDCl$_3$) δ 160.2, 65.3, 63.3, 59.3, 58.8, 42.3, 29.8, 25.4, 25.0; mass spectrum (API-TIS) m/z 219 (M−NO), 249 (MH$^+$), 266 (MNH$_4$$^+$). Anal. Calcd for C$_9$H$_{16}$N$_2$O$_4$S: C, 43.54; H, 6.50; N, 11.28. Found: C, 43.61; H, 6.59; N, 10.99.

12m. 3-(4-(1-Methyl-1-(nitrosothio)ethyl)-2-oxo-1,3-oxazolidin-3-yl)propyl (2Z)-4-acetyloxy-2-(4-flurophenyl)-3-(4-(methylsulfonyl)phenyl)but-2-enoate Bis(2-oxo-3-oxazolidinyl)phosphonic chloride (0.14 g, 0.32 mmol) and 4-(dimethylamino)pyridine (19.0 mg, 0.16 mmol) were added to a solution of the product of Example 12l (100 mg, 0.40 mmol) and the product of Example 12e (61 mg, 0.16 mmol) in THF (2 mL) at 0° C. The resulting solution was stirred at 0° C. for 1 hour and then at room temperature for 20 hours. Evaporation of the solvent gave a residue that was chromatographed on silica gel eluting with 1:1 EtOAc:CH$_2$Cl$_2$ to give the title compound 68 mg (70%) as a green foam. $^1$H-NMR (300 MHz, CDCl$_3$) δ 7.78 (d, J=8.3 Hz, 2H), 7.31 (d, J=8.3 Hz, 2H), 6.99–7.03 (mult, 2H), 6.82–6.88 (mult, 2H), 5.17 (s, 2H), 4.53 –4.57 (mult, 1H), 4.36–4.43 (m, 2H), 4.25 (t, J=6.1 Hz, 2H), 3.64–3.74 (mult, 1H), 3.18–3.28 (mult, 1H), 3.02 (s, 3H), 1.95 (s, 3H), 1.91 (s, 3H), 1.87 (s, 3H), 1.85–2.06 (mult, 2H); mass spectrum (API-TIS) m/z 593 (M−NO), 623 (MH$^+$), 640 (MNH$_4$$^+$).

Example 13

(2Z)-3-(4-Fluorophenyl)-3-(N-methyl-N-(2-methyl-2-(nitrosothio) propyl)carbamoyl)-2-(4-(methylsulfonyl)phenyl) prop-2-enyl acetate

13a. (2Z)-3-(4-Fluorophenyl)-3-(N-methyl-N-(2-methyl-2-sulfanylpropyl)carbamoyl)-2-(4-(methylsulfonyl)phenyl)prop-2-enyl acetate Bis(2-oxo-3-oxazolidinyl)phosphonic chloride (0.242 g, 0.55 mmol) was added to a solution of the product of Example 12e (0.18 g, 0.46 mmol), triethylamine (0.62 mL, 0.45 g, 4.4 mmol) and 4-(dimethylamino)pyridine (56 mg, 0.46 mmol) in THF (6 mL) at room temperature. After 5 min, 1-amino-2-methyl-2-thiopropane (85.6 mg, 0.55 mmol) was added. The resulting mixture was stirred at room temperature for 16 hours. The reaction mixture was diluted with EtOAc (50 mL), washed with water, brine, dried over $Na_2SO_4$, and filtered. Evaporation of the solvent gave a residue that was chromatographed on silica gel eluting with 2% $MeOH:CH_2Cl_2$ to give the title compound (189 mg, 83%) as a white foam. mp 45–47° C. $^1H$-NMR (300 MHz, DMSO-$d_6$) δ 7.44 (d, J=8.4 Hz, 2H), 7.44 (d, J=8.4 Hz, 2H), 7.08–7.11 (mult, 4H), 4.95–5.05 (br, s 2H), 3.60 (s, 2H), 3.21 (s, 3H), 3.14 (s, 3H), 2.86 (s, 1H), 1.95 (s, 3H), 1.33 (s, 6H); $^{13}$C NMR (75 MHz, $CDCl_3$) δ 170.6, 170.2, 160.9, 143.9, 141.0, 139.8, 132.7, 131.3, 131.2, 130.6, 127.6, 116.1, 115.8, 65.5, 60.6, 46.5, 44.6, 39.4, 31.7, 21.0; mass spectrum (API-TIS) m/z 494 (MH+).

13b. (2Z)-3-(4-Fluorophenyl)-3-(N-methyl-N-(2-methyl-2-(nitrosothio)propyl) carbamoyl)-2-(4-(methylsulfonyl)phenyl)prop-2-enyl acetate To a solution of t-BuONO (141 μL of 90% solution, 111 mg, 1.08 mmol) in $CH_2Cl_2$ (1.4 mL) was added dropwise a solution of the product of Example 13a (163 mg, 0.33 mmol) in $CH_2Cl_2$ (4.3 mL) at 0° C. The resulting green solution was stirred at 0° C. for 15 min and at room temperature and then for 15 min in the dark. The residue, after evaporation of the solvent, was chromatographed on silica gel eluting with 1:1 to 2:1 $EtOAc:CH_2Cl_2$ to give the title compound 60 mg (35%) as a green foam. mp 37–38° C. $^1H$-NMR (300 MHz, $CDCl_3$) δ 7.80 (d, J=8.3 Hz, 2H), 7.35 (d, J=8.3 Hz, 2H), 7.04–7.08 (mult, 2H), 6.85–6.90 (mult, 2H), 4.96 (s, 2H), 4.25 (s, 2H), 3.04 (s, 3H), 2.95 (s, 3H), 2.04 (s, 3H), 1.92 (s, 6H); $^{13}$C NMR (75 MHz, $CDCl_3$) δ 170.6, 170.5, 164.2, 160.9, 143.7, 140.6, 139.8, 133.0, 131.2, 131.1, 130.5, 130.2, 127.5, 116.1, 115.8, 65.4, 58.2, 57.8, 44.5, 39.3, 27.9, 20.9; mass spectrum (API-TIS) m/z 493 (M–NO), 523 (MH+), 540 ($MNH_4^+$).

Example 14

2-(1-Methyl-4-(nitrosothio)-4-piperidyl)ethyl (2Z)-3-(4-acetyloxy-2-(4-fluorophenyl)-3-(4-(methylsulfonyl)phenyl)but-2-enoate 14a. 2-(1-Methyl-4-(nitrosothio)-4-piperidyl)ethyl (2Z)-3-(4-acetyloxy-2-(4-fluorophenyl)-3-(4-(methylsulfonyl)phenyl)but-2-enoate DCC (0.11 g, 0.53 mmol) in $CH_2Cl_2$ (5 mL) was added dropwise to a stirred solution of the product of Example 12e (0.21 g, 0.53 mmol), 2-(1-methyl-4-(nitrosothio)-4-piperidyl)ethan-1ol (prepared as described in Patent Application WO/025776, (the disclosure of which is incorporated by reference herein in its entirety) Example 13d, 0.132 g, 0.64 mmol) and 4-(dimethylamino)pyridine (33 mg, 0.27 mmol) in $CH_2Cl_2$ (5 mL) at room temperature. The resulting suspension was stirred at room temperature for 16 hours then the precipitate was filtered and washed with $CH_2Cl_2$ (10 mL). The combined organic phase was dried over $Na_2SO_4$ and filtered. The residue after evaporation of the solvent was chromatographed on silica gel eluting with 2% MeOH: $CH_2Cl_2$ to give the title compound 13 mg (4%) as a green oil. $^1H$-NMR (300 MHz, $CDCl_3$) δ 7.76 (d, J=8.4 Hz, 2H), 7.28 (d, J=9.1 Hz, 2H), 6.94–6.98 (mult, 2H), 6.81–6.86 (mult, 2H), 5.15 (s, 2H), 4.42 (t, J=6.7 Hz, 2H), 3.00 (s, 3H), 2.68 (t, J=6.8 Hz, 2H), 2.30 (s, 3H), 2.15–2.43 (mult, 8H), 1.93 (s, 3H); mass spectrum (API-TIS) m/z 549 (M–NO), 579 (MH+).

Example 15

(3Z)-4-(4-Chlorophenyl)-3-(ethoxycarbonyl)-4-(4-(methylsulfonyl) phenyl)but-3-enoic acid 15a. (3Z)-4-(4-Chlorophenyl)-3-(ethoxycarbonyl)-4-(4-(methylsulfonyl)phenyl)but-3-enoic acid This compound was synthesized as described in U.S. Pat. No. 5,807,873, (the disclosure of which is incorporated by reference herein in its entirety), Example 63. $^1H$-NMR (300 MHz, $CDCl_3$) δ 7.96 (d, J=8.2 Hz, 2H), 7.40 (d, J=8.3 Hz, 2H), 7.30 (d, J=8.4 Hz, 2H), 7.07 (d, J=8.4 Hz, 2H), 4.03 (q, J=7.1 Hz, 2H), 3.45 (s, 2H), 3.10 (s, 3H), 0.97 (t, J=7.1 Hz, 3H); mass spectrum (API-TIS) m/z 377 (M-$CO_2$), 423 (MH+), 440 ($MNH_4^+$), 445 (MNa+).

15b. 2-Bromo-1-(1,1,2,2-tetramethyl-1-silapropoxy)ethane t-Butyldimethylchlorosilane (21.7 g, 144 mmol) in dry THF (50 mL) was added dropwise to a solution of 1,2-bromoethanol (18 g, 144 mmol) and imidazole (9.81 g, 144 mmol) in dry THF (50 mL) at room temperature. The resulting white suspension was stirred at room temperature for 16 hours. The reaction mixture was diluted with EtOAc (200 mL), washed with water, brine, dried over $Na_2SO_4$, filtered and concentrated in vacuo at room temperature to give the title compound 33.2 g (96%) as a colorless liquid. $^1H$-NMR (300 MHz, $CDCl_3$) δ 3.89 (t, J=6.5 Hz, 2H), 3.39 (t, J=6.6 Hz, 2H), 0.90 (s, 9H), 0.10 (s, 6H); $^{13}$C NMR (75 MHz, $CDCl_3$) δ 63.7, 60.5,33.4,26.0, 21.2,14.3, –5.1.

15c. 4-(1-Methyl-1-((2,4,6-trimethoxyphenyl)methylthio)ethyl)-3-(2-(1,1,2,2-tetramethyl-1-silapropoxy)ethyl)-1,3-oxazolidin-2-one NaH (1.6 g, 66.7 mmol) was added portionwise to a solution of the product of Example 12h (15.3 g, 44.9 mmol) in dry DMF (50 mL) under nitrogen at 0° C. The resulting suspension was stirred at 0° C. for 20 min to give a brown red solution. The product of Example 15b (12.9 g, 53.8 mmol) in DMF (10 mL) was added dropwise and stirred at room temperature for 16 hours. The solvent was evaporated. The residue was partitioned with 1:1 EtOAc:water and the organic layer was separated. The aqueous layer was extracted with EtOAc and the combined organic layers were washed with water, dried over $Na_2SO_4$, and filtered. The residue after evaporation of the solvent was chromatographed on silica gel eluting with 1:1 EtOAc:Hexane to give the title compound (18 g, 80%) as a white foam. $^1H$-NMR (300 MHz, $CDCl_3$) δ 6.12 (s, 2H), 4.38–4.47 (mult, 1H), 4.09–4.21 (mult, 3H), 3.83 (s, 9H), 3.79 (s, 2H), 3.71–3.79 (mult, 2H), 3.42–3.53 (m, 1H), 1.50 (s, 3H), 1.29 (s, 3H), 0.95 (s, 9H), 0.08 (s, 6H); $^{13}$C NMR (75 MHz, $CDCl_3$) δ 160.8, 159.7, 158.9, 106.5, 90.9, 65.9, 62.3, 60.5, 56.0, 55.5, 48.6, 47.5, 26.4, 26.0, 22.6, 21.2, 20.3, 18.3, 14.4, -5.3; mass spectrum (API-TIS) m/z 500 (MH+).

15d. 3-(2-Hydroxyethyl)-4-(1-methyl-1-sulfanylethyl)-1,3-oxazolidin-2-one

The product of Example 15c (14.9 g, 29.8 mmol) was treated with water (11.8 mL), phenol (11.8 g), anisole (11.8 mL) and finally trifluoroacetic acid (147 mL). The resultant solution was stirred at room temperature for 1 hour and then the solvent was evaporated to give a yellow oil which was chromatographed on silica gel eluting with 1:1 EtOAc: Hexane to 5% $MeOH:CH_2Cl_2$ to give the title compound 4.2 g (69%) as a pale yellow oil. 1H-NMR (300 MHz, CDCl$_3$) δ 4.33–4.43 (mult, 2H), 3.72–3.92 (mult, 4H), 3.50–3.59 (mult, 1H), 2.55–2.80 (br s, 1H), 1.78 (s, 1H), 1.41 (s, 6H); $^{13}$C NMR (75 MHz, CDCl$_3$) δ 160.6, 66.2, 66.0, 60.4, 48.3, 47.6, 29.0, 27.8; mass spectrum (API-TIS) m/z 206 (MH$^+$), 223 (MNH$_4^+$). Anal. Calcd for C$_8$H$_{15}$NO$_3$S: C, 46.81; H, 7.37; N, 6.82. Found: C, 46.81; H, 7.11; N, 6.61.

15e. 3-(2-Hydroxyethyl)-4-(1-methyl-1-(nitrosothio) ethyl)-1,3-oxazolidin-2-one To a solution of t-butyl nitrite (4.45 mL of 90% solution, 3.5 g, 34.1 mmol) in CH$_2$Cl$_2$ (28 mL) was added dropwise a solution of the product of Example 15d (3.88 g, 18.9 mmol) in CH$_2$Cl$_2$ (58 mL) at 0° C. The resulting green solution was stirred at 0° C. for 1 hour and then at room temperature for 20 min in the dark. The residue after evaporation of the solvent was chromatographed on silica gel eluting with 1:1 EtOAc:CH$_2$Cl$_2$ to 5% MeOH:CH$_2$Cl$_2$ to give the title compound 3.7 g (84%) as a green oil. $^1$H-NMR (300 MHz, CDCl$_3$) δ 4.70–4.74 (mult, 1H), 4.41–4.52 (mult, 2H), 3.77–3.89 (mult, 3H), 3.44–3.50 (mult, 1H), 1.99 (s, 3H), 1.96 (s, 3H); $^{13}$C NMR (75 MHz, CDCl$_3$) δ 160.4, 65.8, 63.9, 60.0, 59.3, 48.1, 25.7, 24.8; mass spectrum (API-TIS) m/z 205 (M-NO), 235 (MH$^+$), 252 (MNH$_4^+$). Anal. Calcd for C$_8$H$_{14}$N$_2$O$_4$S: C, 41.02; H, 6.02; N, 11.96. Found: C, 41.30; H, 5.87; N, 11.68.

15f. (3Z)-4-(4-Chlorophenyl)-3-(ethoxycarbonyl)-4-(4-(methylsulfonyl)phenyl)but-3-enoic acid DCC (32 mg, 0.155 mmol) in CH$_2$Cl$_2$ (0.5 mL) was added dropwise to a stirred solution of the product of Example 15a (66 mg, 0.155 mmol), the product of Example 15e (36 mg, 0.154 mmol) and 4-(dimethylamino)pyridine (19 mg, 0.155 mmol) in CH$_2$Cl$_2$ (2 mL) at 0° C. The resulting suspension was stirred at 0° C. for 15 min and then at room temperature for 1.5 hours. The precipitate was filtered and washed with CH$_2$Cl$_2$ (5 mL). The combined organic phases were dried over Na$_2$SO$_4$ and filtered. The residue after evaporation of the solvent was chromatographed on silica gel eluting with 1:3 EtOAc:CH$_2$Cl$_2$ to give the title compound 69 mg (70%) as a green solid. mp 40–42° C. $^1$H-NMR (300 MHz, CDCl$_3$) δ 7.96 (d, J=6.7 Hz, 2H), 7.39 (d, J=6.6 Hz, 2H), 7.28–7.31 (mult, 2H), 7.04–7.07 (mult, 2H), 4.69–4.73 (m, 1H), 4.01–4.47 (m, 2H+2H+1H), 3.98 (q, J=7.1 Hz, 2H), 3.42–3.50 (mult, 1H), 3.37 (s, 2H), 3.09 (s, 3H), 1.96 (s, 3H), 1.93 (s, 3H), 0.93 (t, J=7.1 Hz, 3H); $^{13}$C NMR (75 MHz, CDCl$_3$) δ 170.7, 168.3, 159.1, 149.3. 145.6. 149.7. 139.4, 134.6, 130.0, 128.6, 128.0, 126.9, 65.4, 62.6, 61.3, 61.3, 59.1, 44.5, 44.3, 37.9, 25.2, 25.1, 13.6; mass spectrum (API-TIS) m/z 609 (M−NO), 639 (MH$^+$), 659 (MNH$_4^+$). Anal. Calcd for C$_{28}$H$_{31}$ClN$_2$O$_9$S$_2$: C, 52.62; H, 4.89; N, 4.38; Cl, 5.55; S, 10.03. Found: C, 52.40; H, 4.98; N, 4.17; Cl, 5.68, S, 9.80.

Example 16

3-Methyl-N-((4-(5-methyl-3-phenylisoxazol-4-yl)phenyl)sulfonyl)-3-(nitrosothio)butanamide

16a. 3-Methyl-N-((4-(5-methyl-3-phenylisoxazol-4-yl)phenyl)sulfonyl)-3-((2,4,6-trimethoxyphenyl)methylthiobutanamide 3-Methyl-3-((2,4,6-trimethoxyphenyl)methylthio)butanoic acid (prepared as described in patent application WO 97/34871, (the disclosure of which is incorporated by reference herein in its entirety), Example 1a, 1.05 g, 3.37 mmol) was added to a stirred solution of 4-(5-methyl-3-phenylisoxazol-4-yl)benzene sulfonamide (prepared as described by Talley et. al., *J. Med. Chem*. 43, 775 (2000); (the disclosure of which is incorporated by reference herein in its entirety), 0.85 g, 2.70 mmol), 4-(dimethylamino) pyridine (0.1 g) in THF (30 mL). The resulting solution was stirred at room temperature for 15 min and then solid DCC (0.84 g, 4.04 mmol) was added. The reaction mixture was stirred at room temperature for 3 hours, the solid was then removed by filtration. The filtrate was concentrated and the residue was chromatographed on silica gel eluting with 1:1 EtOAc:Hexane to give the title compound (0.92 g, 56%) as a white solid. mp 138–140° C. $^1$H-NMR (300 MHz, CDCl$_3$) δ 9.98 (s, 1H), 7.93 (d, J=8.4 Hz, 2H), 7.25–7.42 (mult, 7H), 6.20 (s, 2H), 3.92 (s, 6H), 3.38 (s, 3H), 3.79 (s, 2H), 2.54 (s, 2H), 2.45 (s, 3H), 1.20 (s, 6H); $^{13}$C-NMR (75 MHz, CDCl$_3$) δ 168.8, 167.3, 161.0, 158.5, 138.0, 136.1, 129.8, 129.7, 128.9, 128.7, 128.4, 114.5, 105.2, 91.1, 56.1, 55.4, 47.3, 43.8, 29.0, 21.1, 11.7; mass spectrum (API-TIS) m/z 611 (MH$^+$).

16b. 3-Methyl-N-((4-(5-methyl-3-phenylisoxazol-4-yl)phenyl)sulfonyl)-3-sulfanylbutanamide The product of Example 16a (0.6 g, 0.98 mmol) in CH$_2$Cl$_2$ (5 mL) was added to a stirred solution of cysteine (1.1 g, 9.07 mmol) in TFA (5 mL) and the resulting pale yellow solution was stirred at room temperature for 1 hour. Crushed ice (~3 g) was added and the mixture neutralized with concentrated NH$_4$OH (8 mL). The aqueous mixture was extracted with EtOAc (3×25 mL). The combined organic layers were dried over Na$_2$SO$_4$ and concentrated to give the title compound (0.4 g, 95%) as a viscous oil. This material was used in the next reaction without further purification. mp 138–140° C. $^1$H-NMR (300 MHz, CDCl$_3$) δ 8.05 (d, J=8.3 Hz, 2H), 7.30–7.40 (mult, 7H), 2.57 (s, 2H), 2.49(s, 3H), 2.09 (s, 1H), 1.37 (s, 6H); $^{13}$C-NMR (75 MHz, CDCl$_3$) δ 168.5, 167.5, 161.1,137.6, 136.3, 130.0, 129.7, 128.8,128.7, 128.4, 128.1, 114.4, 52.0, 42.0, 32.4, 11.7; mass spectrum (API-TIS), m/z 431 (MH$^+$).

16c. 3-Methyl-N-((4-(5-methyl-3-phenylisoxazol-4-yl)phenyl)sulfonyl)-3-(nitrosothio)butanamide A few drops of HCl in ether was added to a stirred solution of product of Example 16b (0.4 g, 0.93 mmol) in CH$_2$Cl$_2$ (5 mL) and MeOH (5 mL). t -BuONO (90%, 120 mL, 0.93 mmol) was then added. The resulting olive green solution was stirred at room temperature for 15 min under nitrogen. Cold water (25 mL) was added and the product was extracted into EtOAc (2×25 mL). The organic layer was dried over Na$_2$SO$_4$ and concentrated. Flash chromatography of the residue on silica gel eluting with 1:1 EtOAc/Hexane gave the title compound (0.32 g, 75%) as a green foam. $^1$H-NMR (300 MHz, CDCl$_3$) δ 9.38 (s, 1H), 7.96 (d, J=8.4 Hz, 2H), 7.28–7.43 (mult, 7H), 3.22 (s, 2H), 2.52 (s, 3H), 1.98 (s, 6H); $^{13}$C-NMR (75 MHz, CDCl$_3$) δ 167.8, 167.6, 161.1, 137.4, 136.2, 130.0, 129.8, 128.7,128.5, 128.0, 114.4, 53.6, 48.3, 27.8, 11.6; mass spectrum (API-TIS), m/z 460 (MH$^+$).

Example 17

2-Methyl-2-(nitrosothio)propyl-5-(4-chlorophenyl)-1-(4-sulfamoylphenyl)pyrazole-3-carboxylate

17a. Methyl 5-(4-chlorophenyl)-1-(4-sulfamoylphenyl)pyrazole-3-carboxylate

This compound was prepared as described in Penning et. al. *J. Med. Chem*. 40, 1347–1365 (1997), (the disclosure of which is incorporated by reference herein in its entirety), Compound 3a. mp 186° C. $^1$H-NMR (300 MHz, DMSO-d$_6$) δ 7.89 (d, J=8.6 Hz, 2H), 7.6–7.4 (m, 6H), 7.32 (d, J=8.6 Hz, 2H), 7.21 (s, 1H), 3.87 (s, 3H); mass spectrum (API-TIS) m/z 392 (MH$^+$).

17b. 5-(4-Chlorophenyl)-1-(4-sulfamoylphenyl) pyrazole-3-carboxylic acid

A stirred mixture of the product of Example 17a (9.75 g, 24.9 mmol), aqueous NaOH (1.5 N, 60 mL), and THF (200 mL) was heated to reflux for 5 hours. The reaction mixture was concentrated on a rotary evaporator. The residue was partitioned between EtOAc (200 mL) and 2N aqueous HCl (100 mL). The organic layer was separated and washed with water, dried over Na$_2$SO$_4$, filtered, and concentrated to give a solid material. Crystallization from EtOH/THF (1:1) gave the title compound (8.8 g, 90%) as an off-white solid. mp 203° C. $^1$H NMR (300 MHz, DMSO-d$_6$) δ 8.02 (d, J=8.4 Hz, 2H), 7.7–7.6 (m, 4H), 7.45 (d, J=8.4 Hz, 2H), 7.28 (s, 1H); mass spectrum (API-TIS) m/z 378 (MH$^+$).

17c. 2-methyl-2-sulfanylpropan-1-ol

To 2-methylpropanal (3.53 g, 49 mmol) in carbon tetrachloride (30 ml) was added sulfur monochloride (2 ml, 25 mmol) and the reaction mixture was stirred at 55° C. for 2 hours. After cooling to room temperature, the volatiles were evaporated in vacuo to give 2-((1,1-dimethyl-2-oxoethyl) disulfanyl)-2-methylpropanal. The disulfide (17.5 g, 85.7 mmol) was dissolved in THF (100 ml) and LiAlH$_4$ (86 ml, 1M/THF) was added slowly. After stirring at room temperature for 1 hour, the mixture was poured onto ice, treated with 3N HCl (150 ml) and then extracted with EtOAc. The organic extracts were dried over sodium sulfate and the volatiles were evaporated to yield 12.8 g (71%) of the title compound as a colorless oil. $^1$H NMR (300 MHz, CDCl$_3$) δ 3.44 (s, 2H), 2.25 (brs, 1H), 1.63 (s, 1H), 1.36 (s, 6H); $^{13}$C NMR (CDCl$_3$) 73.3, 46.3, 28.3.

17d. 2-methyl-2-(nitrosothio)propan-1-ol

To a solution of the product Example 17c (4.4 g, 41.5 mmol) in CH$_2$Cl$_2$ (50 ml) was added t-BuONO (5.5 ml, 41.5 mmol). The reaction mixture was stirred at room temperature for 10 minutes and the volatiles were evaporated in vacuo at 40° C. to give 4.6 g (82%) of the title compound as a dark green oil. $^1$H NMR (300 MHz, CDCl$_3$) δ 4.17 (s, 2H), 1.95 (brs, 1H), 1.90 (s, 6H); $^{13}$C NMR (CDCl$_3$) 70.5, 57.7, 25.1.

17e. 2-Methyl-2-(nitrosothio)propyl-5-(4-chlorophenyl)-1-(4-sulfamoylphenyl) pyrazole-3-carboxylate To a stirred solution of the product of Example 17b (3.78 g, 10.0 mmol), the product of Example 17d (1.35 g, 10.0 mmol), 1-(3-(dimethylamino)propyl)-3-ethylcarbodiimide hydrochloride (3.83 g, 20.0 mmol), and 4-(dimethylamino) pyridine (10 mg) in DMF (80 mL) was added triethylamine (2.79 mL, 20.0 mmol). After being stirred at room temperature for 4 hours, the mixture was diluted with EtOAc (200 mL), washed with 1N HCl, water, dried over Na$_2$SO$_4$, filtered, and concentrated. Chromatography of the residue on silica gel eluting with 1:4 EtOAc:Hexane gave the title compound (0.20 g, 4%) as a green solid. mp 153° C. (dec). $^1$H NMR (300 MHz, DMSO-d$_6$) δ 7.88 (d, J=8.6 Hz, 2H), 7.55–7.49 (m, 4H), 7.32 (d, J=8.6 Hz, 2H), 7.20 (s, 1H), 3.32 (s, 2H), 1.82 (s, 6H); mass spectrum (API-TIS) m/z 495 (MH+). Anal. Calcd. for C$_{20}$H$_{19}$ClN$_4$O$_5$S$_2$: C, 48.53; H, 3.87; N, 11.32; Cl, 7.16; S, 12.96. Found: C, 48.79; H, 4.12; N, 11.50; Cl, 6.81; S, 12.76.

Example 18

4-(4-Fluorophenyl)-5-(4-(methylsulfonyl)phenyl)-2-((4-((nitroxy)methyl)phenyl)methyl)-2-hydroxypyridazin-3-one

18a. 4-(4-Fluorophenyl)-5-(4-(methylsulfonyl)phenyl)-2-benzyl-2-hydropyridazin-3-one This compound was synthesized as described in patent application WO 99/10331, (the disclosure of which is incorporated by reference herein in its entirety), Example 10. m.p. 151–153° C. $^1$H -NMR (300 MHz, CDCl$_3$) δ 7.85 (d, J=8.4 Hz, 2H), 7.83 (m, 1H), 7.53 (m, 2H), 7.31 (m, 5H), 7.15 (m, 2H), 6.93 (m, 2H), 5.93 (s, 2H), 3.02 (s, 3H); $^{13}$C-NMR (75 MHz, CDCl$_3$) δ 164.3, 161.0, 159.5, 140.5, 138.7, 13706, 135.8, 132.5, 132.4, 129.9, 129.1, 128.6, 128.1, 127.7, 115.2, 115.2, 56.1; 44.2; mass spectrum (API-TIS) m/z 435 (MH$^+$).

18b. 4-(4-Fluorophenyl)-5-(4-(methylsulfonyl)phenyl)-2-hydropyridazin-3-one

To the product of Example 18a (74 mg, 0.17 mmol) in toluene (20 mL) was added AlBr$_3$ (140 mg, 0.52 mmol). The reaction mixture was heated at 90° C. for 15 minutes and then cooled to 0° C. The reaction mixture was then poured into ice cold water, acidified with 1 N HCl and extracted with ethyl acetate (2×50 mL). The combined extracts were washed with water (2×25 mL) and brine (1×25 mL), dried over Na$_2$SO$_4$ and filtered. Evaporation of the solvent gave a residue that was purified by column chromatography on silica gel eluting with 5% methanol in CH$_2$Cl$_2$ to give the title compound (45 mg, 76%). $^1$H NMR (300 MHz, CDCl$_3$) δ 7.8–7.9 (m, 3H), 7.35 (d, J=9 Hz, 2 H), 7.2 (m, 2 H), 7.0 (t, J=9 Hz, 2 H), 3.05 (s, 3 H); LRMS (APIMS) m/z 345 (M+H)$^+$.

18c. Methyl 4-((5-(4-fluorophenyl)-4-(4-(methylsulfonyl)phenyl)-6-oxohydro-pyridazinyl)methyl)benzoate The product of Example 18b (210 mg, 0.61 mmol) was dissolved in anhydrous DMF (3 mL) and then K$_2$CO$_3$ (336 mg, 2.44 mmol) was added. To this reaction mixture was added methyl 4-(bromomethyl)benzoate (140 mg, 0.61 mmol) and the mixture was stirred at room temperature overnight. The reaction mixture was diluted with water (25 mL) and extracted with ethyl acetate (2×50 mL). The combined extracts were washed with water (4×50 mL), brine (1×25 mL), and dried over sodium sulfate. Evaporation of the solvent gave a residue that was purified by column chromatography on silica gel eluting with 1:1 EtOAc:Hexane to gave the title compound (210 mg, 70%) as a colorless foam. $^1$H-NMR (300 MHz, CDCl$_3$) δ 8.02 (d, J=7.8 Hz, 2H), 7.86 (d, J=8.5 Hz, 2H), 7.84 (s, 1H), 7.58 (d, J=7.8 Hz, 2H), 7.32 (t, J=7.9 Hz, 2H), 7.15 (t, J=6.8 Hz, 2H), 6.94 (t, J=8.2 Hz, 2H), 5.43 (s, 2H), 3.89 (s, 3H), 3.03 (s, 3H); $^{13}$C-NMR (75 MHz, CDCl$_3$) δ 166.7, 164.5, 159.5, 140.8, 140.7, 140.4, 138.7, 137.4, 137.3, 132.5, 132.4, 130.0, 129.9, 129.0, 128.3, 127.8, 127.4, 115.3, 55.8, 52.1, 44.3; mass spectrum (API-TIS)) m/z 493 (MH$^+$).

18d. 4-(4-Fluorophenyl)-2-(4-(hydroxymethyl)phenyl)-5-(4-(methylsulfonyl)phenyl)-2-hydroxypyridazin-3-one The product of Example 18c (190 mg, 0.386 mmol) was dissolved in anhydrous $CH_2Cl_2$ (10 mL). The solution was cooled to 0° C. and 1M DIBAL-H (1.05 mL) was added dropwise under nitrogen atmosphere. The reaction mixture was stirred at 0° C. for 30 minutes and then at room temperature for 15 minutes. It was then quenched with ice cold water, acidified with 1 N HCl, and extracted with $CH_2Cl_2$ (2×50 mL). The combined extracts were washed water (2×25 mL), brine (1×25 mL) and then dried over $Na_2SO_4$. Evaporation of the solvent gave a residue that was purified by column chromatography on silica gel eluting 5% methanol in $CH_2Cl_2$ to give the title compound (100 mg, 54%) as a colorless foam. mp 155–164° C. $^1$H-NMR ($CDCl_3$) δ 7.86 (d, J=8.2 Hz, 2H), 7.82 (s, 1H), 7.52 (d, J=7.8 Hz, 2H), 7.34 (d, J=7.9 Hz, 2H), 7.29 (d, J=8.1 Hz, 2H), 7.14 (t, J=7.6 Hz, 2H), 6.93 (t, J=8.5 Hz, 2H), 5.38 (s, 2H), 4.65 (s, 2H), 3.03 (s, 3H); $^{13}$C-NMR (300 MHz, $CDCl_3$) δ 164.4, 161.1, 159.5, 140.9, 140.7, 140.5, 138.8, 137.2, 135.1, 132.4, 129.9, 129.4, 127.7, 127.6, 115.6, 115.3, 64.8, 55.9, 44.3; mass spectrum (API-TIS) m/z 465 ($MH^+$).

18e. 4-(4-Fluorophenyl)-5-(4-(methylsulfonyl)phenyl)-2-((4-((nitroxy)-methyl)phenyl)methyl)-2-hydroxypyridazin-3-one The product of Example 18d (30 mg, 0.065 mmol) was dissolved in anhydrous ethyl acetate (0.5 mL). In a separate flask the nitrating mixture was prepared by adding successively acetic anhydride (472 μL, 5.20 mmol) and fuming nitric acid (137 μL, 3.25 mmol) at 0° C. From this mixture, 65 μL was added to the above solution cooled to 0° C. The reaction mixture was stirred at 0° C. for 5 minutes and quenched with water and then extracted with ethyl acetate. The organic layer was separated, washed with water, brine, and dried over $Na_2SO_4$. Evaporation of the solvent gave a residue that was purified by preparative thin layer chromatography (0.25 mm thick silica gel plate) using 6:4 EtOAc: Hexane to give the title compound (5.5 mg, 17%) as a white solid. mp 78–87° C. $^1$H-NMR (300 MHz, $CDCl_3$) δ 7.86 (d, J=8.2 Hz, 2H), 7.84 (s, 1H), 7.58 (d, J=8.0 Hz, 2H), 7.39 (d, J=8.0 Hz, 2H), 7.31 (d, J=8.2 Hz, 2H), 7.15 (t, J=6.4 Hz, 2H), 6.95 (t, J=8.6 Hz, 2H), 5.41 (s, 2H), 5.40 (s, 2H), 3.04 (s, 3H); mass spectrum (API-TIS) m/z 510 ($MH^+$).

Example 19

4-(Methylsulfonyl)-1-(1-(2-(nitrooxy)ethyl)-4-benzylpyrazol-5-yl)benzene

19a. 1-(4-Methylthiophenyl)-3-phenylpropan-1-one

To a stirred solution of 4-(methylthio)benzonitrile (25.0 g, 0.17 mol) in THF (100 mL) under $N_2$ atmosphere was added phenethylmagnesium chloride (1.0 M in THF, 210 mL, 0.21 mol). The solution was heated to reflux for 4 hours, cooled to 0° C., and quenched carefully with water (10 mL). The resulting slurry was treated with 6 N hydrochloric acid (200 mL) and stirred at room temperature overnight. The THF was evaporated from the mixture, and the residue was extracted with EtOAc (2×300 mL). The combined organic extracts were washed with 2M $Na_2CO_3$, dried over $Na_2SO_4$, filtered, and concentrated to give a solid material. Recrystallization from EtOAc-Hex (1:4) afforded the title compound (41.5 g, 96%) as greenish plates. mp 105° C. $^1$H NMR (300 MHz, $CDCl_3$) δ 7.85 (d, J=8.5 Hz, 2H), 7.32–7.19 (m, 7H), 3.24 (t, J=6.8 Hz, 2H), 3.06 (t, J=6.8 Hz, 2H), 2.50 (s, 3H); $^{13}$C NMR (75 MHz, $CDCl_3$) δ 198.2, 145.8, 141.3, 133.2 128.48, 128.42, 128.38, 126.1, 125.0, 40.2, 30.2, 14.7; mass spectrum (API-TIS) m/z 257 (M+H).

19b. Mixture of 2-(3-(4-methylthiophenyl)-4-benzylpyrazolyl)ethan-1-ol and 2-(5-(4-methylthiophenyl)-4-benzylpyrazolyl)ethan-1-ol To a stirred solution of the product of Example 19a (850 mg, 3.3 mmol) in THF (8 mL) at −78° C. under $N_2$ atmosphere was added lithium diisopropylamide (1.5 M in cyclohexane, 2.66 mL, 4.0 mmol) dropwise. After 30 min, a solution of $HCO_2Et$ (0.32 mL, 4.0 mmol) in THF (1 mL) was added, and the reaction was allowed to gradually warm to room temperature and stirred overnight. The mixture was poured into 1 N HCl (10 mL), and extracted with EtOAc (2×20 mL). The combined organic extracts were washed with saturated $NaHCO_3$ (10 mL), dried over $Na_2SO_4$, filtered, and concentrated to give an off-white solid (905 mg). A stirred solution of this solid and 2-hydoxyethylhydrazine (0.37 mL, 5.00 mmol) in EtOH (15 mL) was heated to reflux under $N_2$ for 3 hours, and then concentrated. The residue was dissolved in EtOAc (50 mL), washed with 1N HCl, dried over $Na_2SO_4$, filtered, and concentrated. The residue was chromatographed on silica gel eluting with EtOAc to give two regioisomeric pyrazoles as an inseparable mixture (0.81 g, 75% over two steps). Ratio of isomers 3:2 as judged by the proton NMR. $^1$H NMR (300 MHz, $CDCl_3$) δ 7.53–7.09 (m, ArH), 4.17 (t, J=4.5 Hz), 4.08 (t, J=4.5 Hz), 3.98 (t, J=5.0 Hz), 3.96 (s), 3.91 (t, 5.0 Hz), 3.71 (s), 2.51 (s), 2.49 (s); mass spectrum (API-TIS) m/z 325 (M+H).

19c and 19d. 1-(1-(2-Hydroxyethyl)-4-benzylpyrazol-5-yl)-4-(methylsulfonyl)benzene and 1-(1-(2-Hydroxyethyl)-4-benzylpyrazol-3-yl)-4-(methylsulfonyl)benzene The product of Example 19b (810 mg, 2.50 mmol) was dissolved in MeOH (15 mL), and treated with oxone (4.61 g, 7.50 mmol) and water (10 ml). The slurry was stirred at room temperature for 30 min. The reaction mixture was poured into water (20 mL), neutralized with aqueous $Na_2CO_3$, and extracted with EtOAc (50 mL×2). The combined organic extracts were dried over $Na_2SO_4$, filtered, and concentrated. The residue was chromatographed on silica gel eluting with EtOAc to give first compound Example 19c (450 mg, 50%) followed by Example 19d (260 mg, 29%). Physical data for Example 19c: $R_f$ 0.47 (EtOAc, silica gel). mp 96° C. $^1$H NMR (300 MHz, $CDCl_3$) δ 7.93 (d, J=8.6 Hz, 2H), 7.81 (d, J=8.6 Hz, 2H), 7.31–7.17 (m, 6H), 4.23 (t, J=4.5 Hz, 2H), 4.03 (t, J=4.5 Hz, 2H), 4.00 (s, 2H), 3.05 (s, 3H); $^{13}$C NMR (75 MHz, $CDCl_3$) δ 147.7, 139.9, 139.1, 138.8, 131.8, 128.6, 128.3, 128.0, 127.4, 126.3, 118.6, 61.6, 54.0, 44.4, 30.7; mass spectrum (API-TIS) m/z 357 (M+H). Anal. calcd for $C_{19}H_{20}N_2O_3S$: C, 64.02, H, 5.66; N, 7.86, S, 9.00. Found: C, 63.80; H, 5.76; N, 8.10; S, 8.98. Physical data for Example 19d: $R_f$ 0.38 (EtOAc, silica gel). mp 68° C. $^1$H NMR (300 MHz, $CDCl_3$) δ 7.99 (d, J=8.2 Hz, 2H), 7.51 (d, J=8.2 Hz, 2H), 7.41 (s, 1H), 7.25–7.14 (m, 3H), 7.06 (d, J=7.2 Hz, 2H), 4.07 (t, J=4.6 Hz, 2H), 3.93 (t, J=4.6 Hz, 2H), 3.72 (s, 2H), 3.09 (s, 3H); $^{13}$C NMR (75 Mhz, $CDCl_3$) δ 140.5, 140.3, 139.6, 139.5, 135.3, 130.9, 128.3, 128.1, 127.5, 126.0, 119.1, 61.3, 51.1, 44.2, 29.8; mass spectrum (API-TIS) m/z 357 (M+H). Anal. calcd for $C_{19}H_{20}N_2O_3S$: C, 64.02, H, 5.66; N, 7.86, S, 9.00. Found: C, 64.18; H, 5.87; N, 7.79; S, 8.94.

19e. 4-(Methylsulfonyl)-1-(1-(2-(nitrooxy)ethyl)-4-benzylpyrazol-5-yl)benzene Fuming $HNO_3$ (90%, 1 mL) was added to $Ac_2O$ (5 mL) at 0° C., and the resulting mixture was stirred for 10 minutes. The product of Example 19d (235 mg, 0.66 mmol) in EtOAc (6 mL) was added, and the solution was stirred at 0° C. for 5 min. The mixture was poured into ice-cooled saturated $NaHCO_3$ (10 mL), extracted with EtOAc (2×20 mL). The combined organic extracts were repeatedly washed with brine, dried over $Na_2SO_4$, filtered, and concentrated to afford the title product as oil (259 mg, 96%). $^1H$ NMR (300 MHz, $CDCl_3$) δ 8.02 (d, J=8.4 Hz, 2H), 7.47 (d, J=8.4 Hz, 2H), 7.24–7.18 (m, 4H), 7.06 (m, 2H), 4.77 (t, J=5.0 Hz, 2H), 4.31 (t, J=5.0 Hz, 2H), 3.72 (s, 2H), 3.10 (s, 3H); mass spectrum (API-TIS) m/z 402 (M+H).

Example 20

4-(1-Cyclohexyl-3-((nitrooxy)methyl)pyrazol-5-yl)-1-methylsulfonyl) benzene

20a. Methyl (2Z)-2-hydroxy-4-(4-methylthiophenyl)-4-oxobut-2-enoate

Dimethyloxalate (26 g, 180.7 mmol) was added to a stirred suspension of sodium methoxide (9.75 g, 180.7 mmol) in dry toluene (200 mL) at 0° C. The white suspension was stirred for 15 min at 0° C. A solution of 4'-(methylthio)acetophenone (15 g, 90.4 mmol) in dry toluene (150 mL) was then added dropwise over 15 min giving a yellow suspension which was stirred for 2 hours at room temperature. The thick yellow suspension was transferred to a 2 liter flask and stirred vigorously with 10% HCl (250 mL) and EtOAc (200 mL) to dissolve all the solids present. The organic layer was separated and the aqueous layer was extracted with EtOAc (100 mL). The combined organic extracts were washed with water (250 mL), dried over $Na_2SO_4$ and the solvent was evaporated under reduced pressure to give thick brown oil. The brown oil was dissolved in $CH_2Cl_2$ (25 mL) and hexane (125 mL) and left in a freezer at –20° C. for 16 hours to give the title compound (18 g, 79%) as orange color solid. mp 81° C. $^1H$-NMR (300 MHz, $CDCl_3$) δ 7.83 (d, J=8.6 Hz, 2H), 7.23 (d, J=8.6 Hz, 2H), 6.97 (s, 1H), 3.89 (s, 3H), 2.47 (s, 3H); $^{13}C$-NMR (75 MHz, $CDCl_3$); mass spectrum (API-TIS) m/z 253 (MH$^+$)

20b. Methyl-1-cyclohexyl-5-(4-methylthiophenyl)pyrazole-3-carboxylate.

A mixture of the product of Example 20a (1.98 g, 7.8 mmol) and cyclohexylhydrazine hydrochloride (1.54 g, 10.2 mmol) in methanol (40 mL) was heated at 70° C. for 3 hours and cooled to room temperature. The mixture was made basic with 10% $Na_2CO_3$ and extracted with EtOAc (3×25 mL). The organic extracts were dried over $Na_2SO_4$ and the solvent was evaporated under reduced pressure to give a thick oil. The oil was dissolved in $CH_2Cl_2$ (4 mL) and hexane (20 mL) and left in a freezer at –10° C. for 16 hours to give the title compound (2.2 g, 85%) as a white solid. mp 84° C. $^1H$-NMR (300 MHz, $CDCl_3$) δ 7.33 (d, J=8.3 Hz, 2H), 7.26 (d, J=8.3 Hz, 2H), 6.76 (s, 1H), 4.08–4.13 (mult, 1H), 3.93 (s, 3H), 2.54 (s, 3H), 2.07–2.20 (mult, 2H), 1.80–1.95 (mult, 4H), 1.62–1.72 (mult, 1H), 1.20–1.30 (mult, 3H); $^{13}C$-NMR (75 MHz, $CDCl_3$) δ 163.1, 143.6, 142.3, 140.1, 129.4, 126.4, 126.2, 108.8, 58.7, 51.9, 33.1, 25.5, 24.8, 15.3; mass spectrum (API-TIS), m/z 331 (MH$^+$). Anal. calcd for $C_{18}H_{22}N_2O_2S$: C, 65.43; H, 6.71; N, 8.48; S, 9.70 Found: C, 65.28; H, 6.66; N, 8.47; S, 9.61.

20c. 1-Cyclohexyl-5-(4-methylthiophenyl)pyrazole-3-yl)methan-1-ol.

A solution of lithium aluminum hydride (2 mL at 1 M, 2 mmol) was added to a stirred solution of the product of Example 20b (0.7 g, 2.1 mmol) in THF (15 mL) at 0° C. The resulting clear solution was stirred at room temperature for 1 hour. Solid $Na_2SO_4.10H_2O$ (2 g) was added in small portions with stirring until a thick precipitate formed. Methanol in $CH_2Cl_2$ (10%, 50 mL) was added and the mixture was filtered. The solid was washed with additional methanol in $CH_2Cl_2$ (10%, 50 mL) and the combined filtrates were evaporated to give the title compound (0.61 g, 95%) as a white solid. mp 97° C. $^1H$-NMR (300 MHz, $CDCl_3$) δ 7.31 (d, J=8.3 Hz, 2H), 7.24 (d, J=8.3 Hz, 2H), 6.20 (s, 1H), 4.71 (d, J=4.8 Hz, 2H), 4.00–4.15 (mult, 1H), 2.53 (s, 3H), 1.65–2.10 (mult, 7H), 1.15–1.30 (mult, 3H); $^{13}C$-NMR (75 MHz, $CDCl_3$) δ 151.0, 143.2, 139.3, 129.3, 127.5, 126.3, 104.1, 59.0, 57.7, 33.2, 25.6, 25.1, 15.4; mass spectrum (API-TIS) m/z 303 (MH$^+$).

20d. 4-(1-Cyclohexyl-3-(hydroxymethyl)pyrazol-5-yl)-1-(methylsulfonyl)benzene The product of Example 20c (0.6 g, 2.0 mmol) was dissolved in a mixture of MeOH (20 mL) and water (8 mL) and cooled to 0° C. Solid oxone (3 g) was added and the resulting suspension was stirred at 0° C. for 1 hr. Water (25 mL) and 15% $NH_4OH$ (25 mL) were added. The mixture was extracted with EtOAC (3×25 mL) and the organic extracts were dried over $Na_2SO_4$. The solvent was evaporated under reduced pressure to give white solid which was recrystallized from $CH_2Cl_2$ (5 mL) and hexane (20 mL) to give the title compound (0.62 g, 94%) as a white solid. mp 148° C. $^1H$-NMR (300 MHz, $CDCl_3$) δ 8.03 (d, J=8.3 Hz, 2H), 7.56 (d, J=8.3 Hz, 2H), 6.31 (s, 1H), 4.73 (s, 2H), 3.90–4.10 (mult, 1H), 3.13 (s, 3H), 2.45 (s, 1H, OH), 1.66–2.05 (mult, 7H), 1.10–1.25 (mult, 3H); $^{13}C$-NMR (75 MHz, $CDCl_3$) δ 151.4, 141.7, 140.4, 136.5, 129.7, 127.9, 105.0, 59.0, 58.2, 44.4, 33.3, 25.6, 25.0; mass spectrum (API-TIS), m/z 335 (MH$^+$).

20e. 4-(1-Cyclohexyl-3-(nitrooxy)methyl)pyrazol-5-yl)-1-(methylsulfonyl)benzene Fuming $HNO_3$ (0.76 mL, 18 mmol) was added to $Ac_2O$ (2.7 mL, 28.8 mmol) at 0° C. via syringe and stirred for 5 min at 0° C. The mixture was then transferred with a pasteur pipette to a stirred suspension of the product of Example 20d (1.2 g, 3.6 mmol) in EtOAc (40 mL) at room temperature and the mixture was stirred for 45 minutes at room temperature. Cold saturated $NaHCO_3$ (40 mL) was added and shaken well in a separatory funnel. The organic layer was separated and dried over $Na_2SO_4$. The solvent was evaporated under reduced pressure to afford a viscous oil which was dissolved in $CH_2Cl_2$ (5 mL) and hexane (25 mL). The resulting clear solution was left in a freezer at –10° C. for 4 hours to give title compound (1.05 g, 77%) as a yellow solid.

mp 104° C. $^1$H-NMR (300 MHz, CDCl$_3$) δ 8.05 (d, J=8.4 Hz, 2H), 7.55 (d, J=8.4 Hz, 2H), 6.39 (s, 1H) 5.50 (s, 2H), 3.95–4.10 (mult, 1H), 3.13 (s, 3H), 1.60–2.10 (mult, 7H), 1.15–1.30 (mult, 3H); $^{13}$C-NMR (75 MHz, CDCl$_3$) δ 143.1, 142.1, 140.7, 136.0, 129.8, 127.9, 107.3, 68.6, 58.6, 44.4, 33.3, 25.5, 25.0; mass spectrum (API-TIS) m/z 380 (MH$^+$). Anal. calcd for C$_{17}$H$_2$N$_3$O$_5$S: C, 53.81; H, 5.58; N, 11.07; S, 8.45 Found C, 53.55; H, 5.55; N, 10.83; S, 8.36.

Example 21

Assay for Ovine COX-1 and COX-2 Activity

The ovine COX-1 and COX-2 activities and the measurement of the prostaglandin products synthesized were performed using the COX Inhibitor Screening Assay (Cayman Chemical, Ann Arbor, Mich., which also contained the Prostaglandin Screening EIA Kit, used for prostaglandin quantification). The test compounds were dissolved at 50 times the highest final reaction concentration in DMSO or any other suitable solvent as stock solutions. These stock solutions were then diluted in the same solvent. Eight glass test tubes (13×100 mm) were placed in a 37° C. water bath. To each test tube was added 950 μL of reaction buffer (0.1 M Tris-HCl, pH 8.0, containing 5 mM EDTA, and 2 mM phenol), 10 μL of 100 M heme solution, and 10 μL (5 units) of either ovine COX-1 or COX-2 and the resulting mixture was incubated with the enzyme for 2 minutes. Twenty μL of the solvent was added to one tube (100% initial activity or solvent control) and 20 μL of each dilution of the test compound was added to one tube each. Each tube was vortexed immediately after the addition. The enzyme was incubated with the inhibitor for 3.5 minutes at 37° C. The enzymatic reaction was then initiated by the addition of 10 μL of freshly prepared 10 mM arachidonic acid (neutralized with KOH), vortexed and then incubated for 2 minutes at 37° C. The reaction was terminated by the addition of 50 μL of 1 M HCl, vortexed and placed at room temperature. One hundred microliters of a saturated stannous chloride solution (50 mg/mL of 0.1 M HCl) was added and the reaction mixture was allowed to stand at room temperature for at least 5 minutes.

The prostaglandins (PG) produced in the reactions were assayed, after a 2,000-fold dilution, using the Prostaglandin Screening EIA Kit (Cayman Chemical, Ann Arbor, Mich.). The assay-contains an antibody with broad specificity for all the prostaglandin families (PGF, PGE, PGD, and thromboxane B-type) synthesized in the COX-1/COX 2 reactions. The synthesized prostaglandin competes with a PG-tagged acetylcholine esterase tracer for binding to the PG antibody. Binding of synthesized PG lowers the calorimetric development of the Ellman's Reagent (computed as % B/B$_0$). The actual amount of synthesized PG was interpolated from a standard curve using known amounts of supplied prostaglandin E2 (PGE$_2$) (PGE$_2$ concentration vs. % B/B$_0$). The data generated were the mean±standard deviation of triplicate wells in the EIA for a single reaction at a given inhibitor concentration. A plot of % of control (i.e., the solvent control without inhibitor) vs. test compound inhibitor concentration for both isoenzymes was used to determine the IC$_{50}$'s for COX-1 and COX-2 for that test compound. The IC$_{50}$ for the compounds are given in Table 1.

TABLE 1

IC$_{50}$ VALUES FOR COX-1 and COX-2

| Test Compound | COX-1 IC$_{50}$ (μM) | COX-2 IC$_{50}$ (μM) |
|---|---|---|
| Indomethacin | 0.18 | 0.35 |
| Celecoxib | 34 | 0.34 |
| Example 1a | 100 | 3.3 |
| Example 1b | 190 | 10 |
| Example 2a | No inhibition up to 300 | 24 |
| Example 2b | No inhibition up to 300 | 1.2 |
| Example 3e | 62 | 0.006 |
| Example 3g | No inhibition up to 300 | 70 |
| Example 5a | No inhibition up to 300 | 12 |
| Example 5b | No inhibition up to 300 | 33 |

The NSAID, indomethacin, did not show selectivity for either COX-1 or COX-2. Celecoxib, a selective COX-2 inhibitor, used as a control, was selective for COX-2. The results show that the nitrosated compounds (i.e., Examples 1b, 2b and 5b) have similar COX-2 selectivity as their parent non-nitrosated compound (i.e., Example 1a, 2a and 5a respectively). Hence, nitrosation did not effect the COX-2 inhibition properties. The results show that the nitrosylated compound (i.e., Example 3g) was not as potent as the parent non-nitrosylated compound (i.e., Example 3e). The nitrosylation of the sulfonamide group on the parent COX-2 inhibitor probably effected the COX-2 inhibition properties of the nitrosylated compound.

Example 22

Assay for Human COX-1 and COX-2 activity

The human COX-1 and COX-2 activities and the measurement of the prostaglandin products synthesized were performed using the COX Inhibitor Screening Assay (Cayman Chemical, Ann Arbor, Mich., which also contained the Prostaglandin Screening EIA Kit, used for prostaglandin quantification). The test compounds were dissolved at 50 times the highest final reaction concentration in DMSO or any other suitable solvent as stock solutions. These stock solutions were then diluted in the same solvent. Eight glass test tubes (13×100 mm) were placed in a 25° C. water bath. To each test tube was added 950 μL of reaction buffer (0.1 M Tris-HCl, pH 8.0, containing 5 mM EDTA, and 2 mM phenol), 10 μL of 100 M heme solution, and 10 μL (5 units) of either human COX-1 or COX-2 and the resulting mixture incubated with the enzyme for 2 minutes. Twenty μL of the solvent was added to one tube (100% initial activity or solvent control) and 20 μL of each dilution of the test compound was added to one tube each. Each tube was vortexed immediately after the addition. The enzyme was incubated with the inhibitor for 20 minutes at 25° C. The enzymatic reaction was then initiated by the addition of 10 μL of freshly prepared 10 mM arachidonic acid (neutralized with KOH), vortexed and then incubated for 2 minutes (or, in some cases as indicated, 30 seconds) at 37° C. The reaction was terminated by the addition of 50 μL of 1 M HCl, vortexed and placed at room temperature. One hundred microliters of a saturated stannous chloride solution (50 mg/mL of 0.1 M HCl) was added and the reaction mixture was allowed to stand at room temperature for at least 5 min.

The prostaglandins (PG) produced in the reactions were assayed, after a 2,000-fold dilution, using the Prostaglandin Screening EIA Kit (Cayman Chemical, Ann Arbor, Mich.). The assay contains an antibody with broad specificity for all the prostaglandin families (PGF, PGE, PGD, and thromboxane B-type) synthesized in the COX-1/COX 2 reactions. The synthesized prostaglandin competes with a PG-tagged acetylcholine esterase tracer for binding to the PG antibody. Binding of synthesized PG lowers the colorimetric development of the Ellman's Reagent (computed as % $B/B_0$). The actual amount of synthesized PG was interpolated from a standard curve using known amounts of supplied prostaglandin E2 ($PGE_2$) ($PGE_2$ concentration vs. % $B/B_0$). The data generated were the mean±standard deviation of triplicate wells in the EIA for a single reaction at a given inhibitor concentration. A plot of % of control (i.e., the solvent control without inhibitor) vs. test compound inhibitor concentration for both isoenzymes was used to determine the $IC_{50}$'s for COX-1 and COX-2 for that test compound, when $IC_{50}$'s were calculated. The % inhibition for selected concentrations of inhibitors tested are given in Table 2.

TABLE 2

% INHIBITION OF HIUMAN COX-1 AND COX-2

| Test Compound | COX-1 Inhibition (% at 100 μM) | COX-2 Inhibition (% at 10 μM) |
| --- | --- | --- |
| Example 2a | 0[a] | 65 |
| Example 2b | 0[a] | 100 |
| Example 4a | 89[b] | 69[b] |
| Example 4b | 49[b] | 91[b] |
| Example 19d | 95 | 100 |
| Example 19e | 0 | 100 |
| Example 20d | 16 | 34 |
| Example 20e | 0 | 37 |

[a] = Ovine COX-1
[b] = 30 second incubation with arachidonic acid substrate

The results show that the nitrosated compounds (i.e., Examples 2b, 5b, 19e and 20e) have similar or slightly improved COX-2 selectivity compared to their parent non-nitrosated compound (i.e., Example 2a, 4a, 19d and 20d, respectively). Hence, nitrosation did not effect the COX-2 inhibition properties and might improve the COX-2 inhibition properties.

Example 23

Preparation of Rat Aortic Smooth Muscle Rings

Male Sprague-Dawley rats (Charles River Laboratories (Wilmington, Mass.) were euthanized by intraperiton injection of a high dose of sodium pentobarbitone (80–100 mg/kg). The thoracic aorta was rapidly excised and immediately placed in a Petri dish containing warm (37° C.) oxygenated (95% $O_2$ and 5% $CO_2$) Kreb's buffer (composition per millimolar: NaCl (119); KCl (4.69); $CaCl_2.H_2O$ (2.52); $MgSO_4.7H_2O$ (0.57); $NaHCO_3$ (25); $NaH_2PO_4.H_2O$ (1.01) and glucose (11.1). Under a stereoscopic dissecting microscope, the aorta was cleaned, freed from adhering fat and connective tissues. The tissue was cut into ring segments, each approximately 2–3 mm in length.

For experiments to measure relaxation of the tissue under various conditions, a stainless steel tissue holder and an U-shaped stainless steel wire were inserted into the lumen of the aortic ring. The tissue holder anchored the ring at the bottom of the organ bath whereas the end of the U-shaped steel wire was tied with fine silk thread so that it connected to the FT-202 transducer. The tissue holder and the steel wire along with the aortic ring were then suspended in a 5-mL double-jacketed temperature-controlled glass organ bath (Radnoti Glass Technology, Inc., Monrovia, Calif.) filled with fresh Kreb's buffer. A mixture of 95% $O_2$ and 5% $CO_2$ was bubbled through a porous sintered disc at the bottom of the bath. The rings were given an initial resting tension of 1.5 g and the preparation was allowed to equilibrate at the initial tension for about 90 minutes. During this equilibration period, the bath fluid was changed every 15 minutes and replaced with fresh prewarmed (37° C.) Kreb's buffer. The isometric tension of the aortic muscle at rest and its response to different stimuli were recorded on a Power Macintosh 6100 computer via a MacLab 8/S computer interface (CB Sciences, Inc, Milford, Mass.) after an initial amplification through a low-noise ETH-400 bioamplifier (CB Sciences, Inc, Milford, Mass.). Contractile responsiveness of the tissue strips was established with 10 μM phenylephrine and the strips were incubated with the drug for 20 minutes to establish a steady level of contraction. To test the relaxation effects, test compounds were added to the phenylephrine-precontracted strips in the tissue bath at cumulative concentrations of 0.1 μM to 0.1 mM. Concentration of test compounds was increased only after relaxation at the previous concentration had reached a plateau level.

Example 24

Relaxation of Aortic Smooth Muscle Ring by Example 1

The tissue was prepared according to Example 23. The percent contraction of phenylephrine-contracted aortic smooth muscle rings induced by isosorbide dinitrate (ISDN), Example 1a and Example 1b (nitrate) was measured. FIG. 1 shows that the parent non-nitrosated compound, Example 1a, did not relax the aortic ring. The nitrosated compound, Example 1b, induced the relaxation of the aortic ring. The observed relaxation was more potent than that obtained by the nitrate compound, isosorbide dinitrate.

Example 25

Relaxation of Aortic Smooth Muscle Ring by Example 2

Figure 2:
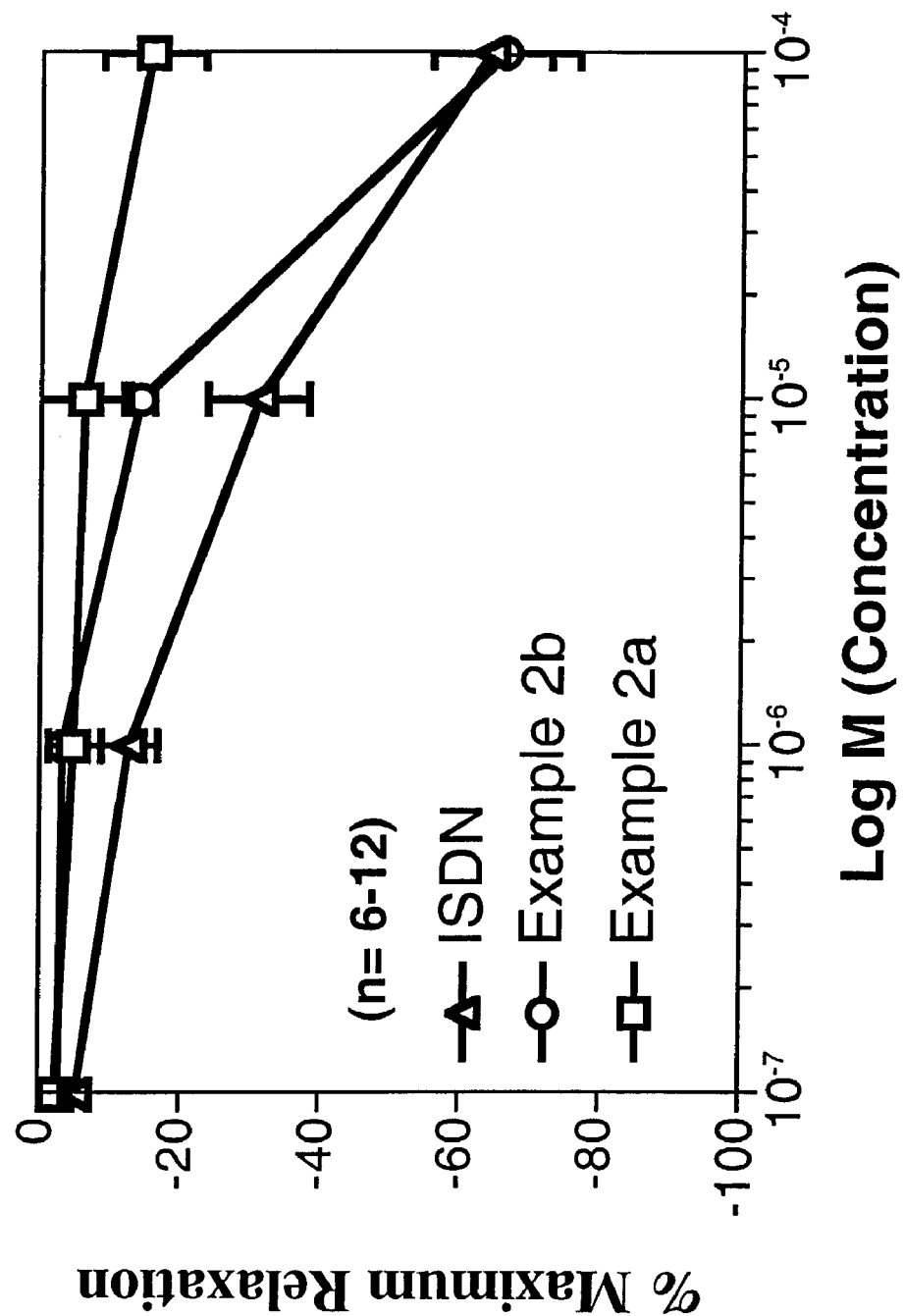
FIG. 2 shows the relaxation of rat aortic smooth muscle rings by (a) isosorbide dinitrate (ISDN, open triangles); (b) Example 2a (non-nitrosated compound, open squares); and (c) Example 2b (nitrosated compound, open circles). The non-nitrosated compound of Example 2a did not relax the tissue. At higher concentrations, the relaxation of the nitrosated compound of Example 2b was comparable to that obtained with ISDN. Total number of samples tested varied from a minimum of 6 to a maximum of 12. In the x axis, log M corresponds to ten fold increases of the test compound from 100 nM ($10^{-7}$) to 100 μM ($10^{-4}$). Results are expressed as the mean±standard error of the mean of the percentage of total relaxation induced by 10 μM phenylephrine.

The tissue was prepared according to Example 23. The percent contraction of phenylephrine-contracted aortic smooth muscle rings induced by isosorbide dinitrate (ISDN), Example 2a and Example 2b (nitrate) was measured. FIG. 2 shows that the parent non-nitrosated compound, Example 2a, did not relax the aortic ring. The nitrosated compound, Example 2b, induced the relaxation of the aortic ring. The observed relaxation was similar to that obtained by the nitrate compound, isosorbide dinitrate.

Example 26

Relaxation of Aortic Smooth Muscle Ring by Example 3

Figure 3:
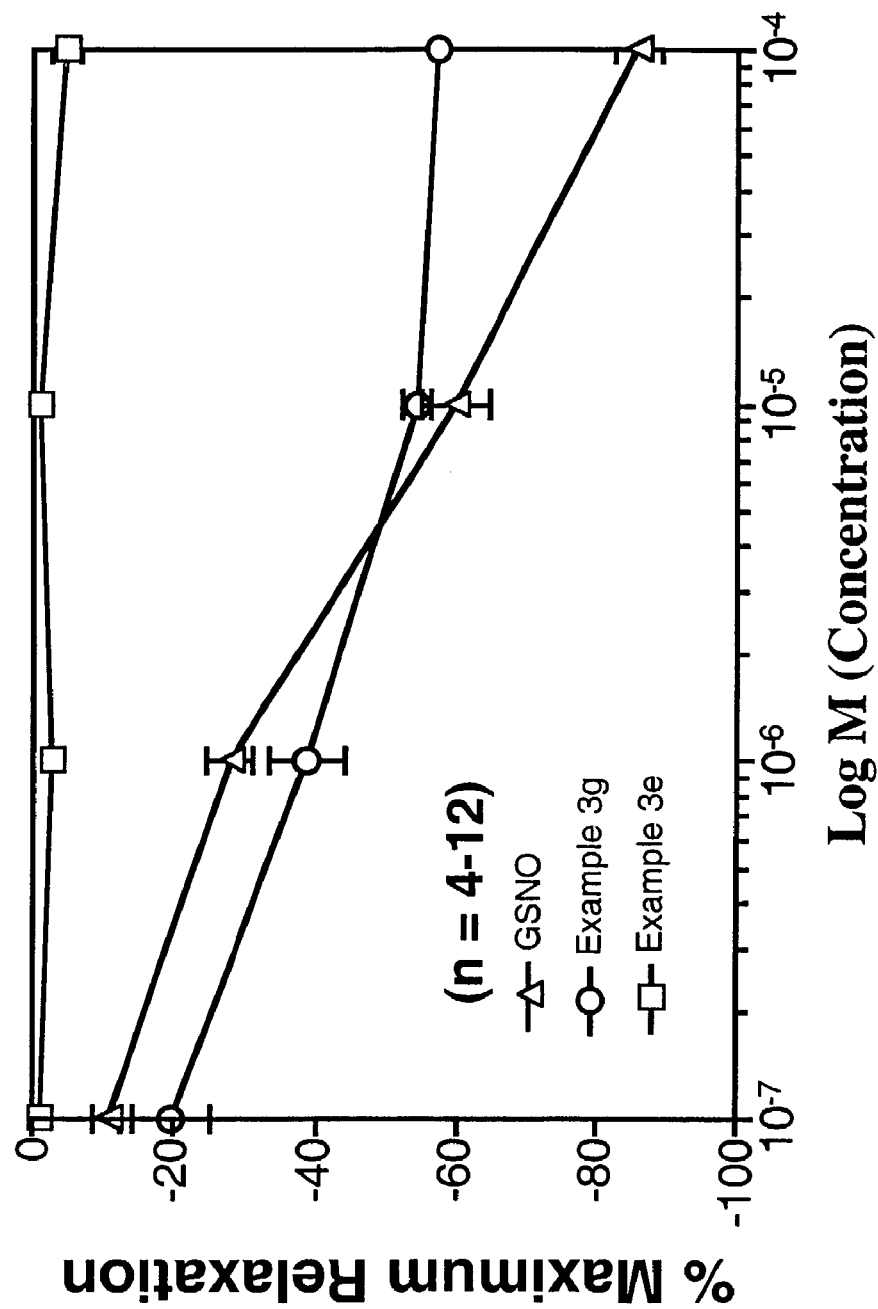
FIG. 3 shows the relaxation of rat aortic smooth muscle rings by (a) S-nitrosoglutathione (GSNO, open triangles); (b) Example 3e (non-nitrosylated compound, open squares); and (c) Example 3g (nitrosylated compound, open circles). The non-nitrosylated compound of Example 3e did not relax the tissue. At higher concentrations, the relaxation of the nitrosylated compound of Example 3g was comparable to that obtained with GSNO. Total number of samples tested varied from a minimum of 4 to a maximum of 12. In the x axis, log M corresponds to ten fold increases of the test compound from 100 nM ($10^{-7}$) to 100 μM ($10^{-4}$). Results are expressed as the mean±standard error of the mean of the percentage of total relaxation induced by 10 μM phenylephrine.

The tissue was prepared according to Example 23. The percent contraction of phenylephrine-contracted aortic smooth muscle rings induced by S-nitrosoglutathione (GSNO), Example 3e and Example 3h (nitrosothiol) was measured. FIG. 3 shows that the parent non-nitrosylated compound, Example 3e, did not relax the aortic ring. The nitrosylated compound, Example 3h, induced the relaxation of the aortic ring. The observed relaxation was similar to that obtained by the nitrosothiol compound, S-nitrosoglutathione.

Example 27

Relaxation of Aortic Smooth Muscle Ring by Example 20

Figure 4:
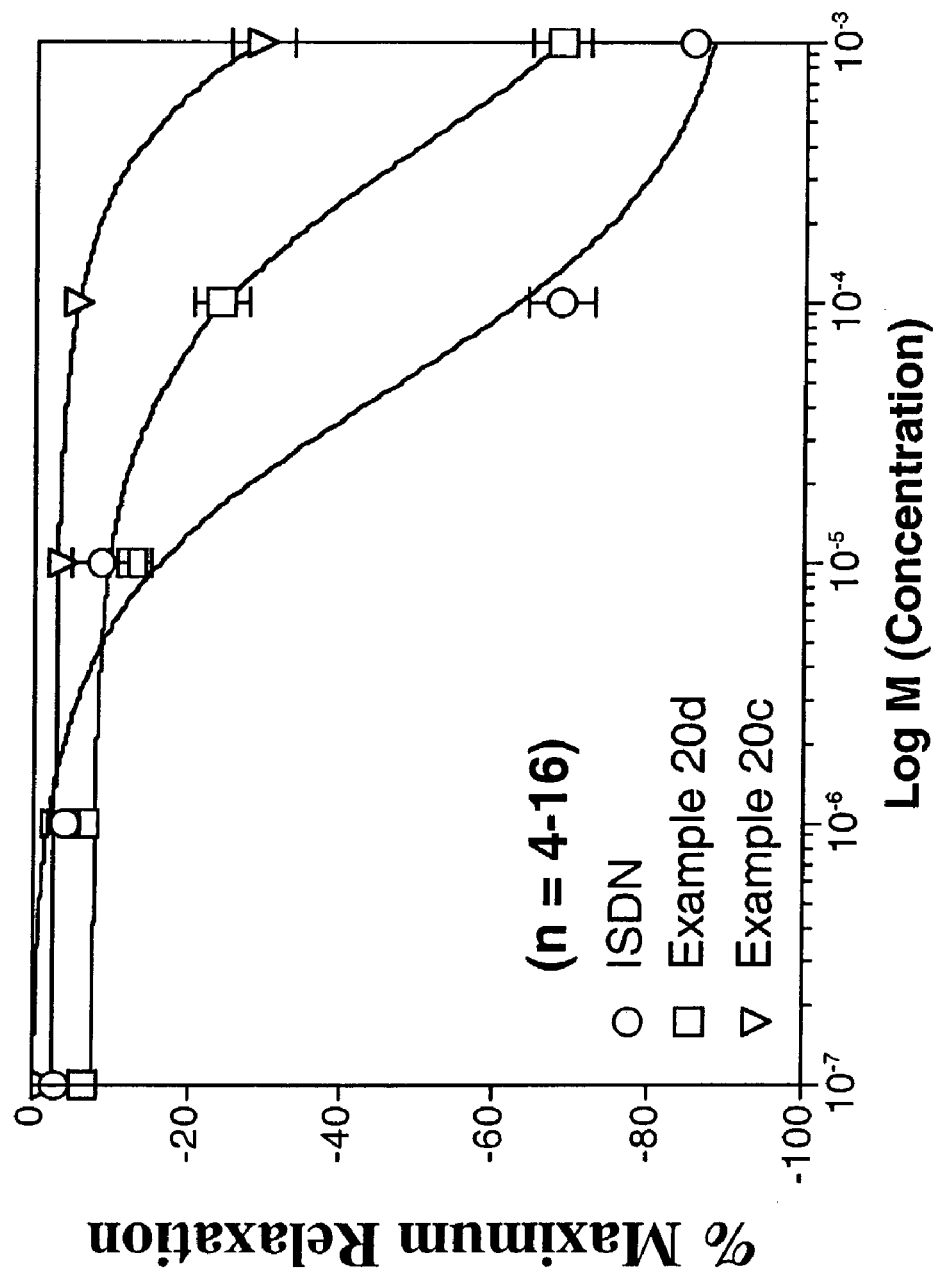
FIG. 4 shows the relaxation of rat aortic smooth muscle rings by (a) isosorbide dinitrate (ISDN, open circles); (b) Example 20c (non-nitrosated compound, open inverted triangles); and (c) Example 20d (nitrosated compound, open squares). The non-nitrosated compound of Example 20c did not relax the tissue. At higher concentrations, the relaxation of the nitrosated compound of Example 20d was comparable to that obtained with ISDN. Total number of samples tested varied from a minimum of 4 to a maximum of 16. In the x axis, log M corresponds to ten fold increases of the test compound from 100 nM ($10^{-7}$) to 100 μM ($10^{-4}$). Results are expressed as the mean±standard error of the mean of the percentage of total relaxation induced by 10 μM phenylephrine.

The tissue was prepared according to Example 23. The percent contraction of phenylephrine-contracted aortic smooth muscle rings induced by isosorbide dinitrate (ISDN), Example 20d and Example 20e (nitrate) was measured. FIG. 4 shows that the parent non-nitrosylated compound, Example 20d, did not relax the aortic ring. The nitrosated compound, Example 20e, induced the relaxation of the aortic ring. The observed relaxation was similar to that obtained by the nitrate compound, isosorbide dinitrate.

Example 28

Anti-Inflammatory Paw Edema Test for Example 2

The carrageenan-induced rat paw edema test was used to measure antiinflammatory activity. The paw edema test was performed according to the method of Winter et al, *Proc. Soc. Exp. Biol. Med.* 111: 544–547, 1962. Male Sprague-Dawley rats (200–250 g) were fasted for 24 hours with water ad libitum. The rats were dosed intragastrically with test compounds in a volume of 5 mL/kg. One hour after dosing the paw volume was measured. Then each rat received a subplantar injection of 50 µl of 1% suspension of carrageenan. Three hours later, the paw volume was measured and compared with the initial volume measured immediately after carrageenan injection. The increase in paw volume is presented as the mean±SEM for 5 rats per group. Data were analyzed by performing an ANOVA test followed by a Student-Keuls post hoc test.

FIG. 5 shows that the parent non-nitrosated compound Example 2a, the nitrosated compound Example 2b and Celecoxib all reduced the paw volume and, hence, these compounds have antiinflammatory activity. Thus, nitrosation did not effect the COX-2 inhibition properties of the compounds.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the present invention.

What is claimed is:

1. A compound of Formula (III) or a pharmaceutically acceptable salt thereof:

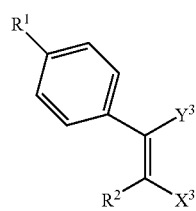

III wherein:
$R^1$ is:
(a) —$S(O)_2$—$CH_3$;
(b) —$S(O)_2$—$NR^8(D^1)$;
(c) —$S(O)_2$—$N(D^1)$—$C(O)$—$CF_3$;
(d) —$S(O)$—$(NH)$—$NH(D^1)$;
(e) —$S(O)$—$(NH)$—$N(D^1)$—$C(O)$—$CF_3$;
(f) —$P(O)(CH_3)NH(D^1)$;
(g) —$P(O)(CH_3)_2$;
(h) —$C(S)$—$NH(D^1)$;
(i) —$S(O)(NH)CH_3$;
(j) —$P(O)(CH_3)OD^1$; or
(k) —$P(O)(CH_3)NH(D^1)$;
$R^2$ is:
(a) lower alkyl;
(b) cycloalkyl;
(c) mono-, di- or tri-substituted phenyl or naphthyl, wherein the substituents are each independently:
(1) hydrogen;
(2) halo;
(3) alkoxy;
(4) alkylthio;
(5) CN;
(6) haloalkyl;
(7) lower alkyl;
(8) $N_3$;
(9) —$CO_2D^1$;
(10) —$CO_2$-lower alkyl;
(11) —$(C(R^5)(R^6))_z$—$OD^1$;
(12) —$(C(R^5)(R^6))_z$—O-lower alkyl;
(13) lower alkyl-$CO_2$—$R^5$;
(14) —$OD^1$;
(15) haloalkoxy;
(16) amino;
(17) nitro;
(18) alkylsulfinyl; or
(19) heteroaryl;
(d) mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; wherein the substituents are each independently:
(1) hydrogen;
(2) halo;
(3) lower alkyl;
(4) alkoxy;
(5) alkylthio;
(6) CN;
(7) haloalkyl;
(8) $N_3$;
(9) —$C(R^5)(R^6)$—$OD^1$;
(10) —$C(R^5)(R^6)$—O-lower alkyl; or
(11) alkylsulfinyl;
(e) benzoheteroaryl which includes the benzo fused analogs of (d);
(f) —$NR^{10}R^{11}$;
(g) —$SR^{11}$;
(h) —$OR^{11}$;
(j) alkenyl;
(k) alkynyl;
(l) unsubstituted, mono-, di-, tri- or tetra-substituted cycloalkenyl, wherein the substituents are each independently:
(1) halo;
(2) alkoxy;
(3) alkylthio;
(4) CN;
(5) haloalkyl;

(6) lower alkyl;
(7) N$_3$;
(8) —CO$_2$D$^1$;
(9) —CO$_2$-lower alkyl;
(10) —C(R$^{12}$)(R$^{13}$)—OD$^1$;
(11) —C(R$^{12}$)(R$^{13}$)—O-lower alkyl;
(12) lower alkyl-CO$_2$—R$^{12}$;
(13) benzyloxy;
(14) —O—(lower alkyl)—CO$_2$R$^{12}$;
(15) —O—(lower alkyl)—NR$^{12}$R$^{13}$; or
(16) alkylsulfinyl;
(m) mono-, di-, tri- or tetra-substituted heterocycloalkyl group of 5, 6 or 7 members, or a benzoheterocycle, wherein said heterocycloalkyl or benzoheterocycle has 1 or 2 heteroatoms selected from O, S, or N and, optionally, a carbonyl group or a sulfonyl group, and wherein said substituents are each independently:
(1) halo;
(2) lower alkyl;
(3) alkoxy;
(4) alkylthio;
(5) CN;
(6) haloalkyl;
(7) N$_3$;
(8) —C(R$^{12}$)(R$^{13}$)—OD$^1$;
(9) —C(R$^{12}$)(R$^{13}$)—O-lower alkyl; or
(10) alkylsulfinyl;
(n) styryl, mono or di-substituted styryl, wherein the substituent are each independently:
(1) halo;
(2) alkoxy;
(3) alkylthio;
(4) CN;
(5) haloalkyl;
(6) lower alkyl;
(7) N$_3$;
(8) —CO$_2$D$^1$;
(9) —CO$_2$-lower alkyl;
(10) —C(R$^{12}$)(R$^{13}$)—OD$^1$;
(11) —C(R$^{12}$)(R$^{13}$)—O-lower alkyl;
(12) lower alkyl-CO$_2$—R$^{12}$;
(13) benzyloxy;
(14) —O—(lower alkyl)—CO$_2$R$^{12}$; or
(15) —O—(lower alkyl)—NR$^{12}$R$^{13}$;
(o) phenylacetylene, mono- or di-substituted phenylacetylene, wherein the substituents are each independently:
(1) halo;
(2) alkoxy;
(3) alkylthio;
(4) CN;
(5) haloalkyl;
(6) lower alkyl;
(7) N$_3$;
(8) —CO$_2$D$^1$;
(9) —CO$_2$-lower alkyl;
(10) —C(R$^{12}$)(R$^{13}$)—OD$^1$;
(11) —C(R$^{12}$)(R$^{13}$)—O-lower alkyl;
(12) lower alkyl-CO$_2$—R$^{12}$;
(13) benzyloxy;
(14) —O—(lower alkyl)—CO$_2$R$^{12}$; or
(15) —O—(lower alkyl)—NR$^{12}$R$^{13}$;
(p) fluoroalkenyl;
(q) mono- or di-substituted bicyclic heteroaryl of 8, 9 or 10 members, consisting of 2, 3, 4 or 5 heteroatoms, wherein at least one heteroatom resides on each ring of said bicyclic heteroaryl, said heteroatoms are each independently O, S and N and said substituents are each independently:
(1) hydrogen;
(2) halo;
(3) lower alkyl;
(4) alkoxy;
(5) alkylthio;
(6) CN;
(7) haloalkyl;
(8) N$_3$;
(9) —C(R$^5$)(R$^6$)—OD$^1$; or
(10) —C(R$^5$)(R$^6$)—O-lower alkyl;
(r) K;
(s) aryl;
(t) arylalkyl;
(u) cycloalkylalkyl;
(v) —C(O)R$^{11}$;
(u) hydrogen;
(v) arylalkenyl;
(w) arylalkoxy;
(x) alkoxy;
(y) aryloxy;
(z) cycloalkoxy;
(aa) arylthio;
(bb) alkylthio;
(cc) arylalkylthio; or
(dd) cycloalkylthio;
X$^3$ is:
(a) —C(O)—U—D$^1$;
(b) —CH$_2$—U—D$^1$;
(c) —CH$_2$—C(O)—CH$_3$;
(d) —CH$_2$—CH$_2$—C(O)—U—D$^1$;
(e) —CH$_2$—O—D$^1$; or
(f) —C(O)H
Y$^3$ is:
(a) —(CR$^5$(R$^{5\prime}$))$_k$—U—D$^1$;
(b) —CH$_3$;
(c) —CH$_2$OC(O)R$^6$; or
(d) —C(O)H;
alternatively, X$^3$ and Y$^3$ taken together are —CR$^{82}$(R$^{83}$)—CR$^{82\prime}$(R$^{83\prime}$)—;
R$^{82}$, R$^{82\prime}$, R$^{83}$ and R$^{83\prime}$ are each independently:
(a) hydrogen;
(b) hydroxy;
(c) alkyl;
(d) alkoxy;
(e) lower alkyl-OD$^1$;
(f) alkylthio;
(g) CN;
(h) —C(O)R$^{84}$; or
(i) —OC(O)R$^{85}$;
R$^{84}$ is:
(a) hydrogen;
(b) lower alkyl; or
(c) alkoxy;
R$^{85}$ is:
(a) lower alkyl;
(b) alkoxy
(c) unsubstituted, mono-, di- or tn-substituted phenyl or pyridyl, wherein the substituents are each independently:
(1) halo;
(2) alkoxy;
(3) haloalkyl;
(4) CN;
(5) —C(O)R$^{84}$;

(6) lower alkyl;
(7) —S(O)$_o$-lower alkyl; or
(8) —OD$^1$;

alternatively, R$^{82}$ and R$^{83}$ or R$^{82'}$ and R$^{83'}$ taken together are:
(a) oxo;
(b) thial;
(c) =CR$^{86}$R$^{87}$; or
(d) =NR$^{88}$;

R$^{86}$ and R$^{87}$ are each independently:
(a) hydrogen;
(b) lower alkyl;
(c) lower alkyl-OD$^1$;
(d) CN; or
(e) —C(O)R$^{84}$;

R$^{88}$ is:
(a) OD$^1$;
(b) alkoxy;
(c) lower alkyl; or
(d) unsubstituted, mono-, di- or tri-substituted phenyl or pyridyl, wherein the substituents are each independently:
(1) halo;
(2) alkoxy;
(3) haloalkyl;
(4) CN;
(5) —C(O)R$^{84}$;
(6) lower alkyl;
(7) —S(O)$_o$-lower alkyl; or
(8) —OD$^1$;

R$^5$ and R$^{5'}$ are each independently:
(a) hydrogen;
(b) amino;
(c) CN;
(d) lower alkyl;
(e) haloalkyl;
(f) alkoxy;
(g) alkylthio;
(h) Q;
(i) —O—Q;
(j) —S—Q;
(k) K;
(l) cycloalkoxy;
(m) cycloalkylthio;
(n) unsubstituted, mono-, or di-substituted phenyl or unsubstituted, mono-, or di-substituted benzyl, wherein the substituents are each independently:
(1) halo;
(2) lower alkyl;
(3) alkoxy;
(4) alkylthio;
(5) CN;
(6) haloalkyl;
(7) N$_3$;
(8) Q;
(9) nitro; or
(10) amino;
(o) unsubstituted, mono-, or di-substituted heteroaryl or unsubstituted, mono-, or di-substituted heteroarylmethyl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; said substituents are each independently:
(1) halo;
(2) lower alkyl;
(3) alkoxy;
(4) alkylthio;
(5) CN;
(6) haloalkyl;
(7) N$_3$;
(8) —C(R$^6$)(R$^7$)—OD$^1$;
(9) —C(R$^6$)(R$^7$)—O-lower alkyl; or
(10) alkylsulfinyl
(p) —CON(R$^8$)(R$^8$);
(q) —CH$_2$OR$^8$;
(r) —CH$_2$OCN;
(s) unsubstituted or substituted:
(1) lower alkyl-Q;
(2) —O-lower alkyl-Q;
(3) —S-lower alkyl-Q;
(4) lower alkyl-O-lower alkyl-Q;
(5) lower alkyl-S-lower alkyl-Q;
(6) lower alkyl-O—Q;
(7) lower alkyl-S—Q;
(8) lower alkyl-O—K;
(9) lower alkyl-S—K;
(10) lower alkyl-O—V; or
(11) lower alkyl-S—V;
wherein the substituent(s) resides on the lower alkyl;
(t) cycloalkyl;
(u) aryl;
(v) arylalkyl;
(w) cycloalkylalkyl;
(x) aryloxy;
(y) arylalkoxy;
(z) arylalkylthio;
(aa) cycloalkylalkoxy;
(bb) heterocycloalkyl;
(cc) alkylsulfonyloxy;
(dd) alkylsulfonyl;
(ee) arylsulfonyl;
(ff) arylsulfonyloxy;
(gg) —C(O)R$^{10}$;
(hh) nitro;
(ii) amino;
(jj) aminoalkyl;
(kk) —C(O)-alkyl-heterocyclic ring;
(ll) halo;
(mm) heterocyclic ring;
(nn) —CO$_2$D$^1$;
(oo) carboxyl;
(pp) amidyl; or
(qq) alkoxyalkyl;

alternatively, R$^5$ and R$^{5'}$ taken together with the carbon to which they are attached are:
(a) cycloalkyl; or
(b) heterocyclic ring;

R$^6$ and R$^7$ are each independently:
(a) hydrogen;
(b) unsubstituted, mono- or di-substituted phenyl; unsubstituted, mono- or di-substituted benzyl; unsubstituted, mono- or di-substituted heteroaryl; mono- or di-substituted heteroarylmethyl, wherein said substituents are each independently:
(1) halo;
(2) lower alkyl;
(3) alkoxy;
(4) alkylthio;
(5) CN;
(6) haloalkyl;

(7) $N_3$;
(8) —C($R^{14}$)($R^{15}$)—$OD^1$; or
(9) —C($R^{14}$)($R^{15}$)—O-lower alkyl;
(c) lower alkyl;
(d) —$CH_2OR^8$;
(e) CN;
(f) —$CH_2CN$;
(g) haloalkyl;
(h) —CON($R^8$)($R^8$);
(i) halo; or
(j) —$OR^8$;

$R^8$ is:
(a) hydrogen;
(b) K; or
(c) $R^9$;

alternatively, $R^5$ and $R^{5'}$, $R^6$ and $R^7$ or $R^7$ and $R^8$ together with the carbon to which they are attached form a saturated monocyclic ring of 3, 4, 5, 6 or 7 atoms; and optionally up to two heteroatoms selected from oxygen, S(O)$_o$ or $NR_i$;

$R^9$ is:
(a) lower alkyl;
(b) lower alkyl-$CO_2D^1$;
(c) lower alkyl-$NHD^1$;
(d) phenyl or mono-, di- or tri-substituted phenyl, wherein the substituents are each independently:
  (1) halo;
  (2) lower alkyl;
  (3) alkoxy;
  (4) alkylthio;
  (5) lower alkyl-$CO_2D^1$;
  (6) lower alkyl-$NHD^1$;
  (7) CN;
  (8) $CO_2D^1$; or
  (9) haloalkyl;
(e) benzyl, mono-, di- or tri-substituted benzyl, wherein the substituents are each independently:
  (1) halo;
  (2) lower alkyl;
  (3) alkoxy;
  (4) alkylthio;
  (5) lower alkyl-$CO_2D^1$;
  (6) lower alkyl-$NHD^1$;
  (7) CN;
  (8) -$CO_2D^1$; or
  (9) haloalkyl;
(f) cycloalkyl;
(g) K; or
(h) benzoyl, mono-, di-, or trisubstituted benzoyl, wherein the substituents are each independently:
  (1) halo;
  (2) lower alkyl;
  (3) alkoxy;
  (4) alkylthio;
  (5) lower alkyl-$CO_2D^1$;
  (6) lower alkyl-$NHD^1$;
  (7) CN;
  (8) —$CO_2D^1$; or
  (9) haloalkyl;

$R^{10}$ is:
(a) hydrogen; or
(b) $R^{11}$;

$R^{11}$ is:
(a) lower alkyl;
(b) cycloalkyl;
(c) unsubstituted, mono-, di- or tri-substituted phenyl or naphthyl, wherein the substituents are each independently:
  (1) halo;
  (2) alkoxy;
  (3) alkylthio;
  (4) CN;
  (5) haloalkyl;
  (6) lower alkyl;
  (7) $N_3$;
  (8) —$CO_2D^1$;
  (9) —$CO_2$-lower alkyl;
  (10) —C($R^{12}$)($R^{13}$)—$OD^1$;
  (11) —C($R^{12}$)($R^{13}$)—O-lower alkyl;
  (12) lower alkyl-$CO_2D^1$;
  (13) lower alkyl-$CO_2R^{12}$;
  (14) benzyloxy;
  (15) —O-(lower alkyl)-$CO_2D^1$;
  (16) —O-(lower alkyl)-$CO_2R^{12}$; or
  (17) —O-(lower alkyl)-$NR^{12}R^{13}$;
(d) unsubstituted, mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or said heteroaryl is a monocyclic ring of 6 atoms, said ring having one heteroatom which is N, and, optionally 1, 2, or 3 additional N atoms, and wherein said substituents are each independently:
  (1) halo;
  (2) lower alkyl;
  (3) alkoxy;
  (4) alkylthio;
  (5) CN;
  (6) haloalkyl;
  (7) $N_3$;
  (8) —C($R^{12}$)($R^{13}$)—$OD^1$; or
  (9) —C($R^{12}$)($R^{13}$)—O-lower alkyl;
(e) unsubstituted, mono- or di-substituted benzoheterocycle, wherein the benzoheterocycle is a 5, 6, or 7-membered ring with 1 or 2 heteroatoms independently selected from O, S, or N, and, optionally, a carbonyl group or a sulfonyl group, wherein said substituents are each independently:
  (1) halo;
  (2) lower alkyl;
  (3) alkoxy;
  (4) alkylthio;
  (5) CN;
  (6) haloalkyl;
  (7) $N_3$;
  (8) —C($R^{12}$)($R^{13}$)—$OD^1$; or
  (9) —C($R^{12}$)($R^{13}$)—O-lower alkyl;
(f) unsubstituted, mono- or di-substituted benzocarbocycle, wherein the carbocycle is a 5, 6, or 7-membered ring has optionally a carbonyl group, wherein said substituents are each independently:
  (1) halo;
  (2) lower alkyl;
  (3) alkoxy;
  (4) alkylthio;
  (5) CN;
  (6) haloalkyl;
  (7) $N_3$;
  (8) —C($R^{12}$)($R^{13}$)—$OD^1$; or
  (9) —C($R^{12}$)($R^{13}$)—O-lower alkyl;
(g) hydrogen; or
(h) K $R^{12}$ and $R^{13}$ are each independently:
  (a) hydrogen;
  (b) lower alkyl; or
  (c) aryl; or
$R^{12}$ and $R^{13}$ together with the atom to which they are attached form a saturated monocyclic ring of 3, 4, 5, 6 or 7 atoms;
$R^{14}$ and $R^{15}$ are each independently:
  (a) hydrogen; or
  (b) lower alkyl; or
$R^{14}$ and $R^{15}$ together with the atom to which they are attached form a carbonyl, a thial, or a saturated monocyclic ring of 3, 4, 5, 6 or 7 atoms;
$D^1$ is:
  (a) hydrogen or
  (b) D;
D is:
  (a) V; or
  (b) K;
U is:
  (a) oxygen;
  (b) sulfur; or
  (c) —$N(R_a)R_i$—;
V is:
  (a) —NO;
  (b) —$NO_2$; or
  (c) hydrogen
K is —$W_{aa}$—$E_b$—$(C(R_e)(R_f))_p$—$E_c$—$(C(R_e)(R_f))_x$—$W_d$—$(C(R_e)(R_f))_y$—$W_i$—$E_j$—$W_g$—$(C(R_e)(R_f))_z$—U—V; wherein aa, b, c, d, g, i and j are each independently an integer from 0 to 3;
p, x, y and z are each independently an integer from 0 to 10;
W at each occurrence is independently:
  (a) —C(O)—;
  (b) —C(S)—;
  (c) —T—;
  (d) —$(C(R_e)(R_f))_h$—;
  (e) alkyl;
  (f) aryl;
  (g) heterocyclic ring;
  (h) arylheterocyclic ring, or
  (i) —$(CH_2CH_2O)_q$—;
E at each occurrence is independently:
  (a) —T—;
  (b) alkyl;
  (c) aryl;
  (d) —$(C(R_e)(R_f))_h$—;
  (e) heterocyclic ring;
  (f) arylheterocyclic ring; or
  (g) —$(CH_2CH_2O)_q$—;
h is an integer form 1 to 10;
q is an integer from 1 to 5;
$R_e$ and $R_f$ are each independently:
  (a) hydrogen;
  (b) alkyl;
  (c) cycloalkoxy;
  (d) halogen;
  (e) hydroxy;
  (f) hydroxyalkyl;
  (g) alkoxyalkyl;
  (h) arylheterocyclic ring;
  (i) cycloalkylalkyl;
  (j) heterocyclicalkyl;
  (k) alkoxy;
  (l) haloalkoxy;
  (m) amino;
  (n) alkylamino;
  (o) dialkylamino;
  (p) arylamino;
  (q) diarylamino;
  (r) alkylarylamino;
  (s) alkoxyhaloalkyl;
  (t) haloalkoxy;
  (u) sulfonic acid;
  (v) alkylsulfonic acid;
  (w) arylsulfonic acid;
  (x) arylalkoxy;
  (y) alkylthio;
  (z) arylthio;
  (aa) cyano;
  (bb) aminoalkyl;
  (cc) aminoaryl;
  (dd) alkoxy;
  (ee) aryl;
  (ff) arylalkyl;
  (gg) carboxamido;
  (hh) alkylcarboxamido;
  (ii) arylcarboxamido;
  (jj) amidyl;
  (kk) carboxyl;
  (ll) carbamoyl;
  (mm) alkylcarboxylic acid;
  (nn) arylcarboxylic acid;
  (oo) alkylcarbonyl;
  (pp) arylcarbonyl;
  (qq) ester;
  (rr) carboxylic ester;
  (ss) alkylcarboxylic ester;
  (tt) arylcarboxylic ester;
  (uu) haloalkoxy;
  (vv) sulfonamido;
  (ww) alkylsulfonamido;
  (xx) arylsulfonamido;
  (yy) alkylsulfonyl,
  (zz) alkylsulfonyloxy,
  (aaa) arylsulfonyl,
  (bbb) arylsulphonyloxy
  (ccc) sulfonic ester;
  (ddd) carbamoyl;
  (eee) urea;
  (fff) nitro; or
  (ggg) —U—V; or
$R_e$ and $R_f$ taken together are:
  (a) oxo;
  (b) thial; or
$R_e$ and $R_f$ taken together with the carbon to which they are attached are:
  (a) heterocyclic ring;
  (b) cycloalkyl group; or
  (c) bridged cycloalkyl group;
k is an integer from 1 to 2;
T at each occurrence is independently:
  (a) a covalent bond,
  (b) carbonyl,
  (c) an oxygen,
  (d) —$S(O)_o$—; or
  (e) —$N(R_a)R_i$—;
o is an integer from 0 to 2;
Q is:
  (a) —C(O)—U—$D^1$;
  (b) —$CO_2$-lower alkyl;
  (c) tetrazolyl-5-yl;
  (d) —$C(R^7)(R^8)(S—D^1)$;

(e) —C(R$^7$)(R$^8$)(O—D$^1$); or
(f) —C(R$^7$)(R$^8$)(O-lower alkyl);

R$_a$ is:
(a) a lone pair of electron;
(b) hydrogen; or
(c) lower alkyl;

R$_i$ is:
(a) hydrogen;
(b) alkyl;
(c) aryl;
(d) alkylcarboxylic acid;
(e) arylcarboxylic acid;
(f) alkylcarboxylic ester;
(g) arylcarboxylic ester;
(h) alkylcarboxamido;
(i) arylcarboxamido;
(j) alkylsulfinyl;
(k) alkylsulfonyl;
(l) alkylsulfonyloxy,
(m) arylsulfinyl;
(n) arylsulfonyl;
(o) arylsulphonyloxy;
(p) sulfonamido;
(q) carboxamido;
(r) carboxylic ester;
(s) aminoalkyl;
(t) aminoaryl;
(u) —CH$_2$—C(U—V)(R$_e$)(R$_f$);
(v) a bond to an adjacent atom creating a double bond to that atom; or
(w) —(N$_2$O$_2$—)$^-$·M$^+$, wherein M$^+$ is an organic or inorganic cation;

with the proviso that the compound of Formula III must contain at least one nitrite, nitrate, thionitrite or thionitrate group.

2. A composition comprising the compound of claim 1 and a pharmaceutically acceptable carrier.

3. The composition of claim 2, further comprising at least one therapeutic agent.

4. The composition of claim 3, wherein the therapeutic agent is a steroid, a nonsteroidal antiinflammatory compound, a 5-lipoxygenase inhibitor, a leukotriene B$_4$ receptor antagonist, a leukotriene A$_4$ hydrolase inhibitor, a 5-HT agonist, a 3-hydroxy-3-methylglutaryl coenzyme A inhibitor, a H$_2$ receptor antagonist, an antineoplastic agent, an antiplatelet agent, a decongestant, a diuretic, a sedating or non-sedating anti-histamine, an inducible nitric oxide synthase inhibitor, an opioid, an analgesic, a *Helicobacter pylori* inhibitor, a proton pump inhibitor, an isoprostane inhibitor, or a mixture of two or more thereof.

5. The composition of claim 4, wherein the nonsteroidal antiinflammatory compound is acetaminophen, aspirin, diclofenac, ibuprofen, ketoprofen or naproxen.

6. A composition comprising at least one compound of claim 1 and at least one compound that donates, transfers or releases nitric oxide, or induces the production of endogenous nitric oxide or endothelium-derived relaxing factor, or is a substrate for nitric oxide synthase.

7. The composition of claim 6, further comprising a pharmaceutically acceptable carrier.

8. The composition of claim 6, wherein the compound that donates, transfers, or releases nitric oxide, or induces the production of endogenous nitric oxide or endothelium-derived relaxing factor or is a substrate for nitric oxide synthase is an S-nitrosothiol.

9. The composition of claim 8, wherein the S-nitrosothiol is S-nitroso-N-acetylcysteine, S-nitroso-captopril, S-nitroso-N-acetylpenicillamine, S-nitroso-homocysteine, S-nitroso-cysteine, S-nitroso-glutathione, or S-nitroso-cysteinylglycine.

10. The composition of claim 8, wherein the S-nitrosothiol is:
(i) HS(C(R$_e$)(R$_f$))$_{mm}$SNO;
(ii) ONS(C(R$_e$)(R$_f$))$_{mm}$R$_e$; or
(iii) H$_2$N—CH(CO$_2$H)—(CH$_2$)$_{mm}$—C(O)NH—CH(CH$_2$SNO)—C(O)NH—CH$_2$—CO$_2$H;

wherein mm is an integer from 2 to 20; R$_e$ and R$_f$ are each independently a hydrogen, an alkyl, a cycloalkoxy, a halogen, a hydroxy, an hydroxyalkyl, an alkoxyalkyl, an arylheterocyclic ring, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an alkoxy, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, alkylsulfonamido, an arylsulfonamido, an alkylsulfonyl, an alkylsulfonyloxy, an arylsulfonyl, an arylsulfonyloxy, a carbamoyl, a urea, a nitro, —T—Q—, or (C(R$_e$)(R$_f$))$_k$—T—Q, or R$_e$ and R$_f$ taken together are an oxo, a methanthial, a heterocyclic ring, a cycloalkyl group or a bridged cycloalkyl group; Q is —NO or —NO$_2$; and T is independently a covalent bond, a carbonyl, an oxygen, —S(O)$_o$—or —N(R$_a$)R$_i$—, wherein o is an integer from 0 to 2, R$_a$ is a lone pair of electrons, a hydrogen or an alkyl group; R$_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyl arylsulfinyl, an arylsulfonyloxy, an arylsulfonyl, a sulfonamido, a carboxamido, a carboxylic ester, an aminoalkyl, an aminoaryl, —CH$_2$C(T—Q)(R$_e$)(R$_f$), or —(N$_2$O$_2$—)$^{31}$ ·M$^+$, wherein M+ is an organic or inorganic cation; with the proviso that when R$_i$ is —CH$_2$—C(T—Q)(R$_e$)(R$_f$) or —(N$_2$O$_2$—).M$^+$; then "—T—Q" can be a hydrogen, an alkyl group, an alkoxyalkyl group, an aminoalkyl group, a hydroxy group or an aryl group.

11. The composition of claim 6, wherein the compound that donates, transfers, or releases nitric oxide, or induces the production of endogenous nitric oxide or endothelium-derived relaxing factor, or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine, or an arginase inhibitor.

12. The composition of claim 6, wherein the compound that donates, transfers, or releases nitric oxide, or induces the production of endogenous nitric oxide or endothelium-derived relaxing factor, or is a substrate for nitric oxide synthase is:
(i) a compound that comprises at least one ON—O—, ON—N—or ON—C-group;
(ii) a compound that comprises at least one O$_2$N—O—, O$_2$N—N—, O$_2$N—S— or —O$_2$N—C— group;
(iii) a N-oxo-N-nitrosoamine having the formula: R$^1$R$^2$N—N(O—M$^+$)—NO, wherein R$^1$ and R$^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and M+ is an organic or inorganic cation.

13. The composition of claim 12, wherein the compound comprising at least one ON—O—, ON—N—or ON—C—group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

14. The composition of claim 12, wherein compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C -sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

15. The composition of claim 6, further comprising at least one therapeutic agent.

16. The composition of claim 15, wherein the therapeutic agent is a steroid, a nonsteroidal antiinflammatory compound, a 5-lipoxygenase inhibitor, a leukotriene $B_4$ receptor antagonist, a leukotriene $A_4$ hydrolase inhibitor, a 5-HT agonist, a 3-hydroxy-3-methylglutaryl coenzyme A inhibitor, a $H_2$ receptor antagonist, an antineoplastic agent, an antiplatelet agent, a decongestant, a diuretic, a sedating or non-sedating anti-histamine, an inducible nitric oxide synthase inhibitor, an opioid, an analgesic, a *Helicobacter pylori* inhibitor, a proton pump inhibitor, an isoprostane inhibitor, or a mixture of two or more thereof.

17. The composition of claim 16, wherein the nonsteroidal antiinflammatory compound is acetaminophen, aspirin, diclofenac, ibuprofen, ketoprofen or naproxen.

18. A kit comprising at least one compound of claim 1.

19. The kit of claim 18, further comprising (i) at least one compound that donates, transfers or releases nitric oxide, induces the production of endogenous nitric oxide or endothelium-derived relaxing factor, or is a substrate for nitric oxide synthase; (ii) at least one therapeutic agent; or (iii) at least one compound that donates, transfers or releases nitric oxide, induces the production of endogenous nitric oxide or endothelium-derived relaxing factor, or is a substrate for nitric oxide synthase and at least one therapeutic agent.

20. The kit of claim 19, wherein the at least one compound that donates, transfers or releases nitric oxide, induces the production of endogenous nitric oxide or endothelium-derived relaxing factor, or is a substrate for nitric oxide synthase; the at least one therapeutic agent; or the at least one compound that donates, transfers or releases nitric oxide, induces the production of endogenous nitric oxide or endothelium-derived relaxing factor, or is a substrate for nitric oxide synthase and at least one therapeutic agent; are in the form of separate components in the kit.

21. A kit comprising the composition of claim 3, 7 or 15.

22. A compound selected from the group consisting of 3-(4-(1-methyl-1-(nitrosothio)ethyl)-2-oxo-1,3-oxazolidin-3-yl)propyl (2Z)-4-acetyloxy-2-(4-flurophenyl)-3-(4-(methylsulfonyl) phenyl)but-2-enoate or a pharmaceutically acceptable salt thereof; (2Z)-3-(4-fluorophenyl)-3-(N-methyl-N-(2-methyl-2-(nitrosothio)propyl) carbamoyl)-2-(4-(methylsulfonyl)phenyl)prop-2-enyl acetate or a pharmaceutically acceptable salt thereof; and 2-(1-methyl-4-(nitrosothio)-4-piperidyl)ethyl (2Z)-3-(4-acetyloxy-2-(4-fluorophenyl)-3-4-(methylsulfonyl)phenyl)but-2-enoate or a pharmaceutically acceptable salt thereof.

23. A composition comprising at least one compound of claim 22 and a pharmaceutically acceptable carrier.

24. The composition of claim 23, further comprising (i) at least one compound that donates, transfers or releases nitric oxide, induces the production of endogenous nitric oxide or endothelium-derived relaxing factor, or is a substrate for nitric oxide synthase; (ii) at least one therapeutic agent; or (iii) at least one compound that donates, transfers or releases nitric oxide, induces the production of endogenous nitric oxide or endothelium-derived relaxing factor, or is a substrate for nitric oxide synthase and at least one therapeutic agent.

25. A kit comprising at least one compound of claim 22.

26. A compound of Formula (III) or a pharmaceutically acceptable salt thereof:

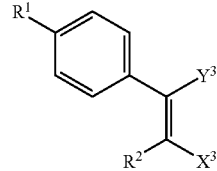

III wherein:
$R^1$ is —S(O)$_2$—CH$_3$;
$R^2$ is a mono-, di- or tri-substituted phenyl or naphthyl, wherein the substituents are each independently:
  (1) hydrogen;
  (2) halo;
  (3) alkoxy;
  (4) alkylthio;
  (5) CN;
  (6) haloalkyl; or
  (7) lower alkyl;
$X^3$ is —C(O)—U—D$^1$;
$Y^3$ is —CH$_2$OC(O)R$^6$;
$R^6$ is a lower alkyl group;
$D^1$ is D;
D is:
  (a) V; or
  (b) K;
U is:
  (a) oxygen;
  (b) sulfur; or
  (c) —N(R$_a$)R$_i$—;
V is:
  (a) —NO;
  (b) —NO$_2$; or
  (c) hydrogen K is —$W_{aa}$—$E_b$—$(C(R_e)(R_f))_p$$E_c$—$(C(R_e)(R_f))_x$—$W_d$—$(C(R_e)(R_f))_y$—$W_i$—$E_j$—$W_g$—$(C(R_e)(R_f))_z$—U—V;
wherein aa, b, c, d, g, i and j are each independently an integer from 0 to 3;
p, x, y and z are each independently an integer from 0 to 10;
W at each occurrence is independently:
- (a) —C(O)—;
- (b) —C(S)—;
- (c) —T—;
- (e) alkyl;
- (f) aryl;
- (g) heterocyclic ring;
- (h) arylheterocyclic ring, or
- (i) —$CH_2CH_2O)_q$—;

E at each occurrence is independently:
- (a) —T—;
- (b) alkyl;
- (c) aryl;
- (e) heterocyclic ring;
- (f) arylheterocyclic ring; or
- (g) —$(CH_2CH_2O)_q$—;

h is an integer form 1 to 10;
q is an integer from 1 to 5;
$R_e$ and $R_f$ are each independently:
- (a) hydrogen;
- (b) alkyl;
- (c) cycloalkoxy;
- (d) halogen;
- (e) hydroxy;
- (f) hydroxyalkyl;
- (g) alkoxyalkyl;
- (h) arylheterocyclic ring;
- (I) cycloalkylalkyl;
- (j) heterocyclicalkyl;
- (k) alkoxy;
- (l) haloalkoxy;
- (m) amino;
- (n) alkylamino;
- (o) dialkylamino;
- (p) arylamino;
- (q) diarylamino;
- (r) alkylarylamino;
- (s) alkoxyhaloalkyl;
- (t) haloalkoxy;
- (u) sulfonic acid;
- (v) alkylsulfonic acid;
- (w) arylsulfonic acid;
- (x) arylalkoxy;
- (y) alkylthio;
- (z) arylthio;
- (aa) cyano;
- (bb) aminoalkyl;
- (cc) aminoaryl;
- (dd) alkoxy;
- (ee) aryl;
- (ff) arylalkyl;
- (gg) carboxamido;
- (hh) alkylcarboxamido;
- (ii) arylcarboxamido;
- (jj) amidyl;
- (kk) carboxyl;
- (ll) carbamoyl;
- (mm) alkylcarboxylic acid;
- (nn) arylcarboxylic acid;
- (oo) alkylcarbonyl;
- (pp) arylcarbonyl;
- (qq) ester;
- (rr) carboxylic ester;
- (ss) alkylcarboxylic ester;
- (tt) arylcarboxylic ester;
- (uu) haloalkoxy;
- (vv) sulfonamido;
- (ww) alkylsulfonamido;
- (xx) arylsulfonamido;
- (yy) alkylsulfonyl,
- (zz) alkylsulfonyloxy,
- (aaa) arylsulfonyl,
- (bbb) arylsulphonyloxy
- (ccc) sulfonic ester;
- (ddd) carbamoyl;
- (eee) urea;
- (fff) nitro; or
- (ggg) —U—V; or $R_e$ and $R_f$ taken together are:
- (a) oxo;
- (b) thial; or $R_e$ and $R_f$ taken together with the carbon to which they are attached are:
- (a) heterocyclic ring;
- (b) cycloalkyl group; or
- (c) bridged cycloalkyl group;

k is an integer from 1 to 2;
T at each occurrence is independently:
- (a) a covalent bond,
- (b) carbonyl,
- (c) an oxygen,
- (d) —$S(O)_o$—; or
- (e) —$N(R_a)R_i$—;

o is an integer from 0 to 2;
Q is:
- (a) —C(O)—U—$D^1$;
- (b) —$CO_2$-lower alkyl;
- (c) tetrazolyl-5-yl;
- (d) —$C(R^7)(R^8)(S—D^1)$;
- (e) —$C(R^7)(R^8)(O—D^1)$; or
- (f) —$C(R^7)(R^8)$(O-lower alkyl);

$R_a$ is:
- (a) a lone pair of electron;
- (b)1 hydrogen; or
- (c) lower alkyl;

$R_i$ is:
- (a) hydrogen;
- (b) alkyl;
- (c) aryl;
- (d) alkylcarboxylic acid;
- (e) arylcarboxylic acid;
- (f) alkylcarboxylic ester;
- (g) arylcarboxylic ester;
- (h) alkylcarboxamido;
- (i) arylcarboxamido;
- (j) alkylsulfinyl;
- (k) alkylsulfonyl;
- (l) alkylsulfonyloxy,
- (m) arylsulfinyl;
- (n) arylsulfonyl;
- (o) arylsulphonyloxy;
- (p) sulfonamido;
- (q) carboxamido;
- (r) carboxylic ester;
- (s) aminoalkyl;
- (t) aminoaryl;
- (v) a bond to an adjacent atom creating a double bond to that atom; or (w) —(N$_2$O$_2$)$^{31}$ .M$^+$, wherein M$^+$ is an organic or inorganic cation; and with the proviso that the compound of Formula III must contain at least one nitrite, nitrate, thionitrite or thionitrate group.

27. A compound of Formula (III), or a pharmaceutically acceptable salt thereof,
wherein the compound of Formula (III) is:

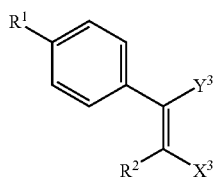

III wherein:
R$^1$ is:
(a) —S(O)$_2$—CH$_3$;
(b) —S(O)$_2$—NR$^8$(D$^1$);
(c) —S(O)$_2$—N(D$^1$)—C(O)—CF$_3$;
(d) —S(O)—(NH)—NH(D$^1$);
(e) —S(O)—(NH)—N(D$^1$)—C(O)—CF$_3$;
(f) —P(O)(CH$_3$)NH(D$^1$);
(g) —P(O)(CH$_3$)$_2$;
(h) —C(S)—NH(D$^1$);
(i) —S(O)(NH)CH$_3$;
(j) —P(O)(CH$_3$)OD$^1$; or
(k) —P(O)(CH$_3$)NH(D$^1$);

R$^2$ is:
(a) lower alkyl;
(b) cycloalkyl;
(c) mono-, di- or tri-substituted phenyl or naphthyl, wherein the substituents are each independently:
  (1) hydrogen;
  (2) halo;
  (3) alkoxy;
  (4) alkylthio;
  (5) CN;
  (6) haloalkyl;
  (7) lower alkyl;
  (8) N$_3$;
  (9) —CO$_2$D$^1$;
  (10) —CO$_2$-lower alkyl;
  (11) —(C(R$^5$)(R$^6$))$_z$—OD$^1$;
  (12) —(C(R$^5$)(R$^6$))$_z$—O-lower alkyl;
  (13) lower alkyl-CO$_2$—R$^5$;
  (14) —OD$^1$;
  (15) haloalkoxy;
  (16) amino;
  (17) nitro;
  (18) alkylsulfinyl; or
  (19) heteroaryl;
(d) mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; wherein the substituents are each independently:
  (1) hydrogen;
  (2) halo;
  (3) lower alkyl;
  (4) alkoxy;
  (5) alkylthio;
  (6) CN;
  (7) haloalkyl;
  (8) N$_3$;
  (9) —C(R$^5$)(R$^6$)—OD$^1$;
  (10) —C(R$^5$)(R$^6$)—O-lower alkyl; or
  (11) alkylsulfinyl;
(e) benzoheteroaryl which includes the benzo fused analogs of (d);
(f) —NR$^{10}$R$^{11}$;
(g) —SR$^{11}$;
(h) —OR$^{11}$;
(i) —R$^{11}$;
(I) alkenyl;
(k) alkynyl;
(l) unsubstituted, mono-, di-, tri- or tetra-substituted cycloalkenyl, wherein the substituents are each independently:
  (1) halo;
  (2) alkoxy;
  (3) alkylthio;
  (4) CN;
  (5) haloalkyl;
  (6) lower alkyl;
  (7) N$_3$;
  (8) —CO$_2$D$^1$;
  (9) —CO$_2$-lower alkyl;
  (10) —C(R$^{12}$)(R$^{13}$)—OD$^1$;
  (11) —C(R$^{12}$)(R$^{13}$)—O-lower alkyl;
  (12) lower alkyl-CO$_2$—R$^{12}$;
  (13) benzyloxy;
  (14) —O-(lower alkyl)-CO$_2$R$^{12}$;
  (15) —O-(lower alkyl)-NR$^{12}$R$^{13}$; or
  (16) alkylsulfinyl;
(m) mono-, di-, tri- or tetra-substituted heterocycloalkyl group of 5, 6 or 7 members, or a benzoheterocycle, wherein said heterocycloalkyl or benzoheterocycle has 1 or 2 heteroatoms selected from O, S, or N and, optionally, a carbonyl group or a sulfonyl group, and wherein said substituents are each independently:
  (1) halo;
  (2) lower alkyl;
  (3) alkoxy;
  (4) alkylthio;
  (5) CN;
  (6) haloalkyl;
  (7) N$_3$;
  (8) —C(R$^{12}$)(R$^{13}$)—OD$^1$;
  (9) —C(R$^{12}$)(R$^{13}$)—O-lower alkyl; or
  (10) alkylsulfinyl;
(n) styryl, mono or di-substituted styryl, wherein the substituent are each independently:
  (1) halo;
  (2) alkoxy;
  (3) alkylthio;
  (4) CN;
  (5) haloalkyl;
  (6) lower alkyl;
  (7) N$_3$;
  (8) —CO$_2$D$^1$;
  (9) —CO$_2$-lower alkyl;
  (10) —C(R$^{12}$)(R$^{13}$)—OD$^1$;
  (11) —C(R$^{12}$)(R$^{13}$)—O-lower alkyl;
  (12) lower alkyl-CO$_2$—R$^{12}$;
  (13) benzyloxy;

(14) —O-(lower alkyl)-CO$_2$R$^{12}$; or
(15) —O-(lower alkyl)-NR$^{12}$R$^{13}$;
(o) phenylacetylene, mono- or di-substituted phenylacetylene, wherein the substituents are each independently:
  (1) halo;
  (2) alkoxy;
  (3) alkylthio;
  (4) CN;
  (5) haloalkyl;
  (6) lower alkyl;
  (7) N$_3$;
  (8) —CO$_2$D$^1$;
  (9) —CO$_2$-lower alkyl;
  (10) —C(R$^{12}$)(R$^{13}$)—OD$^1$;
  (11) —C(R$^{12}$)(R$^{13}$)—O-lower alkyl;
  (12) lower alkyl-CO$_2$—R$^{12}$;
  (13) benzyloxy;
  (14) —O-(lower alkyl)-CO$_2$R$^{12}$; or
  (15) —O-(lower alkyl)-NR$^{12}$R$^{13}$;
(p) fluoroalkenyl;
(q) mono- or di-substituted bicyclic heteroaryl of 8, 9 or 10 members, consisting of 2, 3, 4 or 5 heteroatoms, wherein at least one heteroatom resides on each ring of said bicyclic heteroaryl, said heteroatoms are each independently O, S and N and said substituents are each independently:
  (1) hydrogen;
  (2) halo;
  (3) lower alkyl;
  (4) alkoxy;
  (5) alkylthio;
  (6) CN;
  (7) haloalkyl;
  (8) N$_3$;
  (9) —C(R$^5$)(R$^6$)—OD$^1$; or
  (10) —C(R$_5$)(R$_6$)—O-lower alkyl;
(r) K;
(s) aryl;
(t) arylalkyl;
(u) cycloalkylalkyl;
(v) —C(O)R$^{11}$;
(u) hydrogen;
(v) arylalkenyl;
(w) arylalkoxy;
(x) alkoxy;
(y) aryloxy;
(z) cycloalkoxy;
(aa) arylthio;
(bb) alkylthio;
(cc) arylalkylthio; or
(dd) cycloalkylthio;
X$^3$ is:
  (a) —C(O)—U—D$^1$;
  (b) —CH$_2$—U—D$^1$;
  (c) —CH$_2$—C(O)—CH$_3$;
  (d) —CH$_2$—CH$_2$—C(O)—U—D$^1$;
  (e) —CH$_2$—O—D$^1$; or
  (f) —C(O)H
Y$^3$ is:
  (a) —(CR$^5$(R$^{5'}$))$_k$—U—D$^1$;
  (b) —CH$_3$;
  (c) —CH$_2$OC(O)R$^6$; or
  (d) —C(O)H;
alternatively, X$^3$ and Y$^3$ taken together are —CR$^{82}$(R$^{83}$)—CR$^{82'}$(R$^{83'}$)—;
R$^{82}$, R$^{82'}$, R$^{83}$ and R$^{83'}$ are each independently:
  (a) hydrogen;
  (b) hydroxy;
  (c) alkyl;
  (d) alkoxy;
  (e) lower alkyl-OD$^1$;
  (f) alkylthio;
  (g) CN;
  (h) —C(O)R$^{84}$; or
  (i) —OC(O)R$^{85}$;
R$^{84}$ is:
  (a) hydrogen;
  (b) lower alkyl; or
  (c) alkoxy;
R$^{85}$ is:
  (a) lower alkyl;
  (b) alkoxy
  (c) unsubstituted, mono-, di- or tri-substituted phenyl or pyridyl, wherein the substituents are each independently:
    (1) halo;
    (2) alkoxy;
    (3) haloalkyl;
    (4) CN;
    (5) —C(O)R$^{84}$;
    (6) lower alkyl;
    (7) —S(O)$_o$-lower alkyl; or
    (8) —OD$^1$;
alternatively, R$^{82}$ and R$^{83}$ or R$^{82'}$ and R$^{83'}$ taken together are:
  (a) oxo;
  (b) thial;
  (c) =CR$^{86}$R$^{87}$; or
  (d) =NR$^{88}$;
R$^{86}$ and R$^{87}$ are each independently:
  (a) hydrogen;
  (b) lower alkyl;
  (c) lower alkyl-OD$^1$;
  (d) CN; or
  (e) —C(O)R$^{84}$;
R$^{88}$ is:
  (a) OD$^1$;
  (b) alkoxy;
  (c) lower alkyl; or
  (d) unsubstituted, mono-, di- or tri-substituted phenyl or pyridyl, wherein the substituents are each independently:
    (1) halo;
    (2) alkoxy;
    (3) haloalkyl;
    (4) CN;
    (5) —C(O)R$^{84}$;
    (6) lower alkyl;
    (7) —S(O)$_o$-lower alkyl; or
    (8) —OD$^1$;
R$^5$ and R$^{5'}$ are each independently:
  (a) hydrogen;
  (b) amino;
  (c) CN;
  (d) lower alkyl;
  (e) haloalkyl;
  (f) alkoxy;
  (g) alkylthio;
  (h) Q;
  (i) —O—Q;
  (j) —S—Q;
  (k) K;
  (l) cycloalkoxy;

(m) cycloalkylthio;
(n) unsubstituted, mono-, or di-substituted phenyl or unsubstituted, mono-, or di-substituted benzyl, wherein the substituents are each independently:
  (1) halo;
  (2) lower alkyl;
  (3) alkoxy;
  (4) alkylthio;
  (5) CN;
  (6) haloalkyl;
  (7) $N_3$;
  (8) Q;
  (9) nitro; or
  (10) amino;
(o) unsubstituted, mono-, or di-substituted heteroaryl or unsubstituted, mono-, or di-substituted heteroarylmethyl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; said substituents are each independently:
  (1) halo;
  (2) lower alkyl;
  (3) alkoxy;
  (4) alkylthio;
  (5) CN;
  (6) haloalkyl;
  (7) $N_3$;
  (8) —$C(R^6)(R^7)$—$OD^1$;
  (9) —$C(R^6)(R^7)$—O-lower alkyl; or
  (10) alkylsulfinyl
(p) —$CON(R^8)(R^8)$;
(q) —$CH_2OR^8$;
(r) —$CH_2OCN$;
(s) unsubstituted or substituted:
  (1) lower alkyl-Q;
  (2) —O-lower alkyl-Q;
  (3) —S-lower alkyl-Q;
  (4) lower alkyl-O-lower alkyl-Q;
  (5) lower alkyl-S-lower alkyl-Q;
  (6) lower alkyl-O—Q;
  (7) lower alkyl-S—Q;
  (8) lower alkyl-O—K;
  (9) lower alkyl-S—K;
  (10) lower alkyl-O—V; or
  (11) lower alkyl-S—V;
wherein the substituent(s) resides on the lower alkyl;
(t) cycloalkyl;
(u) aryl;
(v) arylalkyl;
(w) cycloalkylalkyl;
(x) aryloxy;
(y) arylalkoxy;
(z) arylalkylthio;
(aa) cycloalkylalkoxy;
(bb) heterocycloalkyl;
(cc) alkylsulfonyloxy;
(dd) alkylsulfonyl;
(ee) arylsulfonyl;
(ff) arylsulfonyloxy;
(gg) —$C(O)R^{10}$;
(hh) nitro;
(ii) amino;
(jj) aminoalkyl;
(kk) —C(O)-alkyl-heterocyclic ring;
(ll) halo;
(mm) heterocyclic ring;
(nn) —$CO_2D^1$;
(oo) carboxyl;
(pp) amidyl; or
(qq) alkoxyalkyl;
alternatively, $R^5$ and $R^5$ taken together with the carbon to which they are attached are:
  (a) cycloalkyl; or
  (b) heterocyclic ring;
$R^6$ and $R^7$ are each independently:
  (a) hydrogen;
  (b) unsubstituted, mono- or di-substituted phenyl; unsubstituted, mono- or di-substituted benzyl; unsubstituted, mono- or di-substituted heteroaryl; mono- or di-substituted heteroarylmethyl, wherein said substituents are each independently:
    (1) halo;
    (2) lower alkyl;
    (3) alkoxy;
    (4) alkylthio;
    (5) CN;
    (6) haloalkyl;
    (7) $N_3$;
    (8) —$C(R^{14})(R^{15})$—$OD^1$; or
    (9) —$C(R^{14})(R^{15})$—O-lower alkyl;
  (c) lower alkyl;
  (d) —$CH_2OR^8$;
  (e) CN;
  (f) —$CH_2CN$;
  (g) haloalkyl;
  (h) —$CON(R^8)(R^8)$;
  (i) halo; or
  (j) —$OR^8$;
$R^8$ is:
  (a) hydrogen;
  (b) K; or
  (c) $R^9$;
alternatively, $R^5$ and $R^{5'}$, $R^6$ and $R^7$ or $R^7$ and R8 together with the carbon to which they are attached form a saturated monocyclic ring of 3, 4, 5, 6 or 7 atoms; and optionally up to two heteroatoms selected from oxygen, $S(O)_o$ or $NR_i$;
$R^9$ is:
  (a) lower alkyl;
  (b) lower alkyl-$CO_2D^1$;
  (c) lower alkyl-$NHD^1$;
  (d) phenyl or mono-, di- or tri-substituted phenyl, wherein the substituents are each independently:
    (1) halo;
    (2) lower alkyl;
    (3) alkoxy;
    (4) alkylthio;
    (5) lower alkyl-$CO_2D^1$;
    (6) lower alkyl-$NHD^1$;
    (7) CN;
    (8) $CO_2D^1$; or
    (9) haloalkyl;
  (e) benzyl, mono-, di- or tri-substituted benzyl, wherein the substituents are each independently:
    (1) halo;
    (2) lower alkyl;
    (3) alkoxy;
    (4) alkylthio;
    (5) lower alkyl-$CO_2D^1$;
    (6) lower alkyl-$NHD^1$;
    (7) CN;

(8) —CO$_2$D$^1$; or
(9) haloalkyl;
(f) cycloalkyl;
(g) K; or
(h) benzoyl, mono-, di-, or trisubstituted benzoyl, wherein the substituents are each independently:
  (1) halo;
  (2) lower alkyl;
  (3) alkoxy;
  (4) alkylthio;
  (5) lower alkyl-CO$_2$D$^1$;
  (6) lower alkyl-NHD$^1$;
  (7) CN;
  (8) —CO$_2$D$^1$; or
  (9) haloalkyl;
R$^{10}$ is:
  (a) hydrogen; or
  (b) R$^{11}$;
R$^{11}$ is:
  (a) lower alkyl;
  (b) cycloalkyl;
  (c) unsubstituted, mono-, di- or tri-substituted phenyl or naphthyl, wherein the substituents are each independently:
    (1) halo;
    (2) alkoxy;
    (3) alkylthio;
    (4) CN;
    (5) haloalkyl;
    (6) lower alkyl;
    (7) N$_3$;
    (8) —CO$_2$D$^1$;
    (9) —CO$_2$-lower alkyl;
    (10) —C(R$^{12}$)(R$^{13}$)—OD$^1$
    (11) —C(R$^{12}$)(R$^{13}$)—O-lower alkyl;
    (12) lower alkyl-CO$_2$D$^1$;
    (13) lower alkyl-CO$_2$R$^{12}$;
    (14) benzyloxy;
    (15) —O-(lower alkyl)-CO$_2$D$^1$;
    (16) —O-(lower alkyl)-CO$_2$R$^{12}$; or
    (17) —O-(lower alkyl)-NR$^{12}$R$^{13}$;
  (d) unsubstituted, mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or said heteroaryl is a monocyclic ring of 6 atoms, said ring having one heteroatom which is N, and, optionally 1, 2, or 3 additional N atoms, and wherein said substituents are each independently:
    (1) halo;
    (2) lower alkyl;
    (3) alkoxy;
    (4) alkylthio;
    (5) CN;
    (6) haloalkyl;
    (7) N$_3$;
    (8) —C(R$^{12}$)(R$^{13}$)—OD$^1$; or
    (9) —C(R$^{12}$)(R$^{13}$)—O-lower alkyl;
  (e) unsubstituted, mono- or di-substituted benzoheterocycle, wherein the benzoheterocycle is a 5, 6, or 7-membered ring with 1 or 2 heteroatoms independently selected from O, S, or N, and, optionally, a carbonyl group or a sulfonyl group, wherein said substituents are each independently:
    (1) halo;
    (2) lower alkyl;
    (3) alkoxy;
    (4) alkylthio;
    (5) CN;
    (6) haloalkyl;
    (7) N$_3$;
    (8) —C(R$^{12}$)(R$^{13}$)—OD$^1$; or
    (9) —C(R$^{12}$)(R$^{13}$)—O-lower alkyl;
  (f) unsubstituted, mono- or di-substituted benzocarbocycle, wherein the carbocycle is a 5, 6, or 7-membered ring has optionally a carbonyl group, wherein said substituents are each independently:
    (1) halo;
    (2) lower alkyl;
    (3) alkoxy;
    (4) alkylthio;
    (5) CN;
    (6) haloalkyl;
    (7) N$_3$;
    (8) —C(R$^{12}$)(R$^{13}$)—OD$^1$; or
    (9) —C(R$^{12}$)(R$^{13}$)—O-lower alkyl;
  (g) hydrogen; or
  (h) K
R$^{12}$ and R$^{13}$ are each independently:
  (a) hydrogen;
  (b) lower alkyl; or
  (c) aryl; or
R$^{12}$ and R$^{13}$ together with the atom to which they are attached form a saturated monocyclic ring of 3, 4, 5, 6 or 7 atoms;
R$^{14}$ and R$^{15}$ are each independently:
  (a) hydrogen; or
  (b) lower alkyl; or
R$^{14}$ and R$^{15}$ together with the atom to which they are attached form a carbonyl, a thial, or a saturated monocyclic ring of 3, 4, 5, 6 or 7 atoms; and
D$^1$ is a hydrogen atom, V or K;
Q is:
  (a) —C(O)—U—D$^1$;
  (b) —CO$_2$-lower alkyl;
  (c) tetrazolyl-5-yl;
  (d) —C(R$^7$)(R$^8$)(S—D$^1$);
  (e) —C(R$^7$)(R$^8$)(O—D$^1$); or
  (f) —C(R$^7$)(R$^8$)(O-lower alkyl);
K is -(linking group)-U—V;
U is:
  (a) oxygen;
  (b) sulfur; or
  (c) —N(R$_a$)R$_i$—;
V is:
  (a) —NO; or
  (b) —NO$_2$;
R$_a$ is:
  (a) a lone pair of electron;
  (b) hydrogen; or
  (c) lower alkyl;
R$_i$ is:
  (a) hydrogen;
  (b) alkyl;
  (c) aryl;
  (d) alkylcarboxylic acid;
  (e) arylcarboxylic acid;
  (f) alkylcarboxylic ester;
  (g) arylcarboxylic ester;
  (h) alkylcarboxamido;
  (i) arylcarboxamido;
  (j) alkylsulfinyl;
  (k) alkylsulfonyl;

(l) alkylsulfonyloxy,
(m) arylsulfinyl;
(n) arylsulfonyl;
(o) arylsulphonyloxy;
(p) sulfonamido;
(q) carboxamido;
(r) carboxylic ester;
(s) aminoalkyl;
(t) aminoaryl;
(u) —CH$_2$—C(U—V)(R$_e$)(R$_f$);
(v) a bond to an adjacent atom creating a double bond to that atom; or
(w) —(N$_2$O$_2$—)$^-$.M$^+$, wherein M is an organic or inorganic cation;

R$_e$ and R$_f$ are each independently:
(a) hydrogen;
(b) alkyl;
(c) cycloalkoxy;
(d) halogen;
(e) hydroxy;
(f) hydroxyalkyl;
(g) alkoxyalkyl;
(h) arylheterocyclic ring;
(i) cycloalkylalkyl;
(j) heterocyclicalkyl;
(k) alkoxy;
(l) haloalkoxy;
(m) amino;
(n) alkylamino;
(o) dialkylamino;
(p) arylamino;
(q) diarylamino;
(r) alkylarylamino;
(s) alkoxyhaloalkyl;
(t) haloalkoxy;
(u) sulfonic acid;
(v) alkylsulfonic acid;
(w) arylsulfonic acid;
(x) arylalkoxy;
(y) alkylthio;
(z) arylthio;
(aa) cyano;
(bb) aminoalkyl;
(cc) aminoaryl;
(dd) alkoxy;
(ee) aryl;
(ff) arylalkyl;
(gg) carboxamido;
(hh) alkylcarboxamido;
(ii) arylcarboxamido;
(jj) amidyl;
(kk) carboxyl;
(ll) carbamoyl;
(mm) alkylcarboxylic acid;
(nn) arylcarboxylic acid;
(oo) alkylcarbonyl;
(pp) arylcarbonyl;
(qq) ester;
(rr) carboxylic ester;
(ss) alkylcarboxylic ester;
(tt) arylcarboxylic ester;
(uu) haloalkoxy;
(vv) sulfonamido;
(ww) alkylsulfonamido;
(xx) arylsulfonamido;
(yy) alkylsulfonyl,
(zz) alkylsulfonyloxy,
(aaa) arylsulfonyl,
(bbb) arylsulphonyloxy
(ccc) sulfonic ester;
(ddd) carbamoyl;
(eee) urea;
(fff) nitro; or
(ggg) —U—V; or R$_e$ and R$_f$ taken together are:
(a) oxo;
(b) thial; or R$_e$ and R$_f$ taken together with the carbon to which they are attached are:
(a) heterocyclic ring;
(b) cycloalkyl group; or
(c) bridged cycloalkyl group; and with the proviso that the compound of Formula (III) must have at least one NO group, at least one NO$_2$ group or at least one NO and NO$_2$ group, wherein the at least one NO group, the least one NO$_2$ group or the at least one NO and NO$_2$ group is linked to the compound of Formula (III) through an oxygen atom, a nitrogen atom or a sulfur atom.

28. A method for treating arthritis in a patient in need thereof comprising administering to the patient a therapeutically effective amount of the composition of claim 2, 3, 7 or 15.

\* \* \* \* \*